(12) United States Patent
Hafner et al.

(10) Patent No.: US 8,551,493 B2
(45) Date of Patent: Oct. 8, 2013

(54) PEPTIDE WITH REDUCED DIMER FORMATION

(75) Inventors: Roderick Peter Hafner, Oxford (GB); Paul Laidler, Oxford (GB)

(73) Assignee: Circassia Limited, Oxford (GB)

(*) Notice: Subject to any disclaimer, the term of this patent is extended or adjusted under 35 U.S.C. 154(b) by 510 days.

(21) Appl. No.: 12/673,334

(22) PCT Filed: Aug. 15, 2008

(86) PCT No.: PCT/GB2008/002779
§ 371 (c)(1),
(2), (4) Date: Feb. 19, 2010

(87) PCT Pub. No.: WO2009/022155
PCT Pub. Date: Feb. 19, 2009

(65) Prior Publication Data
US 2011/0123558 A1 May 26, 2011

(30) Foreign Application Priority Data

Aug. 15, 2007 (GB) .................................. 0715949.4
Aug. 20, 2007 (GB) .................................. 0716224.1
Nov. 28, 2007 (GB) .................................. 0723337.2

(51) Int. Cl.
| A61K 38/00 | (2006.01) |
| A61K 38/04 | (2006.01) |
| A61K 39/00 | (2006.01) |
| C07K 2/00  | (2006.01) |
| C07K 4/00  | (2006.01) |
| C07K 5/00  | (2006.01) |
| C07K 7/00  | (2006.01) |
| C07K 14/00 | (2006.01) |
| C07K 16/00 | (2006.01) |
| C07K 17/00 | (2006.01) |

(52) U.S. Cl.
USPC .......... 424/185.1; 530/300; 530/326; 530/327

(58) Field of Classification Search
None
See application file for complete search history.

(56) References Cited

U.S. PATENT DOCUMENTS

| 4,442,212 | A   | 4/1984  | Briggs |
| 5,547,669 | A   | 8/1996  | Rogers et al. |
| 5,820,862 | A   | 10/1998 | Garman et al. |
| 6,019,972 | A   | 2/2000  | Gefter et al. |
| 6,204,036 | B1  | 3/2001  | Metzner et al. |
| 6,982,326 | B1  | 1/2006  | Griffith et al. |
| 7,786,257 | B2* | 8/2010  | Murray et al. ............... 530/325 |
| 2004/0071718 | A1 | 4/2004 | Tsai |
| 2005/0107585 | A1* | 5/2005 | Murray et al. ............... 530/350 |
| 2006/0024334 | A1 | 2/2006 | Larche et al. |
| 2006/0057641 | A1 | 3/2006 | Morgenstern et al. |
| 2008/0293624 | A1 | 11/2008 | Hageman et al. |
| 2010/0239599 | A1* | 9/2010 | Hafner et al. ............... 424/185.1 |

FOREIGN PATENT DOCUMENTS

| CN | 1283997 A       | 2/2001  |
| EP | 0044532         | 1/1982  |
| EP | 1958645         | 8/2008  |
| WO | WO 93/08279     | 4/1993  |
| WO | WO 93/20842     | 10/1993 |
| WO | WO 94/21675     | 9/1994  |
| WO | WO 94/24281     | 10/1994 |
| WO | WO 94/27634     | 12/1994 |
| WO | WO 95/06728     | 3/1995  |
| WO | WO 95/20599     | 8/1995  |
| WO | WO 95/28424     | 10/1995 |
| WO | WO 96/13517     | 5/1996  |
| WO | WO 97/00027     | 1/1997  |
| WO | WO 97/35193  *  | 9/1997  |
| WO | WO 99/32135     | 7/1999  |
| WO | WO 99/34826     | 7/1999  |
| WO | WO 00/44781     | 8/2000  |
| WO | WO 02/16410 A2  | 2/2002  |
| WO | WO 02/062834 A3 | 8/2002  |
| WO | WO 02/080848 A2 | 10/2002 |
| WO | WO 03/042344    | 5/2003  |
| WO | WO 03/047618 A2 | 6/2003  |
| WO | WO 03/082924 A1 | 10/2003 |
| WO | WO 2004/078098 A2 | 9/2004 |
| WO | WO 2005/000891 A2 | 1/2005 |
| WO | WO 2005/047323  | 5/2005  |
| WO | WO 2006/017773  | 2/2006  |
| WO | WO 2006/082313 A3 | 8/2006 |
| WO | WO 2006/083906  | 8/2006  |
| WO | WO 2007/129093 A2 | 11/2007 |
| WO | WO 2008/115428  | 9/2008  |
| WO | WO 2008/145998 A1 | 12/2008 |

OTHER PUBLICATIONS

Dick et al. 'Proteolytic Processing of Ovalbumin and P-galactosidase by the Proteasome to Yield Antigenic Peptides.'1. J. Immunol. 152(8): 3884-3894, 1994.*

Banga et al. 'Therapeutic Peptides and Proteins Formulation, Processing, and Delivery Systems, Second Edition' Chapter 3, pp. 67-89, 2005.*

Cromwell et al., "Transition of Recombinant Allergens from Bench to Clinical Application," Methods 32:300-312, 2004.

van de Wal et al., "Peptide Binding Characteristics of the Coeliac Disease-Associated DQ(α1*0501, β1*0201) Molecule," Immunogenetics 44:246-253, 1996.

(Continued)

*Primary Examiner* — Nora Rooney
(74) *Attorney, Agent, or Firm* — Clark & Elbing LLP

(57) ABSTRACT

The present invention relates to peptides which are formulated or engineered to prevent or reduce the formation of dimers.

4 Claims, 1 Drawing Sheet

(56) References Cited

OTHER PUBLICATIONS

Walker et al., "Mapping Major and Minor T-Cell Epitopes in Vitro and Their Immunogenic or Tolerogenic Effect in Vivo in Non-Human Primates," Immunology 80:209-216, 1993.
Zhu et al., "T Cell Epitope Mapping of Ragweed Pollen Allergen *Ambrosia artemisiifolia* (Amb a 5) and *Ambrosia trifida* (Amb t 5) and the Role of Free Sulfhydryl Groups in T Cell Recognition," J. Immunol. 155:5064-5073, 1995.
Ebner et al., "Nonallergic Individuals Recognize the Same T Cell Epitopes of Bet v 1, the Major Birch Pollen Allergen, as Atopic Patients," J. Immunol. 154:1932-1940, 1995.
Harris et al., "Permissive Recognition of a Mycobacterial T-Cell Epitope: Localization of Overlapping Epitope Core Sequences Recognized in Association with Multiple Major Histocompatibility Complex Class ll I-A Molecules," Immunology 84:555-561, 1995.
Jeannin et al., "Immunogenicity and Antigenicity of Synthetic Peptides Derived from the Mite Allergen *Der p* I," Mol. Immunol. 30:1511-1518, 1993.
Krco et al., "Immune Response of HLA-DQ Transgenic Mice to House Dust Mite Allergen p2: Identification of HLA-DQ Restricted Minimal Epitopes and Critical Residues," Clin. Immunol. 97:154-161, 2000.
Kristensen et al., "Induction of T Cell Responses to the Invariant Chain Derived Peptide CLIP in Mice Immunized with the Group 1 Allergen of House Dust Mite," Int. Immunol. 8:1091-1098, 1996.
Larché et al., "Peptide-Based Therapeutic Vaccines for Allergic and Autoimmune Diseases," Nat. Med. 11:569-576, 2005.
Mustafa, "Identification of Mycobacterial Peptide Epitopes Recognized by CD4[+] T Cells in Association with Multiple Major Histocompatibility Complex Class II Molecules," Nutrition 11:657-660, 1995.
Nagato et al., "Functional Analysis of Birch Pollen Allergen Bet v 1-Specific Regulatory T Cells," J. Immunol. 178:1189-1198, 2007.
Ohkuri et al., "Identification of a Novel NY-ESO-1 Promiscuous Helper Epitope Presented by Multiple MHC Class II Molecules Found Frequently in the Japanese Population," Cancer Sci. 98:1092-1098, 2007.
Rao et al., "Mapping of Thyroglobulin Epitopes: Presentation of a 9mer Pathogenic Peptide by Different Mouse MHC Class II Isotypes," Immunogenetics 40:352-359, 1994.
Schafer et al., "Prediction of Well-Conserved HIV-1 Ligands Using a Matrix-Based Algorithm, EpiMatrix," Vaccine 16:1880-1884, 1998.
Tamborini et al., "Biochemical and Immunological Characterization of Recombinant Allergen Lol p 1," Eur. J. Biochem. 249:886-894, 1997.
Texier et al., "Emerging Principles for the Design of Promiscuous HLA-DR-Restricted Peptides: An Example from the Major Bee Venom Allergen," Eur. J. Immunol. 32:3699-3707, 2002.
Verhoef et al., "Threshold Signaling of Human Th0 Cells in Activation and Anergy: Modulation of Effector Function by Altered TCR Ligand," J. Immunol. 164:6034-6040, 2000.
Alexander et al., "Fel d 1-Derived T Cell Peptide Therapy Induces Recruitment of CD4[+]CD25[+]; CD4[+] Interferon-gamma[+] T Helper Type 1 Cells to Sites of Allergen-Induced Late-Phase Skin Reactions in Cat-Allergic Subjects," Clin. Exp. Allergy 35:52-58, 2005.
Alexander et al., "The Effect of Fel d 1-Derived T-Cell Peptides on Upper and Lower Airway Outcome Measurements in Cat-Allergic Subjects," Allergy 60:1269-1274, 2005.
Ali et al., "Late Asthmatic Reactions Induced by Inhalation of Allergen-Derived T Cell Peptides," Am. J. Respir. Crit. Care Med. 169:20-26, 2004.
Ali et al., "The Potential of Peptide Immunotherapy in Allergy and Asthma," Curr. Allergy Asthma Rep. 2:151-158, 2002.
De Groot et al., "Immuno-Informatics: Mining Genomes for Vaccine Components," Immunol. Cell Biol. 80:255-269, 2002.
Fellrath et al., "Allergen-Specific T-Cell Tolerance Induction with Allergen-Derived Long Synthetic Peptides: Results of a Phase I Trial," J. Allergy Clin. Immunol. 111:854-861, 2003.
Gotte et al., "Oligomerization of ribonuclease A under reducing conditions," Biochimica et Biophysica Acta, vol. 1784:638-650, 2008.
Hafner et al., "Persistent Treatment Effect Achieved at One Year after 4 Doses of *Fel d 1*-Derived Peptide Immunotherapy in an Environmental Exposure Chamber (EEC) Model of Cat Allergy," J. Allergy Clin. Immunol. AB144, 2pgs, 2012. Abstract 546.
Haselden et al., "Late Asthmatic Reactions Provoked by Intradermal Injection of T-Cell Peptide Epitopes are not Associated with Bronchial Mucosal Infiltration of Eosinophils or $T_H2$-Type Cells or with Elevated Concentrations of Histamine or Eicosanoids in Bronchoalveolar Fluid," J. Allergy Clin. Immunol. 180:394-401, 2001.
Haselden et al., "Proliferation and Release of IL-5 and IFN-gamma by Peripheral Blood Mononuclear Cells from Cat-Allergic Asthmatics and Rhinitics, Non-Cat-Allergic Asthmatics, and Normal Controls to Peptides Derived from Fel d 1 Chain 1," J. Allergy Clin. Immunol. 108:349-356, 2001.
Kay et al., "Allergen Immunotherapy with Cat Allergen Peptides," Springer Semin. Immunopathol. 25:391-399, 2004.
Oldfield et al., "Allergen-Derived T Cell Peptide-Induced Late Asthmatic Reactions Precede the Induction of Antigen-Specific Hyporesponsiveness in Atopic Allergic Asthmatic Subjects," J. Immunol. 1734-1739, 2001.
Oldfield et al., "Effect of T-Cell Peptides Derived from Fel d 1 on Allergic Reactions and Cytokine Production in Patients Sensitive to Cats: A Randomised Controlled Trial," Lancet 360:47-53, 2002.
Smith et al., "Cat Allergen Peptide Immunotherapy Reduces CD4[+] T Cell Responses to Cat Allergen but Does Not Alter Suppression by CD4[+] CD25[+] T Cells: A Double-Blind Placebo-Controlled Study," Allergy 59:1097-1101, 2004.
Tanabe, "Epitope Peptides and Immunotherapy," Curr. Protein Pept. Sci. 8:1-10, 2007.
Verhoef et al., "T Cell Epitope Immunotherapy Induces a CD4[+] T Cell Population with Regulatory Activity," PLoS Med. 2(e78):0253-0261, 2005.
Worm et al., "Development and Preliminary Clinical Evaluation of a Peptide Immunotherapy Vaccine for Cat Allergy," J. Allergy Clin. Immunol. 127:89-97, 2011.

* cited by examiner

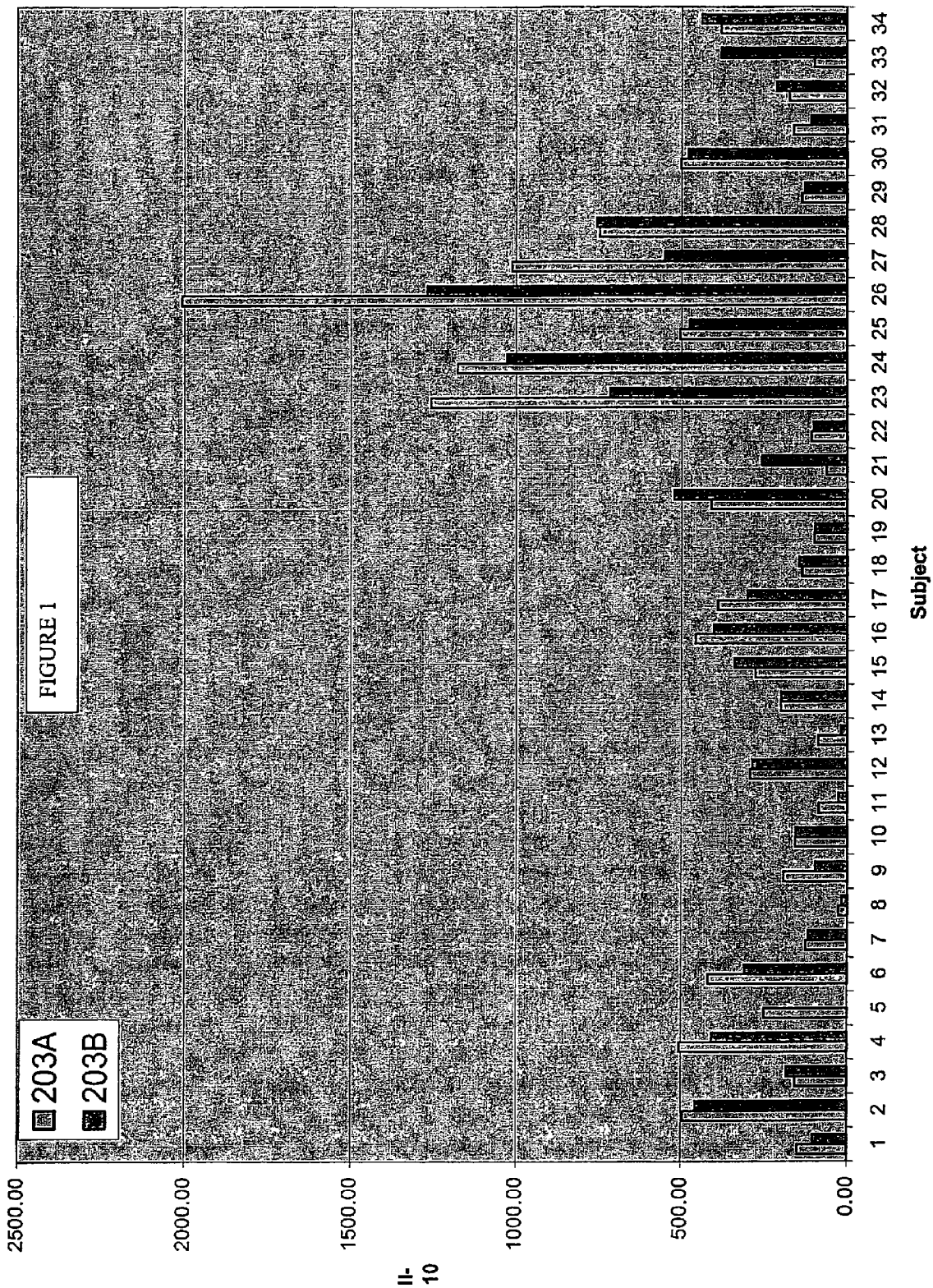

PEPTIDE WITH REDUCED DIMER FORMATION

CROSS-REFERENCE TO RELATED APPLICATIONS

This application is the U.S. national stage filing under 35 U.S.C. §371 of international application PCT/GB2008/002779, filed Aug. 15, 2008, which claims priority from Great Britain Patent Application 0715949.4, filed Aug. 15, 2007, Great Britain Patent Application 0716224.1, filed Aug. 20, 2007, and Great Britain Patent Application 0723337.2, filed Nov. 28, 2007.

FIELD OF THE INVENTION

The present invention relates to peptides which are engineered or formulated to prevent or reduce the formation of dimers.

BACKGROUND OF THE INVENTION

T-cell antigen recognition requires antigen presenting cells (APCs) to present antigen fragments (peptides) on their cell surface in association with molecules of the major histocompatibility complex (MHC). T cells use their antigen specific T-cell receptors (TCRs) to recognise with high specificity the antigen fragments presented by the APC. Such recognition acts as a trigger to the immune system to generate a range of responses to eradicate the antigen which has been recognized. Most of the specificity of T cell recognition of the antigen fragments is provided by a smaller subsequence of amino acids within the fragments. This subsequence is known as the T cell epitope. In the case of extracellular allergens and auto- or allo-antigens, the peptides are presented on MHC Class II molecules, which are recognized by CD4 T cells. Accordingly, interest in allergic and auto- or allo-immune disorders has focused on MHC Class II-binding T cell epitopes.

Given their role in the immune system, there is considerable interest in such epitopes for use as therapeutic agents to modulate the immune systems of subjects. For example, administration of peptide epitopes to subjects has been demonstrated to result in the induction of tolerance to the antigen from which the epitope derives. Therapeutic agents based on such an effect have great potential in the prevention and treatment of allergy, and auto- or allo-immune diseases where the down-regulation of an immune response is desirable.

Further progress in this area is hindered by a number of problems. Firstly, epitope sequences from allergens and auto- and allo-antigens are often poorly soluble, and are therefore problematic both to manufacture and to administer to subjects. Secondly, the majority of epitopes have typically been poorly defined. Most epitopes known in the art are loosely identified as being a core sequence present somewhere within a longer sequence, typically of approximately twenty amino acids. The core sequence itself is often not identified. In the absence of a clear definition of the core sequence an epitope, it has not been possible to modify known T cell epitopes to improve their solubility, since this risks eliminating the core residues required for T cell recognition.

SUMMARY OF THE INVENTION

Peptides comprising T cell epitopes may be prone to the formation of dimers in solution. This can result in a loss of active species and in the case of mixtures of different peptides can result in novel degradants or heterodimers that may increase IgE or IgG binding on the surface of mast cells. Dimerisation can also lead to the aggregation of peptides as insoluble precipitates. Thus, peptides comprising T cell epitopes are often unsuitable for tolerising a subject because they provoke undesirable immune responses and/or cannot be stored for long periods without forming aggregates and/or are problematic both to manufacture and to administer to subjects.

The minimal amino acid sequence of a T cell epitope required for binding to MHC Class II-binding can be precisely identified and generally comprises approximately nine amino acids. The present inventors have made the finding that by modifying specific residues within the minimal sequence of an epitope particularly prone to dimer formation, or modifying specific residues which flank the minimal sequence, it is possible to reduce dimer formation. It is also possible to reduce dimer formation by adding certain specific agents to a composition comprising the unmodified sequence of such a peptide. Thus, a composition comprising a peptide modified as above, or comprising a peptide and an agent which inhibits dimer formation, is a composition in which the peptide is present in predominantly monomeric form, and therefore has improved solubility without reducing the ability of the peptide to stimulate specific T cells and without becoming large enough to possess significant tertiary structure that would enable it to retain the conformation of an IgG or IgE-cross-linking epitope. Consequently the downstream immune responses caused by such cross-linking do not occur, and the compositions are well suited to tolerising an individual to the protein from which the peptide derives. Furthermore, the reduced dimer formation of the compositions of the invention has further advantages for the tolerisation of individuals, since peptide dimers may be more immunogenic, possibly due to cross-linking by immunoglobulins. Accordingly, the present invention provides a composition comprising:

a) i) at least one peptide of 9 to 25 amino acids in length wherein the peptide comprises a region comprising at least one MHC Class II-binding T cell epitope; and
   ii) at least one agent which inhibits dimer formation;
or
b) i) at least one peptide as defined in a) i) wherein the amino acid sequence of the region has additionally been engineered to reduce dimer formation; and optionally
   ii) at least one agent which inhibits dimer formation,
wherein a minimal proportion of the peptide of the composition is present in solution as a dimer. The at least one peptide of a) i) is typically suitable for tolerisation therapy.

DETAILED DESCRIPTION OF THE INVENTION

It is to be understood that references to inserting, deleting, replacing amino acids herein does not require the actual physical insertion, deletion or replacement of amino acids, and instead a peptide can be synthesized comprising sequence which represents (or is the end result of) the insertion, deletion or replacement having occurred.

Amino Acids

The table below shows the properties of amino acids. Molecular weights are shown beneath the 3-letter code for each amino acid. The molecular weights given are those of the neutral, free amino acids; residue weights can be obtained by subtraction of one equivalent of water (18 g/mol). Figures were obtained from The Merck Index, (Budavari, S., ed.) Merck & Co., Rahway, (1989).

| | | | |
|---|---|---|---|
| Ala 89 | Aliphatic, hydrophobic, neutral | Met 149 | hydrophobic, neutral |
| Cys 121 | polar, hydrophobic, neutral | Asn 132 | polar, hydrophilic, neutral |
| Asp 133 | polar, hydrophilic, charged (−) | Pro 115 | hydrophobic, neutral |
| Glu 147 | polar, hydrophilic, charged (−) | Gln 146 | polar, hydrophilic, neutral |
| Phe 165 | Aromatic, hydrophobic, neutral | Arg 174 | polar, hydrophilic, charged (+) |
| Gly 75 | Aliphatic, neutral | Ser 105 | polar, hydrophilic, neutral |
| His 155 | aromatic, polar, hydrophilic, charged (+) | Thr 119 | polar, hydrophilic, neutral |
| Ile 131 | Aliphatic, hydrophobic, neutral | Val 117 | aliphatic, hydrophobic, neutral |
| Lys 146 | polar, hydrophilic, charged (+) | Trp 204 | aromatic, hydrophobic, neutral |
| Leu 131 | Aliphatic, hydrophobic, neutral | Tyr 181 | aromatic, polar, hydrophobic |

MHC Class II-Binding T Cell Epitopes

The MHC Class II-binding T cell epitope comprised in the peptides of the invention is typically the minimal amino acid sequence that is capable of binding to Class II molecules and capable of stimulating T cells when presented to T cells in association with Class II on the cell surface. The epitope is typically one that binds to a human MHC class II molecule, such as any such molecule mentioned herein.

An MHC Class II molecule consists of two proteins, α and β, each of which is encoded by a different gene. In humans, there are three clusters of genes encoding different α and β proteins. These are the Human Leukocyte Antigen (HLA) clusters, DR, DQ and DP. Each cluster comprises multiple different A genes encoding different variant of the a protein and multiple different B genes encoding different variants of the β protein. The resulting MHC Class II heterodimers are therefore extremely diverse, and correspondingly so are the T cell epitopes that they bind.

The binding site of MHC Class II molecules is composed of two separate proteins which form a cleft. The cleft is open-ended, which in theory allows a peptide of any length to bind. However, only 9 amino acids can occupy the cleft itself. The identities of the up to 9 amino acids which occupy the cleft define whether or not a given peptide will bind to a given MHC Class II molecule and be available for presentation to T cells. These up to 9 amino acids therefore represent the minimal sequence that is required for MHC Class II-binding. It is generally assumed that such a sequence will be capable of stimulating T cells when presented to T cells in association with Class II on the cell surface. However, this may be confirmed experimentally by methods standard in the art.

Such methods may typically comprise contacting the epitope with T cells in a sample taken from a subject, under conditions which allow the epitope and the T cells to interact; and then determining whether or not any of the T cells are stimulated. Determining whether or not the T cells are stimulated may be achieved by any suitable method, for example by detecting the production of cytokines by the T cells, wherein cytokine production indicates that T cells have been stimulated. Suitable cytokines include interferon gamma, interleukin 4 and interleukin 13. Cytokine production may be detected by any suitable method, for example an ELISA, ELISPOT assay or a flow cytometric assay. The T cells in a sample from a subject are typically present in a population of peripheral blood mononuclear cells (PBMCs) isolated from a blood or serum sample taken from the subject.

The MHC Class II-binding T cell epitope of the invention typically consists of 8 or 9 amino acids, but may consist of 7, 8, 9, 10, 11, 12, 13, 14, 15, 16, 17, 18, 19 or 20 amino acids. The amino acid sequence of the epitope may be broadly defined by further reference to the binding site of MHC Class II molecules. This binding site has specific binding pockets, which corresponding to primary and secondary anchor positions in the sequence of the binding peptide epitope. The binding pockets are defined by amino acid positions in the sequence of the MHC Class II molecule, and are generally not absolutely discriminatory for a specific amino acid in the epitope. Therefore the peptide binding specificity of any given MHC molecule is relatively broad. Thus, peptides binding to the same MHC allotype exhibit some degree of similarity, but there is no requirement for identity.

For the most common human MHC Class II type, HLA-DR, the key anchor positions for binding to the binding pockets are at positions 1, 4, 6, 7 and 9 of the peptide epitope (counting from the most N terminal residue occupying the cleft to the most C terminal). Different HLA-DR alleles which have similar amino acids in their binding pockets therefore typically bind peptides with similar amino acids at positions 1, 4, 6, 7 and 9. Accordingly, the region containing an MHC Class II binding T cell epitope preferably has amino acids at positions corresponding to positions 1, 4, 6, 7 and 9 that allow binding to the widest range of HLA-DR alleles. Examples of characteristic binding properties of different HLA-DR alleles are set out below:

DR alleles with Glycine at position 86 of the β chain show strong preferences for large hydrophobic side chains (Trp, Tyr, Phe) at peptide position 1, whereas Valine at position 86 restricts the pocket size and alters the preferences to small hydrophobic side chains (Val and Ala) at this position. Medium sized hydrophobic amino acids Leu and Ile are well accepted in all DR alleles.

DR alleles with Gln at position 70, Lysine at position 71, and Arginine or Gln at position 74 of the β chain have an overall positive charge within pocket 4, which requires negatively charged amino acids Asp and Glu at position 4 of the binding peptide (as in for example, DRB1*0301). DR alleles with this motif are associated with two autoimmune diseases: systematic lupus erythematosus and Hashimoto's thyroiditis.

DR alleles with Gln or Arg at position 70, Arg or Lys at position 71 and Glu or Ala at position 74 of the chain bind similar peptides to those directly above since the only significant difference is at position 74. However, when Ala is present at position 74, pocket 4 increases in size and can accommodate larger amino acids such as Phe, Trp, and Ile (as in for example DRB1*0401, 04, 05). Alleles bearing Glu at position 74 are expected to allow small polar residues, like Ser and Thr at position 4 of the binding peptide. DR alleles with this motif are associated with a susceptibility to rheumatoid arthritis.

DR alleles with Asp at position 70, Glu or Arg at position 71, and Leu or Ala at position 74 of the β chain exclude peptides with negatively charged amino acids at peptide position 4 (for example DRB1*0402). This is due to the presence of Asp at position 70. DR alleles with this motif are associated with the autoimmune diseases Juvenile rheumatoid arthritis (JRA), pemphigus vulgaris, and allergic bronchopulmonary disease/syndrome.

Polymorphisms at position 9 of the ft chain define the size of binding pocket 9 in all DR alleles. Alleles with Trp at this position accept only small amino acids in position 9 of the binding peptide, e.g. Ala, Val, Gly, Ser, Thr, Pro (as in for example DRB1*0101 and *1501). Glu at position 9, in combination with Asp at position 57, makes pocket 9 negatively charged, facilitating the accommodation of positively charged amino acids, such as Lys (as in for example DRB1*0401 and *0404) and Histine (as in for example DRB1*0402). In most MHC class II alleles, Asp at position 57 makes a salt-bridged hydrogen bond with Arg at position 76, allowing the pocket to also accommodate aliphatic and polar amino acids. In cases where Asp at position 57 is replaced by Ser (for example DRB1*0405) or Ala (DQ8), the hydrogen bonding network is destroyed and Mg at position 76 can strongly attract negatively charged amino acids such as Asp or Glu at position 9 of the binding peptide (as in for example DRB1*0405).

An example of a preferred sequence for an epitope therefore has Trp, Tyr, Phe, Val or Ala at position 1; Asp, Glu, Ser or Thr at position 4; and Ala, Val, Gly, Ser, Thr, Pro at position 9. A further example of a preferred sequence for an epitope has a large aromatic or hydrophobic amino acid at position 1, for example Tyr, Phe, Trp, Leu, Ile or Val, and a small, non-charged amino acid at position 6, for example Ser, Thr, Ala, Pro, Val, Ile or Met. Approximately 87.5% of peptides binding to all or a combination of the MHC Class II molecules encoded by the DRB1*0101, *0401 and *0701 alleles contain this motif. Furthermore, since T cell epitopes derived from allergens and autoimmune antigens do not typically contain a large number of repeats of a given amino acid or amino acids, preferred epitopes of the invention typically comprise at least 5, 6, 7 or 8 different amino acids.

The precise amino sequence of an epitope may be predicted by computer-based algorithms and confirmed by in vitro biochemical analysis. Suitable commercially available algorithms include the EpiMatrix algorithm (EpiVax Inc.). Other algorithms are available at, for example http://www.imtech.res.in/raghava/propred/ and http://www.imtech.res.in/raghava/mhc2pred/. Analysis with these algorithms typically comprises parsing a larger polypeptide sequence into multiple overlapping small peptides. The sequences of these small peptides are then analysed using the algorithm to identify those which are predicted to bind MHC Class II molecules. The overlapping small peptides are typically 9-mers.

The candidate peptides which score most highly in this analysis are then assessed for the ability to bind a panel of MHC Class II molecules encoded by different Class II alleles in vitro using standard binding assays. For example a competitive MHC class II binding assay may be used, wherein each peptide is analysed for its ability to displace a known control binder from each of the human MHC class II allotypes investigated. In such an assay each peptide is assigned an $IC_{50}$ value (the concentration at which 50% inhibition of control peptide binding is achieved). The lower the $IC_{50}$ the higher the affinity of a peptide for a given MHC class II allotype.

The epitope or epitopes in a polypeptide are taken to be those peptides which show the highest binding affinity to MHC Class II molecules. Particularly preferred epitopes show high affinity binding to different Class II molecules encoded by more than one preferably two, more preferably three, four or five MHC Class II alleles.

Particularly preferred epitopes are those which are comprised in regions which are prone to dimer formation, as defined below.

Regions Containing at Least One MHC Class II-Binding T Cell Epitope

Biochemical assays for the identification of a T cell epitope are not typically able to define the position of the minimal epitope sequence within a larger sequence more accurately than to within approximately 12 amino acids, and more typically 15, 20 or more amino acids. The reason for this is that a large sequence must be physically fragmented into smaller overlapping peptides, or smaller overlapping peptides must be manufactured de novo prior to in vitro assessment of the ability of these peptides to bind MHC Class II molecules. The skilled person will recognise that the smaller the overlapping peptide fragments used, the more time-consuming and labour intensive is the process of manufacture. Hence epitopes are often identified as being contained within a larger polypeptide region. It is envisaged that the peptides of the invention may comprise such a larger region. Accordingly, in the peptides of the invention, the region containing an MHC Class II-binding T cell epitope is typically 8 or 9 amino acids in length, but may be 10, 11, 12, 13, 14, 15, 16, 17, 18, 19, 20, 21, 22, 23, 24 or 25 amino acids in length.

The region of the invention is typically a sequence which is prone to dimer formation. This will be understood to include both homodimer formation (i.e. association of peptide monomers with other identical peptide monomers) and heterodimer formation (i.e. association of peptide monomers with different peptide monomers). It will also be understood that by a sequence prone to dimer formation, it is also intended to refer to sequences which are prone to form higher order oligomers, such as trimers, tetramers and the like. The region of the invention may comprise or consist of any sequence which is prone to dimer formation. The particular amino acid sequence within a given region which promotes dimer formation may be comprised within the minimal MHC class II-binding sequence of the T cell epitope, or may be comprised within the residues which flank this sequence. The sequence prone to dimer formation may thus consist entirely of the minimal MHC class II-binding sequence of the T cell epitope.

Particularly preferred sequences comprise at least one cysteine residue. The skilled person will appreciate that any peptide that contains a single cysteine residue may form dimers, either with itself, or with other cysteine containing peptides with which it may be contacted. Peptides that contain two or more cysteines have the potential to form long chains which may then aggregate. Such dimer/aggregate formation leads to the risk of IgE or IgG binding and thus having a local inflammatory response. Accordingly, a preferred region of the invention typically derives from a protein with a high proportion of cysteine residues. For example, the region of the invention may derive from a protein having greater than 20, 21, 22, 23, 24, 25, 26, 27, 28, 29, 30, 31, 32, 33, 34 or 35% cysteine residues as a proportion of the total number of amino acid residues in the protein. The region of the invention is preferably selected from a sequence within such a protein that has a lower proportion of cysteine residues. Accordingly, the region may comprise upto a maximum of 5, 6, 7, 8, 9, 10, 11, 12, 13, 14, 15, 16, 17, 18, 19 or 20% cysteine residues as a proportion of the total number of amino acid residues in the region. The cysteine residues may be comprised in the minimal MHC Class II-binding sequence of the epitope, or may be comprised in the residues which flank this sequence.

Other sequences prone to dimer formation may be identified by in silico analysis using suitable computational methods, or by in vitro analysis using suitable laboratory methods which quantify the proportion of a sequence which is present in monomeric or dimeric form as set out below. For a sequence that is prone to dimerisation the proportion of sequence present as a dimer may be minimal, i.e. less than about 0.5% or 1% in the solid state, but this will typically increase over time to at least about 0.5%, 1%, 2%, 3%, 4%, 5%, 6%, 7%, 8%, 9%, 10%, 20%, 30%, 40%, 50%, 60%, 70%, 80% or 90% for material stored in solution for a suitable period of time under suitable conditions. Suitable periods of time and conditions include ranges of time and conditions under which a skilled practitioner might reasonably expect to keep a sequence in solution prior to use. For example, periods of time of about 24 hours, about 48 hours, or about 72 hours are typical, although some solutions may be kept for longer periods for example, at least a week, a month, 6 months, 1 year, 2 years, 3 years or more. Storage conditions may typically be room temperature and relative humidity, or typically 25° C. and 60% relative humidity, but could include any standard storage conditions encountered by the skilled person, for example approximately 4° C., −20° C., or −80° C.

The sensitivity of the immune system is such that only a small proportion of dimer is considered likely to trigger an undesirable immune response.

For the assessment of the proportion of a sequence present in a given form a suitable method is, for example, analytical gel electrophoresis under non-denaturing conditions. In such a method, a solution of the sequence is run in a polyacrylamide gel, alongside a set of standard molecular weight markers. If the sequence forms dimers, a protein band will be observed in the gel corresponding to a species with a molecular weight approximately twice that calculated for the sum of the amino acids of the sequence. (Similarly, any trimers or tetramers present will be observed as bands corresponding to species with molecular weights approximately three or four times that calculated for the sum of the residue weights of an amino acids of the sequence). Since it is rare that 100% of a sequence is present in oligomeric form, a second band may also be observed corresponding to a species with approximately the molecular weight calculated for the sum of the amino acids of the sequence—this represents the sequence in monomeric form. The relative intensities of the bands may be used to quantify the proportion of the sequence which is present in each form. Similar methods may assess molecular weight by alternative means, for example, analytical centrifugation, mass spectrometry or size exclusion chromatography. Alternatively, oligomers may be quantified using reverse phase high performance liquid chromatography (RP-HPLC) where the dimers and higher oligomeric species are separated from the monomers based on differences in their hydrophobicities. Identification of the species is achieved using mass spectrometric detection. The same methods may be adapted to assess whether a given peptide shows a tendency to heterodimerise with any other peptide or molecule.

Additionally, the region of the invention may have a solubility of less than 3.5 mg/ml in aqueous solution at pH 2.0 to 12.0, or pH 2.0 to 11.0, pH 2.0 to 10.0, pH 2.0 to 9.0, pH 2.0 to 8.0 or pH 2.0 to 7.0; and/or comprise 1, 2, 3 or 4 cysteine residues; and/or have an isoelectric point lower than 4.5; and/or have a GRAVY score above +0.25. These parameters may be assessed by any suitable method. For example, solubility may be assessed by standard in vitro methods, GRAVY and isoelectric point may be assessed in silico using suitable computational methods, such as the ProtParam tool (Gasteiger E. et al pp. 571-607 The Proteomics Protocols Handbook, Humana Press (2005); John M. Walker (ed)) which is available at http://www.expasy.ch/tools/protparam.html.

Peptides

The peptide of the invention may comprise or consist of the native sequence of the region as defined above or may comprise or consist of the native sequence of the region engineered to reduce dimer formation. The region is engineered by the modification of its native sequence. Particularly preferred modifications are wherein:

at least one cysteine residue in the native sequence of the region is replaced with serine, 2-aminobutyric acid, alanine or glycine; and/or at least one cysteine residue in the native sequence of the region is cysteinylated to create a cystine residue; and/or The residue or residues which are modified may be comprised in any part of the sequence of the region. In one embodiment the residue or residues which are modified are not comprised in the minimal MHC class II-binding sequence of the region. In a preferred embodiment, the modification does not create a new epitope or affect the MHC class II-binding properties of the region.

The peptide of the invention typically contains from 9 to 25 amino acids, and may contain 10, 11, 12, 13, 14, 15, 16, 17, 18, 19, 20, 21, 22, 23 or 24 amino acids. It will be appreciated that the peptide of the invention may consist entirely of the region as defined above, or may comprise additional amino acids flanking the region up to a maximum of 25 amino acids, provided that the additional amino acids do not promote dimer formation. Additional amino acids which promote dimer formation may be assessed by the methods described in the "regions" section above.

Peptides longer than 25 amino acids are likely to possess sufficient tertiary structure to cross-link IgG or IgE on cell surfaces resulting in undesirable immune responses such as B cell activation or mast cell degranulation.

Peptide Synthesis

The peptides of the invention are derived in an intellectual sense from the polypeptide which comprises the region as defined above. This is done by making use of the amino acid sequence of the region and synthesising peptides based on the sequence. Peptides may be synthesised using methods well known in the art. Preferred methods include solid-phase peptide synthesis techniques and most preferably an automated or semiautomated peptide synthesizer. Typically, using such techniques, an $\alpha$-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropyl-ethylamine. The $\alpha$-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, and include t-butyloxycarbonyl (tBoc) and fluorenylmethoxycarbonyl (Fmoc).

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—$NH_2$→—NH(Me) or —N(Me)$_2$).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

Compositions

The composition of the invention typically comprises:
a) i) at least one peptide, wherein the peptide comprises the native sequence of a region as defined above; and
   ii) at least one agent which inhibits dimer formation;
or
b) i) at least one peptide, wherein the peptide comprises a region as defined above which has been engineered as defined above to reduce dimer formation; and optionally
   ii) at least one agent which inhibits dimer formation,
wherein a minimal proportion of the peptide is present in solution as a dimer.

Agents suitable for inhibiting dimer formation include agents suitable for reducing a disulfide bond, antioxidant agents or preservative agents. Suitable reducing agents include any trialkylphosphine compound, including tris(2-carboxyethyl)phosphine (TCEP), 2-Mercaptoethanol and dithiothreitol (DTT). Other suitable agents include thioglycerol, thioanisole, glutathione and cysteine. Particularly preferred compositions of the invention comprise 0.5% thioglycerol or 0.5% thioanisole.

The agent suitable for inhibiting dimer formation may be an agent which promotes cysteinylation of cysteine residues, such as cysteine, particularly cysteine hydrocholoride. The agent suitable for inhibiting dimer formation may be temporarily added to the composition and then removed. In one such embodiment, the agent is an agent which eliminates or reduces the presence of oxidising agents in a composition, since disulfide bond formation is dependent on the presence of oxidising agents. Preferred agents of this type are nitrogen, argon or other inert gases, which may be pulsed through the composition.

An example of a suitable composition of the invention comprises:

| Component | Function | Concentration in formulation mixture | Nominal quantity per batch (400 g) |
|---|---|---|---|
| peptide, acetate-, HCL-, ammonium- or TFA-salt | Active ingredient | 1.4 mM | Variable, dependent upon assay and purity |
| Potassium dihydrogen phosphate | Buffer component | 0.357 g | |
| Concentrated phosphoric acid | Buffer component | 10 mM | 0.159 g |
| 1-Thioglycerol | Reducing agent | 0.5% w/w | 2.0 g |
| D-Mannitol | Tonicity agent | 210 mM | 15.305 g |
| Sterile WFI | Vehicle | N/A | to 400 g |

The above values are based on a typical 400 g batch comprising at least one peptide.

By a minimal proportion of peptide present in solution as a dimer it is meant that a maximum of 5%, 4%, 3%, 2% or 1% is present in solution as a dimer. It will be understood that the proportion of peptide present as a dimer in solution will be the proportion present as a dimer following a suitable period of time in solution. Suitable periods of time include ranges of time that a skilled practitioner might reasonably expect to keep a sequence in solution prior to use. For example, about 24 hours, about 48 hours, or about 72 hours. The proportion of a peptide present in a given form may be assessed by any suitable method as described in the "Regions" section above.

Where the epitope derives from an allergen, the compositions of the invention are typically capable of inducing a late phase response in an individual that is sensitised to the allergen. The term "late phase response" includes the meaning as set forth in Allergy and Allergic Diseases (1997) A. B. Kay (Ed.), Blackwell Science, pp 1113-1130. The late phase response may be any late phase response (LPR). Preferably, the compositions comprising an epitope derived from a protein allergen are capable of inducing a late asthmatic response (LAR) or a late rhinitic response, or a late phase skin response or a late phase ocular response. Whether or not a particular composition can give rise to a LPR can be determined using methods well known in the art; a particularly preferred method is that described in Cromwell O, Durham S R, Shaw R J, Mackay J and Kay A B. Provocation tests and measurements of mediators from mast cells and basophils in asthma and allergic rhinitis. In: Handbook of Experimental Immunology (4) Chapter 127, Editor: Weir D M, Blackwell Scientific Publications, 1986. Thus, preferably, the individual compositions of the invention are able to induce a LPR in an individual who has been sensitised to the protein allergen from which the epitope derives.

Whether or not an individual has been sensitised to the protein from which the epitope derives may be determined by well known procedures such as the detection of antibodies in the individual's blood or serum which are specific for the protein. Where the epitope derives from an allergen, suitable tests for sensitisation to the allergen include skin prick testing with solutions of protein extracts, induction of cutaneous LPRs, clinical history, allergen challenge and radioallergosorbent test (RAST) for measurement of protein specific IgE. Whether or not a particular individual is expected to benefit from treatment may be determined by the physician based, for example, on such tests or determinations.

Desensitising or tolerising an individual to the protein from which the epitope derives means inhibition or dampening of immunological tissue reactions induced by said protein in appropriately sensitised individuals. It has been shown that T cells can be selectively activated, and then rendered unresponsive. Moreover the anergising or elimination of these T-cells leads to desensitisation of the patient for a particular protein. The desensitisation manifests itself as a reduction in response to a protein or protein-derived peptide, or preferably an elimination of such a response, on second and further administrations of the protein or protein-derived peptide. The second administration may be made after a suitable period of time has elapsed to allow desensitisation to occur; this is preferably any period between one day and several weeks. An interval of around two weeks is preferred.

Although the compositions of the invention are able to induce a LPR in an individual who has been sensitised to the protein, it should be appreciated that when a composition is used to treat a patient it is preferable that a sufficiently low concentration of the composition is used such that no observable LPR will occur but the response will be sufficient to partially desensitise the T cells such that the next (preferably higher) dose may be given, and so on. In this way the dose is built up to give full desensitisation but often without ever inducing a LPR in the patient. Although, the composition or peptide is able to do so at a higher concentration than is administered.

The composition of the invention typically has a reduced ability to provoke an early phase response in an individual. By "reduced ability to provoke an early phase response", it will be understood that the composition of the invention will result in a lower severity of early phase symptoms (such as basophil or mast cell degranulation) relative to a composition comprising a peptide comprising the same region as that in the composition of the invention, but without modification of its sequence to reduce dimer formation, and lacking an agent which reduces dimer formation. Accordingly, the composition of the invention will produce a lesser early phase response than an equivalent peptide predominantly present in dimeric form. The peptide is equivalent because it comprises the same MHC Class II-binding T cell epitope.

Alternatively or additionally, the composition of the invention typically has an improved ability to induce tolerance in an individual. By "improved ability to induce tolerance", it will be understood that the composition of the invention will produce a greater level of desensitisation in an individual than a composition comprising a peptide comprising the same region as that in the composition of the invention, but without modification of its sequence to reduce dimer formation, and lacking an agent which reduces dimer formation. Accordingly, the composition of the invention will produce a greater level of desensitisation than an equivalent peptide predominantly present in dimeric form. The peptide is equivalent because it comprises the same MHC Class II-binding T cell epitope.

Desensitisation is as defined above, and its level may be characterised by any suitable means. For example, in allergic asthma, a smaller LAR produced in response to inhalation of the protein from which the epitope derives (or a protein-derived peptide) would indicate a greater level of desensitisation following treatment with the composition of the invention. The size of a LAR can be assessed by any suitable means in the art, for example, detection of the reduction in Forced Expired Volume (FEV) of an individual post-administration of protein. A greater reduction in FEV indicates a larger LAR. The composition of the invention preferably results in an LAR at least 10%, 20%, 30%, 40% or 50% smaller than a composition comprising an equivalent peptide predominantly present in dimeric form.

Alternatively, a greater level of desensitisation may be indicated by a greater reduction in the protein-specific production by T cells of inflammatory cytokines such as interferon gamma, interleukin 4 and interleukin 13. Cytokine production by T cells may be detected by any suitable method, for example an ELISA, ELISPOT assay or flow cytometric assay. Particularly preferred methods include Multiplex bead array assays as described in, for example de Jager et al; Clinical and Diagnostic Laboratory Immunology, 2003, Vol 10(1) p. 133-139. By "a greater reduction", it is preferred that treatment with the composition of the invention will result in the production of preferably at least 10%, 20%, 30%, 40% or 50% less inflammatory cytokines than a composition comprising an equivalent peptide predominantly present in dimeric form.

Preferred compositions of the invention comprise at least one peptide comprising or consisting of the sequence corresponding to any one of SEQ ID NOS: 1 to 71 and optionally thioglycerol. Particularly preferred compositions comprise at least a first and a second peptide, wherein the first and second peptide each comprise or consist of a different sequence selected from the sequences of SEQ ID NO: 37 (MLA01), SEQ ID NO: 38 (MLA04), SEQ ID NO: 39 (MLA05), or SEQ ID NO: 40 (MLA12). For example, the first and second peptide may comprise or consist of the sequences of a) SEQ ID NOS: 37 (MLA01) and 38 (MLA04); b) SEQ ID NOS: 37 (MLA01) and 39 (MLA05); c) SEQ ID NOS: 37 (MLA01) and 40 (MLA12); d) SEQ ID NOS: 38 (MLA04) and 39 (MLA05); e) SEQ ID NOS: 38 (MLA04) and 40 (MLA12); or f) SEQ ID NOS: 39 (MLA05) and 40 (MLA12), respectively.

Polynucleotides, Vectors and Cells

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the peptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a peptide of the invention.

The present invention thus includes expression vectors that comprise such polynucleotide sequences. Thus, the present invention provides a vector for use in preventing or treating allergy by tolerisation comprising one or more polynucleotide sequences which encode different polypeptides of the invention and optionally one or more further polynucleotide sequences which encode different polypeptides as defined herein.

Furthermore, it will be appreciated that the compositions and products of the invention may comprise a mixture of polypeptides and polynucleotides. Accordingly, the invention provides a composition or product as defined herein, wherein in place of any one of the polypeptide is a polynucleotide capable of expressing said polypeptide.

Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

Alternatively, polynucleotides of the invention may be expressed in a suitable manner to allow presentation of a peptide of the invention by an MHC class II molecule at the surface of an antigen presenting cell. For example, a polynucleotide, expression cassette or vector of the invention may be targeted to antigen presenting cells, or the expression of encoded peptide may be preferentially stimulated or induced in such cells.

Polynucleotides of interest may be used in vitro, ex vivo or in vivo in the production of a peptide of the invention. Such polynucleotides may be administered or used in the prevention or treatment of allergy to cats by tolerisation.

Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery, inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

The polypeptides, polynucleotides, vectors or cells of the invention may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins, polynucleotides, cells or dry mass of the preparation.

Formulations

The peptides, polynucleotides, vectors and cells of the invention may be provided to an individual either singly or in combination. Each molecule or cell of the invention may be provided to an individual in an isolated, substantially isolated, purified or substantially purified form. For example, a peptide of the invention may be provided to an individual substantially free from the other peptides.

Whilst it may be possible for the peptides, polynucleotides or compositions according to the invention to be presented in raw form, it is preferable to present them as a pharmaceutical formulation. Thus, according to a further aspect of the invention, the present invention provides a pharmaceutical formulation for tolerising an individual to a protein from which a peptide of the invention derives, comprising a composition, vector or product according to the invention together with one or more pharmaceutically acceptable carriers or diluents and optionally one or more other therapeutic ingredients. The carrier (s) must be 'acceptable' in the sense of being compatible with the other ingredients of the formulation (in particular they must not promote dimer formation) and not deleterious to the recipient thereof. Typically, carriers for injection, and the final formulation, are sterile and pyrogen free.

For example, compositions containing one or more molecules or cells of the invention can be combined with one or more pharmaceutically acceptable excipients or vehicles. Auxiliary substances, such as wetting or emulsifying agents, pH buffering substances, antioxidants, chelating agents and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution solution or a powder for reconstitution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as an aqueous solution (including water) or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the peptides or polynucleotides of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules and genetically engineered polymers such as silk-elastin like polymers (Ghandehari and Cappello (1998) Pharm. Res. 15: 813-815).

Also, the peptides may be formulated at high concentrations >100 nmol/mL with dimethyl sulphoxide, polyethylene oxide, polyethylene glycol or other suitable excipients for use with implantable drug delivery devices.

The formulation of any of the peptides, polynucleotides or cells mentioned herein will depend upon factors such as the nature of the substance and the method of delivery. Any such substance may be administered in a variety of dosage forms. It may be administered orally (e.g. as tablets, troches, lozenges, aqueous or oily suspensions, dispersible powders or granules), parenterally, subcutaneously, by inhalation, intravenously, intramuscularly, intrasternally, transdermally, intradermally, sublingually, instranasally, buccally or by infusion techniques. The substance may also be administered as suppositories. A physician will be able to determine the required route of administration for each particular individual.

The compositions of formulations of the invention will comprise a suitable concentration of each peptide/polynucleotide/cell to be effective without causing adverse reaction. Typically, the concentration of each peptide in the composition will be in the range of 0.03 to 200 nmol/ml. More preferably in the range of 0.3 to 200 nmol/ml, 3 to 180 nmol/ml, 10 to 150 nmol/ml or 30 to 120 nmol/ml. The composition or formulations should have a purity of greater than 95% or 98% or a purity of at least 99%.

A composition may therefore be formulated which comprises a molecule and/or cell of the invention and also one or more other therapeutic molecules. A composition of the invention may alternatively be used simultaneously, sequentially or separately with one or more other therapeutic compositions as part of a combined treatment.

Therapeutic Methods and Individual to be Treated

The present invention relates to compositions comprising peptides that are capable of desensitising or tolerising human individuals to proteins from which the peptides of the invention derive. Such proteins are typically allergens or other antigens to which an immune response is undesirable. Examples of such antigens include antigens associated with autoimmune diseases, antigens associated with graft-versus-host disease or transplant rejection (herein referred to as alloimmune conditions) and antigens associated with maternal-foetal immune responses, for example Rhesus D Haemolytic Disease of the Newborn. The compositions of the invention are therefore useful in the prevention or treatment an allergic disease, an autoimmune disease, an alloimmune condition or a maternal-foetal immune response. The invention provides compositions, products, vectors and formulations for use in preventing or treating the above conditions. The invention also provides a method of preventing or treating a subject having the above conditions, comprising administering, either singly or in combination the polypeptides/polynucleotides/cells of the invention as described above.

The individual to be treated or provided with the composition or formulation of the invention is preferably human. It will be appreciated that the individual to be treated may be known to be sensitised to the particular allergen or antigen, at risk of being sensitised or suspected of being sensitised. The individual can be tested for sensitisation using techniques well known in the art and as described herein. Alternatively, the individual may have a family history of the conditions described above. It may not be necessary to test an individual for sensitisation to allergens because the individual may display symptoms of allergy when brought into proximity to a suitable allergen source. By proximity is meant 10 metres or less, 5 metres or less, 2 metres or less, 1 metre or less, or 0 metres from the source. Symptoms of allergy can include itchy eyes, runny nose, breathing difficulties, red itchy skin or rash. The individual to be treated may be of any age. However, preferably, the individual may be in the age group of 1 to 90, 5 to 60, 10 to 40, or more preferably 18 to 35. Preferably, the individual to be treated is from a population that has MHC allele frequencies within the range of frequencies that are representative of the Caucasian population. Reference population allele frequencies for 11 common DRB1 allele families are shown in Table 1 (Data from HLA Facts Book, Parham and Barber).

TABLE 1

| | DRB1 | | | | | | | | | | |
|---|---|---|---|---|---|---|---|---|---|---|---|
| | 1 | 3 | 4 | 7 | 8 | 11 | 12 | 13 | 14 | 15 | 16 |
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MEC allele frequencies as the reference population for the alleles referred to Table 1 (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:
4—at least 9%
7—at least 10%
11—at least 8%.

The individual to be treated for allergic disease may have had allergy for at least 2 weeks, 1 month, 6 months, 1 year or 5 years. The individual may suffer from a rash, nasal congestion, nasal discharge and/or coughing caused by the allergy. The individual may or may not have been administered with other compositions/compounds which treat allergy.

The invention is particularly suitable for use with individuals who may need to receive multiple administrations of the compositions of the invention as described above. Peptides which are more prone to dimer formation than the peptides of the invention are more likely to induce an adverse response in an individual receiving multiple administrations. Since monomeric peptides are less immunogenic than dimeric peptides, the invention is also particularly suitable for administration to an individual who has or is at risk of a condition, wherein the condition is characterised by an adverse inflammatory reaction to a treatment comprising a peptide. An adverse inflammatory reaction to a treatment comprising a peptide may be diagnosed as a result of the onset of any of the symptoms of allergy as defined above following administration of a treatment comprising a peptide. An individual may be considered to be at risk of such a reaction for any suitable medical reason, for example, a family history of similar reactions, a personal medical history of multiple allergic responses, or strongly positive skin prick or skin patch responses to common allergens.

Allergens and Antigens

Suitable allergens from which the region containing a MHC Class II-binding T cell epitope may derive can of course be obtained and/or produced using known methods. Classes of suitable allergens include, but are not limited to, pollens, animal dander (in particular cat dander), grasses, molds, dusts, antibiotics, stinging insect venoms, and a variety of environmental (including chemicals and metals), drug and food allergens. Common tree allergens include pollens from cottonwood, poplar, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Candida, Alternaria, Fusarium, Hormodendrum, Aspergillus, Micropolyspora, Mucor* and thermophilic actinomycetes; epidermal allergens can be obtained from house or organic dusts (typically fungal in origin), from arthropods such as house mites (*Dermatophagoides pteronyssinus*), or from animal sources such as feathers, and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major allergen produced by the domestic cat *Felis catus* (*Felis domesticus*) glycoprotein Fel d1, the major and cryptic epitopes of the Der p I allergen (Hoyne et al. (1994) *Immunology* 83190-195), bee venom phospholipase A2 (PLA) (Akdis et al. (1996) *J. Clin. Invest.* 98:1676-1683), birch pollen allergen Bet v 1 (Bauer et al. (1997) *Clin. Exp. Immunol.* 107:536-541), and the multi-epitopic recombinant grass allergen rKBG8.3 (Cao et al. (1997) *Immunology* 90:46-51). These and other suitable allergens are commercially available and/or can be readily prepared as extracts following known techniques.

Preferably, the allergen is selected from the list of allergen sequences and database accession numbers (NCBI Entrez accession numbers) below. NCBI is the National Center for Biotechnology information and is a division of the US National Institutes of Health. The NCBI web site, from which access to the database may be sought, is www.ncbi.nlm.nih.gov/. Allergen sequences and database accession numbers (NCBI Entrez accession numbers):

House Dust Mite

*Dermatophagoides pteronyssinus*
Der p 1
MKIVLAIASLLALSAVYARPSSIKTFEEYKKAFNKSYATFEDEEAARK

NFLESVKYVQSNGGAINHLSDLSLDEFKNRFLMSAEAFEHLKTQFD

LNAETNACSINGNAPAEIDLRQMRTVTPIRMQGGCGSCWAFSGVAA

TESAYLAYRNQSLDLAEQELVDCASQHGCHGDTIPRGIEYIQHNGV

VQESYYRYVAREQSCRRPNAQRFGISNYCQIYPPNVNKIREALAQT

HSAIAVIIGIKDLDAFRHYDGRTIIQRDNGYQPNYHAVNIVGYSNAQG

VDYWIVRNSWDTNWGDNGYGYFAANIDLMMIEEYPYVVIL

Der p 2
MMYKILCLSLLVAAVARDQVDVKDCANHEIKKVLVPGCHGSEPC

IIHRGKPFQLEAVFEANQNTKTAKIEIKASIDGLEVDVPGIDPNAC

HYMKCPLVKGQQYDIKYTWNVPKIAPKSENVVVTVKVMGDDGV

LACAIATHAKIRD

Der p 3
MIIYNILIVLLLAINTLANPILPASPNATIVGGEKALAGECPYQISLQS

SSHFCGGTILDEYWILTAAHCVAGQTASKLSIRYNSLKHSLGGEK

ISVAKIFAHEKYDSYQIDNDIALIKLKSPMKLNQKNAKAVGLPAK

GSDVKVGDQVRVSGWGYLEEGSYSLPSELRRVDIAVVSRKE

CNELYSKANAEVTDNMICGGDVANGGKDSCQGDSGGPVVD

VKNNQVVGIVSWGYGCARKGYPGVYTRVGNFIDWIESKRSQ

Der p 4
KYXNPHFIGXRSVITXLME

Der p 5
MKFIIAFFVATLAVMTVSGEDKKHDYQNEFDFLLMERIHEQIKK

GELALFYLQEQINHFEEKPTKEMKDKIVAEMDTIIAMIDGVRG

VLDRLMQRKDLDIFEQYNLEMAKKSGDILERDLKKEEARVK

KIEV

Der p 6
AIGXQPAAEAEAPFQISLMK

Der p 7
MMKLLLIAAAAFVAVSADPIHYDKITEEINKAVDEAVAAIEKS

ETFDPMKVPDHSDKFERHIGIIDLKGELDMRNIQVRGLKQM

KRVGDANVKSEDGVVKAHLLVGVHDDVVSMEYDLAYKLG

DLHPNTHVISDIQDFVVELSLEVSEEGNMTLTSFEVRQFANV

VNHIGGLSILDPIFAVLSDVLTAIFQDTVRAEMTKVLAPAFK

KELERNNQ

Der p9
IVGGSNASPGDAVYQIAL

*Dermatophagoides farinae*
Der f 1
MKFVLAIASLLVLTVYARPASIKTFEFKKAFNKNYATVEEEE

VARKNFLESLKYVEANKGAINHLSDLSLDEFKNRYLMSAEAF

EQLKTQFDLNAETSACRINSVNVPSELDLRSLRTVTPIRMQG

GCGSCWAFSGVAATESAYLAYRNTSLDLSEQELVDCASQH

GCHGDTIPRGIEYIQQNGVVEERSYPYVAREQRCRRPNSQHY

GISNYCQIYPPDVKQIREALTQTHTAIAVIIGIKDLRAFQHYDGR

TIIQHDNGYQPNYHAVNIVGYGSTQGDDYWIVRNSWDTTW

GDSGYGYFQAGNNLMMIEQYPYVVIM

Der f 2
MISKILCLSLLVAAVVADQVDVKDCANNEIKKVMVDGCHGS

DPCIIHRGKPFTLEALFDANQNTKTAKIEIKASLDGLEIDVPGI

DTNACHFMKCPLVKGQQYDIKYTWNVPKIAPKSENVVVTV

KLIGDNGVLACAIATHGKIRD

Der f 3
MMILTIVVLLAANILATPILPSSPNATIVGGVKAQAGDCPYQI

SLQSSSHFCGGSILDEYWILTAAHCVNGQSAKKLSIRYNTL

KHASGGEKIQVAEIYQHENYDSMTIDNDVALIKLKTPMTLD

QTNAKPVPLPAQGSDVKVGDKIRVSGWGYLQEGSYSLP

SELQRVDIDVVSREQCDQLYSKAGADVSENMICGGDVA

NGGVDSCQGDSGGPVVDVATKQIVGIVSWGYGCARKG

YPGVYTRVGNFVDWIESKRSQ

Der f 4
AVGGQDADLAEAPFQISLLK

Der f 7
MMKFLLIAAVAFVAVSADPIHYDKITEEINKAIDDAIAAIEQ

SETIDPMKVPDHADKFERHVGIVDFKGELAMRNIEARGL

KQMKRQGDANVKGEEGIVKAHLLIGVHDDIVSMEYDLAY

KLGDLHPTTHVISDIQDFVVALSLEISDEGNITMTSFEVRQ

FANVVNHIGGLSILDPIFGVLSDVLTAIFQDTVRKEMTKVL

APAFKRELEKN

Additional mite allergen sequences (NCBI entrez accession):
1170095; 1359436; 2440053; 666007; 487661; 1545803; 84702; 84699; 625532; 404370; 1091577; 1460058; 7413; 9072; 387592.

Cat

*Felis* sequences (NCBI entrez accession):
39716; 539715; 423193; 423192; 423191; 423190; 1364213; 1364212; 395407; 163827; 163823; 163825; 1169665; 232086; 1169666.

Latex

Hevea Sequences:

Hev b 1
MAEDEDNQQGQGEGLKYLGFVQDAATYAVTTFSNVYLFAKDKSGPLQP

GVDIIEGPVKNVAVPLYNRFSYIPNGALKFVDSTVVASVTIIDRSLPP

IVKDASIQVVSAIRAAPEAARSLASSLPGQTKILAKVFYGEN

Hev b 3
MAEEVEEERLKYLDFVRAAGVYAVDSFSTLYLYAKDISGPLKPGVDTIE

NVVKTVVTPVYYIPLEAVKFVDKTVDVSVTSLDGVVPPVIKQVSAQTYS

-continued

```
VAQDAPRIVLDVASSVFNTGVQEGAKALYANLEPKAEQYAVITWRALN

KLPLVPQVANVVVPTAVYFSEKYNDVVRGTTEQGYRVSSYLPLLPTEK

ITKVFGDEAS
```

Additional Hevea sequences (NCBI entrez accession):
3319923; 3319921; 3087805; 1493836; 1480457; 1223884; 3452147; 3451147; 1916805; 232267; 123335; 2501578; 3319662; 3288200; 1942537; 2392631; 2392630; 1421554; 1311006; 494093; 3183706; 3172534; 283243; 1170248; 1708278; 1706547; 464775; 2661042; 231586; 123337; 116359; 123062; 2213877; 542013; 2144920; 1070656; 2129914; 2129913; 2129912; 100135; 82026; 1076559; 82028; 82027; 282933; 280399; 100138; 1086972; 108697; 1086976; 1086978; 1086978; 1086976; 1086974; 1086972; 913758; 913757; 913756; 234388; 1092500; 228691; 1177405; 18839; 18837; 18835; 18833; 18831; 1209317; 1184668; 168217; 168215; 168213; 168211; 168209; 348137.

Rye Grass
*Lolium* Sequences:

```
126385 Lol p 1
MASSSSVLLVVALFAVFLGSAHGIAKVPPGPNITAEYGDKWLDAKSTWYGK

PTGAGPKDNGGACGYKNVDKAPFNGMTGCGNTPIFKDGRGCGSCFEIKCTK

PESCSGEAVTVTITDDNEEPIAPYHFDLSGHAFGSMAKKGEEQNVRSAGELE

LQFRRVKCKYPDDTKPTFHVEKASNPNYLAILVKYVDGDGDVVAVDIKEKGKDK

WIELKESWGAVWRIDTPDKLTGPFTVRYTTEGGTKSEFEDVIPEGWKADTSYSAK

126386 Lol p 2a
AAPVEFTVEKGSDEKNLALSIKYNKEGDSMAEVELKEHGSNEWLALKKNG

DGVWEIKSDKPLKGPFNFRFVSEKGMRNVFDDVVPADFKVGTTYKPE

126387 Lol p 3
TKVDLTVEKGSDAKTLVLNIKYTRPGDTLAEVELRQHGSEEWEPMTKKGNLWEVKSA

KPLTGPMNFRFLSKGGMKNVFDEVIPTAFTVGKTYTPEYN

2498581 Lol p 5a
MAVQKYTVALFLRRGPRGGPGRSYAADAGYTPAAAATPATPAATPAGGWR

AKAEGDDRRAEAAGGRQRLASRQPWPPLPTPLRRTSSRSSRPPSPSPPRASSPTSAPGL

IPKLDTAYDVAYKAAEAHPRGQVRRLRHCPHRSLRVIAGALEVHAVKPATEEVL

AAKIPTGELQIVDKIDAAFKIAATAANAAPTNDKFTVFESAFNKALNECTGGAM

RPTSSSPPSRPRSSRPTPPPSPAAPEVKYAVFEAALTKAITAMTQAQKAGKPAAAAA

TAAATVATAAATAAAVLPPPLLVVQSLISLLIYY

2498582 Lol p 5b
MAVQKHTVALFLAVALVAGPAASYAADAGYAPATPATPAAPATAATPATP

ATPATPAAVPSGKATTEEQKLIEKINAGFKAAVAAAAVVPPADKYKTFVETF

GTATNKAFVEGLASGYADQSKNQLTSKLDAALKLAYEAAQGATPEAKYDA

YVATLTEALRVIAGTLEVHAVKPAAEEVKVGAIPAAEVQLIDKVDAAYRTA

ATAANAAPANDKFTVFENTFNNAIKVSLGAAYDSYKFIPTLVAAVKQAYAAKQ

ATAPEVKYTVSETALKKAVTAMSEAEKEATPAAAATATPTPAAATATATPAAA

YATATPAAATATATPAAATATPAAAGGYKV

455288 Lol p isoform 9
MAVQKHTVALFLAVALVAGPAASYAADAGYAPATPATPAAPATAATPATP

ATPATPAAVPSGKATTEEQKLIEKINAGFKAAVAAAAVVPPADKYKTFVETF

GTATNKAFVEGLASGYADQSKNQLTSKLDAALKLAYEAAQGATPEAKYDA

YVATLTEALRVIAGTLEVHAVKPAAEEVKVGAIPAAEVQLIDKVDAAYRTAATA

ANAAPANDKFTVFENTFNNAIKVSLGAAYDSYKFIPTLVAAVKQAYAAKQATAPEVK

YTVSETALKKAVTAMSEAEKEATPAAAATATPTPAAATATATPAAAYA

TATPAAATATATPAAATATPAAAGGYKV

1582249 Lol p 11
DKGPGFVVTGRVYCDPCRAGFETNVSHNVEGATVAVDCRPFDGGESKLKAEATTD
```

KDGWYKIEIDQDHQEEICEVVLAKSPDKSCSEIEEFRDRARVPLTSNXGIKQQGIR

YANPIAFFRKEPLKECGGILQAY

Additional *Lolium* sequences (NCBI entrez accession):
135480; 417103; 687261; 687259; 1771355; 2388662; 631955; 542131; 542130; 542129; 100636; 626029; 542132; 320616; 320615; 320614; 100638; 100634; 82450; 626028; 100639; 283345; 542133; 1771353; 1763163; 1040877; 1040875; 250525; 551047; 515377; 510911; 939932; 439950; 2718; 168316; 168314; 485371; 2388664; 2832717; 2828273; 548867.

Olive Tree
Olive sequences

416610 Ole e 1
EDIPQPPVSQFHIQGQVYCDTCRAGFITELSEFIPGASLRLQCKDKEN

GDVTFTEVGYTRAEGLYSMLVERDHKNEFCEITLISSGRKDCNEIPTE

GWAKPSLKFKLNTVNGTTRTVNPLGFFKKEALPKCAQVYNKLGMYP

PNM

*Parietaria*
*Parietaria* Sequences:

2497750 Par j P2
MRTVSMAALVVIAAALAWTSSAEPAPAPAPGEEACGKVVQDIMPCL

HFVKGEEKEPSKECCSGTKKLSEEVKTTEQKREACKCIVRATKGISG

IKNELVAEVPKKCDIKTTLPPITADFDCSKIQSTIFRGYY

1352506 Par j P5
MVRALMPCLPFVQGKEKEPSKGCCSGAKRLDGETKTGPQRVHACEC

IQTAMKTYSDIDGKLVSEVPKHCGIVDSKLPPIDVNMDCKTVGVVPRQP

QLPVSLRHGPVTGPSDPAHKARLERPQIRVPPPAPEKA

1532056 Par j P8
MRTVSMAALVVIAAALAWTSSAELASAPAPGEGPCGKVVHHIMPCLK

FVKGEEKEPSKSCCSGTKKLSEEVKTTEQKREACKCIVAATKGISGIK

NELVAEVPKKCGITTTLPPITADFDCSKIESTIFRGYY

1532058 Par j P9
MRTVSAPSAVALVVIVAAGLAWTSLASVAPPAPAPGSEETCGTVVR

ALMPCLPFVQGKEKEPSKGCCSGAKRLDGETKTGLQRVHACECIQ

TAMKTYSDIDGKLVSEVPKHCGIVDSKLPPIDVNMDCKTLGVVPRQP

QLPVSLRHGPVTGPSDPAHKARLERPQIRVPPPAPEKA

2497749 Par j P9
MRTVSARSSVALVVIVAAVLVWTSSASVAPAPAPGSEETCGTVVGA

LMPCLPFVQGKEKEPSKGCCSGAKRLDGETKTGPQRVHACECIQTA

MKTYSDIDGKLVSEVPKHCGIVDSKLPPIDVNMDCKTLGVLHYKGN

1086003 Par j 1
MVRALMPCLPFVQGKEKEPSKGCCSGAKRLDGETKTGPQRVHACE

CIQTAMKTYSDIDGKLVSEVPKHCGIVDSKLPPIDVNMDCKTVGVVPR

QPQLPVSLRHGPVTGPSRSRPPTKHGWRDPRLEFRPPHRKKPNPAF

STLG

Additional *Parietaria* sequences (NCBI entrez accession):
43659; 1836011; 1836010; 1311513; 1311512; 1311511; 1311510; 1311509; 240971.

Timothy Grass
*Phleum* Sequences:

Phl p 1
MASSSSVLLVVVLFAVFLGSAYGIPKVPPGPNITATYGDKWLDAKSTWYGKPTGA

GPKDNGGACGYKDVDKPPFSGMTGCGNTPIFKSGRGCGSCFEIKCTKPEACSGEP

VVVHITDDNEEPIAPYHFDLSGHAFGAMAKKGDEQKLRSAGELELQFRRVKCKYPEG

TKVTFHVEKGSNPNYLALLVKYVNGDGDVVAVDIKEKGKDKWIELKESWG

AIWRIDTPDKLTGPFTVRYTTEGGTKTEAEDVIPEGWKA

DTSYESK

Phl p 1
MASSSSVLLVVALFAVFLGSAHGIPKVPPGPNITATYGDKWLDAKSTWYGK

PTAAGPKDNGGACGYKDVDKPPFSGMTGCGNTPIFKSGRGCGSCFEIKCTKP

EACSGEPVVVHITDDNEEPIAAYHFDLSGIAFGSMAKKGDEQKLRSAGEVEI

QFRRVKCKYPEGTKVTFHVEKGSNPNYLALLVKFSGDGDVVAVDIKEKGKD

KWIALKESWGAIWRIDTPEVLKGPFTVRYTTEGGTKARAKDVIPEGWKADT

AYESK

```
Phl p 2
MSMASSSSSSLLAMAVLAALFAGAWCVPKVTFTVEKGSNEKHLAVLVKYEGDTMAEVEL

REHGSDEWVAMTKGEGGVWTFDSEEPLQGPFNFRFLTEKGMKNVFDDVVPE

KYTIGATYAPEE

Phl p 5
ADLGYGGPATPAAPAEAAPAGKATTEEQKLIEKINDGFKAALAAAAGVPPA

DKYKTFVATFGAASNKAFAEGLSAEPKGAAESSSKAALTSKLDAAYKLAYK

TAEGATPEAKYDAYVATLSEALRIIAGTLEVHAVKPAAEEVKVIPAGELQVIE

KVDSAFKVAATAANAAPANDKFTVFEAAFNNAIKASTGGAYESYKFIPALE

AAVKQAYAATVATAPEVKYTVFETALKKAFTAMSEAQKAAKPATEATATA

TAAVGAATGAATAATGGYKV

Phl p 5
ADLGYGGPATPAAPAEAAPAGKATTEEQKLIEKINDGFKAALAAAAGVPPA

DKYKTFVATFGAASNKAFAEGLSAEPKGAAESSSKAALTSKLDAAYKLAYK

TAEGATPEAKYDAYVATLSEALRIIAGTLEVHAVKPAAEEVKVIPAGELQVIE

KVDSAFKVAATAANAAPANDKFTVFEAAFNNAIKASTGGAYESYKFIPALE

AAVKQAYAATVATAPEVKYTVFETALKKAITAMSEAQKAAKPATEATATA

TAAVGAATGAATAATGGYKV

Phl p 5b
AAAAVPRRGPRGGPGRSYTADAGYAPATPAAAGAAAGKATTEEQKLIEDIN

VGFKAAVAAAASVPAADKFKTFEAAFTSSSKAAAAKAPGLVPKLDAAYSV

AYKAAVGATPEAKFDSFVASLTEALRVIAGALEVHAVKPVTEEPGMAKIPA

GELQIIDKIDAAFKVAATAAATAPADDKFTVFEAAFNKAIKESTGGAYDTYK

CIPSLEAAVKQAYAATVAAAPQVKYAVFEAALTKAITAMSEVQKVSQPATG

AATVAAGAATTAAGAASGAATVAAGGYKV

Phl p 5a
ADLGYGPATPAAPAAGYTPATPAAPAGADAAGKATTEEQKLIEKINAGFKA

ALAGAGVQPADKYRTFVATFGPASNKAFAEGLSGEPKGAAESSSKAALTSK

LDAAYKLAYKTAEGATPEAKYDAYVATLSEALRIIAGTLEVHAVKPAAEEV

KVIPAGELQVIEKVDAAFKVAATAANAAPANDKFTVFEAAFNDEIKASTGG

AYESYKFIPALEAAVKQAYAATVATAPEVKYTVFETALKKAITAMSEAQKA

AKPAAAATATATAAVGAATGAATAATGGYKV

Phl p 5
MAVQKYTVALFLAVALVAGPAASYAADAGYAPATPAAAGAEAGKATTEE

QKLIEDINVGFKAAVAAAASVPAADKFKTFEAAFTSSSKAATAKAPGLVPKL

DAAYSVSYKAAVGATPEAKFDSFVASLTEALRVIAGALEVHAVKPVTEEPG

MAKIPAGELQIIDKIDAAFKVAATAAATAPADTVFEAAFNKAIKESTGGAYD

TYKCIPSLEAAVKQAYAATVAAAPQVKYAVFEAALTKAITAMSEVQKVSQP

ATGAATVAAGAATTAAGAASGAATVAAGGYKV

Phl p 5
MAVQKYTVALFLAVALVAGPAASYAADAGYAPATPAAAGAEAGKATTEE

QKLIEDINVGFKAAVAAAASVPAADKFKTFEAAFTSSSKAATAKAPGLVPKL

DAAYSVAYKAAVGATPEAKFDSFVASLTEALRVIAGALEVHAVKPVTEDPA

WPKIPAGELQIIDKIDAAFKVAATAAATAPADDKFTVFEAAFNKAIKESTGG
```

-continued

AYDTYKCIPSLEAAVKQAYAATVAAAPQVKYAVFEAALTKAITAMSEVQK

VSQPATGAATVAAGAATTATGAASGAATVAAGGYKV

Phl p 5
ADAGYAPATPAAAGAEAGKATTEEQKLIEDINVGFKAAVAAAASVPAADKF

KTFEAAFTSSSKAATAKAPGLVPKLDAAYSVAYKAAVGATPEAKFDSFVAS

LTEALRVIAGALEVHAVKPVTEEPGMAKIPAGELQIIDKIDAAFKVAATAAA

TAPADDKFTVFEAAFNKAIKESTGGAYDTYKCIPSLEAAVKQAYAATVAAA

PQVKYAVFEAALTKAITAMSEVQKVSQPATGAATVAAGAATTAAGAASGA

ATVAAGGYKV

Phl p 5
SVKRSNGSAEVHRGAVPRRGPRGGPGRSYAADAGYAPATPAAAGAEAGKA

TTEEQKLIEDINVGFKAAVAAAASVPAADKFKTFEAAFTSSSKAATAKAPGL

VPKLDAAYSVAYKAAVGATPEAKFDSFVASLTEALRVIAGALEVHAVKPVT

EEPGMAKIPAGELQIIDKIDAAFKVAATAAATAPADDKFTVFEAAFNKAIKES

TGGAYDTYKCIPSLEAAVKQAYAATVAAAPQVKYAVFEAALTKAITAMSEV

QKVSQPATGAATVAAGAATTAAGAASGAATVAAGGYKV

Phl p 5
MAVHQYTVALFLAVALVAGPAGSYAADLGYGPATPAAPAAGYTPATPAAP

AGAEPAGKATTEEQKLIEKINAGFKAALAAAAGVPPADKYRTFVATFGAAS

NKAFAEGLSGEPKGAAESSSKAALTSKLDAAYKLAYKTAEGATPEAKYDAY

VATVSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

APEVKYTVFETALKKAITAMSEAQKAAKPAAAATATATAAVGAATGAATA

ATGGYKV

Phl p 5
ADLGYGGPATPAAPAEAAPAGKATTEEQKLIEKINDGFKAALAAAAGVPPADKYKTFVA

TFGAASNKAFAEGLSAEPKGAAESSSKAALTSKLDAAYKLAYKTAEG

ATPEAKYDAYVATLSEALRIIAGTLEVHAVKPAAEEVKVIPAGELQVIEKVDS

AFKVAATAANAAPANDKFTVFEAAFNNAIKASTGGAYESYKFIPALEAAVK

QAYAATVATAPEVKYTVFETALKKAFTAMSEAQKAAKPATEATATATAAVGA

ATGAATAATGGYKV

Phl p5b
AAAAVPRRGPRGGPGRSYTADAGYAPATPAAAGAAAGKATTEEQKLIEDIN

VGFKAAVAAAASVPAADKFKTFEAAFTSSSKAAAAKAPGLVPKLDAAYSV

AYKAAVGATPEAKFDSFVASLTEALRVIAGALEVHAVKPVTEEPGMAKIPA

GELQIIDKIDAAFKVAATAAATAPADDKFTVFEAAFNKAIKESTGGAYDTYK

CIPSLEAAVKQAYAATVAAAPQVKYAVFEAALTKAITAMSEVQKVSQPATG

AATVAAGAATTAAGAASGAATVAAGGYKV

Phl p5a
ADLGYGPATPAAPAAGYTPATPAAPAGADAAGKATTEEQKLIEKINAGFKA

ALAGAGVQPADKYRTFVATFGPASNKAFAEGLSGEPKGAAESSSKAALTSK

LDAAYKLAYKTAEGATPEAKYDAYVATLSEALRIIAGTLEVHAVKPAAEEV

KVIPAGELQVIEKVDAAFKVAATAANAAPANDKFTVFEAAFNDEIKASTGG

-continued

AYESYKFIPALEAAVKQAYAATVATAPEVKYTVFETALKKAITAMSEAQKA

AKPAAAATATATAAVGAATGAATAATGGYKV

Phl p 5
AVPRRGPRGGPGRSYAADAGYAPATPAAAGAEAGKATTEEQKLIEDINVGF

KAAVAAAASVPAGDKFKTFEAAFTSSSKAATAKAPGLVPKLDAAYSVAYK

AAVGATPEAKFDSFVASLTEALRVIAGALEVHAVKPVTEEPGMAKIPAGELQ

IIDKIDAAFKVAATAAATAPADDKFTVFEAAFNKAIKESTGGAYDTYKCIPSL

EAAVKQAYAATVAAAPQVKYAVFEAALTKAITAMSEVQKVSQPATGAATV

AAGAATTATGAASGAATVAAGGYKV

Phl p 5b
MAVPRRGPRGGPGRSYTADAGYAPATPAAAGAAAGKATTEEQKLIEDINVG

FKAAVAARQRPAADKFKTFEAASPRHPRPLRQGAGLVPKLDAAYSVAYKA

AVGATPEAKFDSFVASLTEALRVIAGALEVHAVKPVTEEPGMAKIPAGELQII

DKIDAAFKVAATAAATAPADDKFTVFEAAFNKAIKESTGGAYDTYKCIPSLE

AAVKQAYAATVAAAAEVKYAVFEAALTKAITAMSEVQKVSQPATGAATVA

AGAATTAAGAASGAATVAAGGYKV

Phl p 5
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAAS

NKAFAEGLSGEPKGAAESSSKAALTSKLDAAYKLAYKTAEGATPEAKYDAY

VATLSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

APEVKYTVFETALKKAITAMSEAQKAAKPAAAATATATAAVGAATGAATA

ATGGYKV

Phl p 5
EAPAGKATTEEQKLIEKINAGFKAALARRLQPADKYRTFVATFGPASNKAFA

EGLSGEPKGAAESSSKAALTSKLDAAYKLAYKTAEGATPEAKYDAYVATLS

EALRIIAGTLEVHAVKPAAEEVKVIPAAELQVIEKVDAAFKVAATAANAAPA

NDKFTVFEAAFNDEIKASTGGAYESYKFIPALEAAVKQAYAATVATAPEVK

YTVFETALKKAITAMSEAQKAAKPPPLPPPPQPPPLAATGAATAATGGYKV

Phl p 5
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAAS

NKAFAEGLSGEPKGAAESSSKAALTSKLDAAYKLAYKTAEGATPEAKYDAY

VATLSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

APEVKYTVFETALKKAITAMSEAQKAAKPAAAATATATAAVGAATGAATA

ATGGYKV

Phl p 5b
MAVPRRGPRGGPGRSYTADAGYAPATPAAAGAAAGKATTEEQKLIEDINVG

FKAAVAARQRPAADKFKTFEAASPRHPRPLRQGAGLVPKLDAAYSVAYKAAV

GATPEAKFDSFVASLTEALRVIAGALEVHAVKPVTEEPGMAKIPAGELQIIDKID

-continued

AAFKVAATAAATAPADDKFTVFEAAFNKAIKESTGGAYDTYKCIPSLEAAVKQ

AYAATVAAAAEVKYAVFEAALTKAITAMSEVQKVSQPATGAATVAAGAATTAAGA

ASGAATVAAGGYKV

Phl p 5a
ADLGYGPATPAAPAAGYTPATPAAPAGADAAGKATTEEQKLIEKINAGFKA

ALAGAGVQPADKYRTFVATFGPASNKAFAEGLSGEPKGAAESSSKAALTSK

LDAAYKLAYKTAEGATPEAKYDAYVATLSEALRIIAGTLEVHAVKPAAEEVKVIP

AGELQVIEKVDAAFKVAATAANAAPANDKFTVFEAAFNDEIKASTGGAYES

YKFIPALEAAVKQAYAATVATAPEVKYTVFETALKKAITAMSEAQKAAKPPPLPPP

PQPPPLAATGAATAATGGYKV

Phl p 5
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAAS

NKAFAEGLSGEPKGAAESSSKAALTSKLDAAYKLAYKTAEGATPEAKYDAY

VATLSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

APEVKYTVFETALKKAITAMSEAQKAAKPAAAATATATAAVGAATGAATA

ATGGYKV

Phl p 6
MAAHKFMVAMFLAVAVVLGLATSPTAEGGKATTEEQKLIEDVNASFRAAMATTANVPP

ADKYKTFEAAFTVSSKRNLADAVSKAPQLVPKLDEVYNAAYNAADHAAPEDKYEAFVLHF

SEALRIIAGTPEVHAVKPGA

Phl p 6
SKAPQLVPKLDEVYNAAYNAADHAAPEDKYEAFVLHFSEALHIIAGTPEVH

AVKPGA

Phl p 6
ADKYKTFEAAFTVSSKRNLADAVSKAPQLVPKLDEVYNAAYNAADHAAPEDKYEAFVLHF

SEALHIIAGTPEVHAVKPGA

Phl p 6
TEEQKLIEDVNASFRAAMATTANVPPADKYKTLEAAFTVSSKRNLADAVSK

APQLVPKLDEVYNAAYNAADHAAPEDKYEAFVLHFSEALRIIAGTPEVHAVKPGA

Phl p 6
MAAHKFMVAMFLAVAVVLGLATSPTAEGGKATTEEQKLIEDINASFRAAM

ATTANVPPADKYKTFEAAFTVSSKRNLADAVSKAPQLVPKLDEVYNAAYN

AADHAAPEDKYEAFVLHFSEALHIIAGTPEVHAVKPGA

Phl p 6
MVAMFLAVAVVLGLATSPTAEGGKATTEEQKLIEDVNASFRAAMATTANV

PPADKYKTFEAAFTVSSKRNLADAVSKAPQLVPKLDEVYNAAYNAADHAA

PEDKYEAFVLHFSEALRIIAGTPEVHAVKPGA

Phl p 7
MADDMERIFKRFDTNGDGKISLSELTDALRTLGSTSADEVQRMMAEIDTDGDGFIDF

NEFISFCNANPGLMKDVAKVF

-continued

Phl p 11
MSWQTYVDEHLMCEIEGHHLASAAILGHDGTVWAQSADFPQFKPEEITGIM

KDFDEPGHLAPTGMFVAGAKYMVIQGEPGRVIRGKKGAGGITIKKTGQALV

VGIYDEPMTPGQCNMVVERLGDYLVEQGM

Additional *Phleum* sequences (NCBI entrez accession):
458878; 548863; 2529314; 2529308; 2415702; 2415700; 2415698; 542168; 542167; 626037; 542169; 541814; 542171; 253337; 253336; 453976; 439960.

Wasp (and Related)
Vespula Sequences:

465054 ALLERGEN VES V 5
MEISGLVYLIIIVTIIDLPYGKANNYCKIKCLKGGVHTACKYGSLKPN

CGNKVVVSYGLTKQEKQDILKEHNDFRQKIARGLETRGNPGPQ

PPAKNMKNLVWNDELAYVAQVWANQCQYGHDTCRDVAKYQV

GQNVALTGSTAAKYDDPVKLVKMWEDEVKDYNPKKKFSGNDF

LKTGHYTQMVWANTKEVGCGSIKYIQEKWHKHYLVCNYGPSGN

FMNEELYQTK

1709545 ALLERGEN VES M 1
GPKCPFNSDTVSIIIETRENRNRDLYTLQTLQNHPEFKKKTITRPV

VFITHGFTSSASEKNFINLAKALVDKDNYMVISIDWQTAACTNEY

PGLKYAYYPTAASNTRLVGQYIATITQKLVKDYKISMANIRLIGHSL

GAHVSGFAGKRVQELKLGKYSEIIGLDPARPSFDSNHCSERLC

ETDAEYVQIIHTSNYLGTEKILGTVDFYMNNGKNNPGCGRFFSE

VCSHTRAVIYMAECIKHECCLIGIPRSKSSQPISRCTKQECVCV

GLNAKKYPSRGSFYVPVESTAPFCNNKGKII

1352699 ALLERGEN VES V 1
MEENMNLKYLLLFVYFVQVLNCCYGHGDPLSYELDRGPKCPF

NSDTVSIIIETRENRNRDLYTLQTLQNHPEFKKKTITRPVVFITHG

FTSSASETNFINLAKALVDKDNYMVISIDWQTAACTNEAAGLK

YLYYPTAARNTRLVGQYIATITQKLVKHYKISMANIRLIGHSLGAH

ASGFAGKKVQELKLGKYSEIIGLDPARPSFDSNHCSERLCET

DAEYVQIIHTSNYLGTEKTLGTVDFYMNNGKNQPGCGRFFSE

VCSHSRAVIYMAECIKHECCLIGIPKSKSSQPISSCTKQECVC

VGLNAKKYPSRGSFYVPVESTAPFCNNKGKII

1346323 ALLERGEN VES V 2
SERPKRVFNIYWNVPTFMCHQYDLYFDEVTNFNIKRNSKDDF

QGDKIAIFYDPGEFPALLSLKDGKYKKRNGGVPQEGNITIHLQ

KFIENLDKIYPNRNFSGIGVIDFERWRPIFRQNWGNMKIHKNF

SIDLVRNEHPTWNKKMIELEASKRFEKYARFFMEETLKLAK

KTRKQADWGYYGYPYCFNMSPNNLVPECDVTAMHENDKM

SWLFNNQNVLLPSVYVRQELTPDQRIGLVQGRVKEAVRISN

NLKHSPKVLSYWWYVYQDETNTFLTETDVKKTFQEIVINGG

DGIIIWGSSSDVNSLSKCKRLQDYLLTVLGPIAINVTEAVN

549194 ALLERGEN VES VI
5KVNYCKIKCLKGGVHTACKYGTSTKPNCGKMVVKAYGLT

EAEKQEILKVHNDFRQKVAKGLETRGNPGPQPPAKNMNN

LVWNDELANIAQVWASQCNYGHDTCKDTEKYPVGQNIAK

RSTTAALFDSPGKLVKMWENEVKDFNPNIEWSKNNLKKT

GHYTQMVWAKTKEIGCGSVKYVKDEWYTHYLVCNYGPSG

NFRNEKLYEKK

Additional vespula sequences (NCBI entrez accession):
49193; 549192; 549191; 549190; 5491104; 117414; 126761; 69576; 625255; 6271104; 627188; 627187; 482382; 112561; 627186; 627185; 1923233; 1047645; 1047647; 745570; 225764; 162551.

Tree Allergen Sequences (Mainly Birch) Sequences:

114922 Bet v 1
MGVFNYETETTSVIPAARLFKAFILDGDNLFPKVAPQAISSVENIEGNGGPGTI

KKISFPEGFPFKYVKDRVDEVDHTNFKYNYSVIEGGPIGDTLEKISNEIKIVAT

PDGGSILKISNKYHTKGDHEVKAEQVKASKEMGETLLRAVESYLLAHSDAYN

130975 Bet v 2
MSWQTYVDEHLMCDIDGQASNSLASAIVGHDGSVWAQSSSFPQFKPQEITGI

MKDFEEPGHLAPTGLHLGGIKYMVIQGEAGAVIRGKKGSGGITIKKTGQALV

FGIYEEPVTPGQCNMVVERLGDYLIDQGL

1168696 Bet v 3

-continued

MPCSTEAMEKAGHGHASTPRKRSLSNSSFRLRSESLNTLRLRRIFDLFDKNSD

GIITVDELSRALNLLGLETDLSELESTVKSFTREGNIGLQFEDFISLHQSLNDSY

FAYGGEDEDDNEEDMRKSILSQEEADSFGGFKVFDEDGDGYISARELQMVL

GKLGFSEGSEIDRVEKMIVSVDSNRDGRVDFFEFKDMMRSVLVRSS

809536 Bet v 4
MADDHPQDKAERERIFKRFDANGDGKISAAELGEALKTLGSITPDEVKHMM

AEIDTDGDGFISFQEFTDFGRANRGLLKDVAKIF

543675 Que a I - *Quercus alba* = oak trees (fragment)
GVFTXESQETSVIAPAXLFKALFL

543509 Car b I - *Carpinus betulus* = hornbeam trees (fragment)
GVFNYEAETPSVIPAARLFKSYVLDGDKLIPKVAPQAIXK 543491 Aln g I - *Alnus glutinosa* = alder trees (fragment)
GVFNYEAETPSVIPAARLFKAFILDGDKLLPKVAPEAVSSVENI 1204056 Rubisco
VQCMQVWPPLGLKKFETLSYLPPLSSEQLAKEVDYLLRKNLIPCLEFELEHG

FVYREHNRSPGYYDGRYWTMWKLPMFGCNDSSQVLKELEECKKAYPSAFI

RIIGFDDK

Additional tree allergen sequences (NCBI entrez accession number):
131919; 128193; 585564; 1942360; 2554672; 2392209; 2414158; 1321728; 1321726; 1321724; 1321722; 1321720; 1321718; 1321716; 1321714; 1321712; 3015520; 2935416; 464576; 1705843; 1168701; 1168710; 1168709; 1168708; 1168707; 1168706; 1168705; 1168704; 1168703; 1168702; 1842188; 2564228; 2564226; 2564224; 2564222; 2564220; 2051993; 18131041; 15368104; 534910; 534900; 5341048; 1340000; 1339998; 2149808; 66207; 2129477; 1076249; 1076247; 629480; 481805; 81443; 1361968; 1361967; 1361966; 1361965; 1361964; 1361963; 1361962; 1361961; 1361960; 1361959; 320546; 629483; 629482; 629481; 541804; 320545; 81444; 541814; 629484; 474911; 452742; 1834387; 298737; 298736; 1584322; 1584321; 584320; 1542873; 1542871; 1542869; 1542867; 1542865; 1542863; 1542861; 1542859; 1542857; 1483232; 1483230; 1483228; 558561; 551640; 488605; 452746; 452744; 452740; 452738; 452736; 452734; 452732; 452730; 452728; 450885; 17938; 17927; 17925; 17921; 297538; 510951; 2104331; 2104329; 166953.

Peanut
Peanut sequences

1168391 Ara h 1
MRGRVSPLMLLLGILVLASVSATHAKSSPYQKKTENPCAQRCLQSCQQEP

DDLKQKACESRCTKLEYDPRCVYDPRGHTGTTNQRSPPGERTRGRQPGDY

DDDRRQPRREEGGRWGPAGPREREREEDWRQPREDWRRPSHQQPRKIRPE

GREGEQEWGTPGSHVREETSRNNPFYFPSRRFSTRYGNQNGRIRVLQRFD

QRSRQFQNLQNHRIVQIEAKPNTLVLPKHADADNILVIQQGQATVTVANG

NNRKSFNLDEGHALRIPSGFISYILNRHDNQNLRVAKISMPVNTPGQFED

FFPASSRDQSSYLQGFSRNTLEAAFNAEFNEIRRVLLEENAGGEQEERGQ

RRWSTRSSENNEGVIVKVSKEHVEELTKHAKSVSKKGSEEEGDITNPINL

REGEPDLSNNFGKLFEVKPDKKNPQLQDLDMMLTCVEIKEGALMLPHFNS

KAMVIVVVNKGTGNLELVAVRKEQQQRGRREEEEDEDEEEEGSNREVRRY

TARLKEGDVFIMPAAHPVAINASSELHLLGFGINAENNHRIFLAGDKDNV

IDQIEKQAKDLAFPGSGEQVEKLIKNQKESHFVSARPQSQSQSPSSPEKE

SPEKEDQEEENQGGKGPLLSILKAFN

Ragweed
*Ambrosia* Sequences

113478 Amb a 1
MGIKHCCYILYFTLALVTLLQPVRSAEDLQQILPSANETRSLTTCGTYNI

IDGCWRGKADWAENRKALADCAQGFAKGTIGGKDGDIYTVTSELDDDVAN

PKEGTLRFGAAQNRPLWIIFARDMVIRLDRELAINNDKTIDGRGAKVEII

NAGFAIYNVKNIIIHNIIMHDIVVNPGGLIKSHDGPPVPRKGSDGDAIGI

SGGSQIWIDHCSLSKAVDGLIDAKHGSTHFTVSNCLFTQHQYLLLFWDFD

ERGMLCTVAFNKFTDNVDQRMPNLRHGFVQVVNNNYERWGSYALGGSAGP

TILSQGNRFLASDIKKEVVGRYGESAMSESINWNWRSYMDVFENGAIFVP

SGVDPVLTPEQNAGMIPAEPGEAVLRLTSSAGVLSCQPGAPC

113479 Amb a 2
MGIKHCCYILYFTLALVTLVQAGRLGEEVDILPSPNDTRRSLQGCEAHNI

IDKCWRCKPDWAENRQALGNCAQGFGKATHGGKWGDIYMVTSDQDDDVVN

PKEGTLRFGATQDRPLWIIFQRDMIIYLQQEMVVTSDKTIDGRGAKVELV

YGGITLMNVKNVIIHNIDIHDVRVLPGGRIKSNGGPAIPRHQSDGDAIHV

TGSSDIWIDHCTLSKSFDGLVDVNWGSTGVTISNCKFTHHEKAVLLGASD

THFQDLKMHVTLAYNIFTNTVHERMPRCRFGFFQIVNNFYDRWDKYAIGG

SSNPTILSQGNKFVAPDFIYKKNVCLRTGAQEPEWMTWNWRTQNDVLENG

AIFVASGSDPVLTAEQNAGMMQAEPGDMVPQLTMNAGVLTCSPGAPC

113477 Amb a 1.3
MGIKQCCYILYFTLALVALLQPVRSAEGVGEILPSVNETRSLQACEALNI
IDKCWRGKADWENNRQALADCAQGFAKGTYGGKWGDVYTVTSNLDDDVAN
PKEGTLRFAAAQNRPLWIIFKNDMVINLNQELVVNSDKTIDGRGVKVEII
NGGLTLMNVKNIIHNINIHDVKVLPGGMIKSNDGPPILRQASDGDTINV
AGSSQIWIDHCSLSKSFDGLVDVTLGSTHVTISNCKFTQQSKAILLGADD
THVQDKGMLATVAFNMFTDNVDQRMPRCRFGFFQVVNNNYDRWGTYAIGG
SSAPTILCQGNRFLAPDDQIKKNVLARTGTGAAESMAWNWRSDKDLLENG
AIFVTSGSDPVLTPVQSAGMIPAEPGEAAIKLTSSAGVFSCHPGAPC

113476 Amb a 1.2
MGIKHCCYILYFTLALVTLLQPVRSAEDVEEFLPSANETRRSLKACEAHN
IIDKCWRCKADWANNRQALADCAQGFAKGTYGGKHGDVYTVTSDKDDDVA
NPKEGTLRFAAAQNRPLWIIFKRNMVIHLNQELVVNSDKTIDGRGVKVNI
VNAGLTLMNVKNIIHNINIHDIKVCPGGMIKSNDGPPILRQQSDGDAIN
VAGSSQIWIDHCSLSKASDGLLDITLGSSHVTVSNCKFTQHQFVLLLGAD
DTHYQDKGMLATVAFNMFTDHVDQRMPRCRFGFFQVVNNNYDRWGTYAIG
GSSAPTILSQGNRFFAPDDIIKKNVLARTGTGNAESMSWNWRTDRDLLEN
GAIFLPSGSDPVLTPEQKAGMIPAEPGEAVLRLTSSAGVLSCHQGAPC

113475 Amb a 1.1
MGIKHCCYILYFTLALVTLLQPVRSAEDLQEILPVNETRRLTTSGAYNII
DGCWRGKADWAENRKALADCAQGFGKGTVGGKDGDIYTVTSELDDDVANP
KEGTLRFGAAQNRPLWIIFERDMVIRLDKEMVVNSDKTIDGRGAKVEIIN
AGFTLNGVKNVIIHNINMHDVKVNPGGLIKSNDGPAAPRAGSDGDAISIS
GSSQIWIDHCSLSKSVDGLVDAKLGTTRLTVSNSLFTQHQFVLLFGAGDE
NIEDRGMLATVAFNTFTDNVDQRMPRCRHGFFQVVNNNYDKWGSYAIGGS
ASPTILSQGNRFCAPDERSKKNVLGRHGEAAAESMKWNWRTNKDVLENGA
IFVASGVDPVLTPEQSAGMIPAEPGESALSLTSSAGVLSCQPGAPC

Cedar Sequences

493634 Cry j IB precursor
MDSPCLVALLVFSFVIGSCFSDNPIDSCWRGDSNWAQNRMKLADCAVGFG
SSTMGGKGGDLYTVTNSDDDPVNPPGTLRYGATRDRPLWIIFSGNMNIKL
KMPMYIAGYKTFDGRGAQVYIGNGGPCVFIKRVSNVIIHGLYLYGCSTSV
LGNVLINESFGVEPVHPQDGDALTLRTATNIWIDHNSFSNSSDGLVDVTL
TSTGVTISNNLFFNHHKVMSLGHDDAYSDDKSMKVTVAFNQFGPNCGQRM
PRARYGLVHVANNNYDPWTIYAIGGSSNPTILSEGNSFTAPNESYKKQVT
IRIGCKTSSSCSNWVWQSTQDVFYNGAYFVSSGKYEGGNIYTKKEAFNVE
NGNATPHLTQNAGVLTCSLSKRC 493632 Cry j IA precursor
MDSPCLVALLVLSFVIGSCFSDNPIDSCWRGDSNWAQNRMKLADCAVGFG
SSTMGGKGGDLYTVTNSDDDPVNPAPGTLRYGATRDRPLWIIFSGNMNIK
LKMPMYIAGYKTFDGRGAQVYIGNGGPCVFIKRVSNVIIHGLHLYGCSTS
VLGNVLINESFGVEPVHPQDGDALTLRTATNIWIDHNSFSNSSDGLVDVT LSSTGVTISNNLFFNHHKVMLLGHDDAYSDDKSMKVTVAFNQFGPNCGQR
MPRARYGLVHVANNNYDPWTIYAIGGSSNPTILSEGNSFTAPNESYKKQV
TIRIGCKTSSSCSNWVWQSTQDVFYNGAYFVSSGKYEGGNIYTKKEAFNV
ENGNATPQLTKNAGVLTCSLSKRC 1076242 Cry j II precursor - Japanese cedar
MAMKLIAPMAFLAMQLIIMAAAEDQSAQIMLDSVVEKYLRSNRSLRKVEH
SRHDAINIFNVEKYGAVGDGKHDCTEAFSTAWQAACKNPSAMLLVPGSKK
FVVNNLFFNGPCQPHFTFKVDGIIAAYQNPASWKNNRIWLQFAKLTGFTL
MGKGVIDGQGKQWWAGQCKWVNGREICNDRDRPTAIKFDFSTGLIIQGLK
LMNSPEFHLVFGNCEGVKIIGISITAPRDSPNTDGIDIFASKNFHLQKNT
IGTGDDCVAIGTGSSNIVIEDLICGPGHGISIGSLGRENSRAEVSYVHVN
GAKFIDTQNGLRIKTWQGGSGMASHIIYENVEMINSENPILINQFYCTSA
SACQNQRSAVQIQDVTYKNIRGTSATAAAIQLKCSDSMPCKDIKLSDISL
KLTSGKIASCLNDNANGYFSGHVIPACKNLSPSAKRKESKSHKHPKTVMV
ENMRAYDKGNRTRILLGSRPPNCTNKCHGCSPCKAKLVIVHRIMPQEYYP
QRWICSCHGKIYHP 1076241 Cry j II protein - Japanese cedar
MAMKFIAPMAFVAMQLIIMAAAEDQSAQIMLDSDIEQYLRSNRSLRKVEH
SRHDAINIFNVEKYGAVGDGKHDCTEAFSTAWQAACKKPSAMLLVPGNKK
FVVNNLFFNGPCQPHFTFKVDGIIAAYQNPASWKNNRIWLQFAKLTGFTL
MGKGVIDGQGKQWWAGQCKWVNGREICNDRDRPTAIKFDFSTGLIIQGLK
LMNSPEFHLVFGNCEGVKIIGISITAPRDSPNTDGIDIFASKNFHLQKNT
IGTGDDCVAIGTGSSNIVIEDLICGPGHGISIGSLGRENSRAEVSYVHVN
GAKFIDTQNGLRIKTWQGGSGMASHIIYENVEMINSENPILINQFYCTSA
SACQNQRSAVQIQDVTYKNIRGTSATAAAIQLKCSDSMPCKDIKLSDISL
KLTSGKIASCLNDNANGYFSGHVIPACKNLSPSAKRKESKSHKHPKTVMV
KNMGAYDKGNRTRILLGSRPPNCTNKCHGCSPCKAKLVIVHRIMPQEYYP
QRWMCSRHGKIYHP 541803 Cry j I precursor - Japanese cedar
MDSPCLVALLVLSFVIGSCFSDNPIDSCWRGDSNWAQNRMKLADCAVGFG
SSTMGGKGGDLYTVTNSDDDPVNPPGTLRYGATRDRPLWIIFSGNMNIKL
KMPMYIAGYKTFDGRGAQVYIGNGGPCVFIKRVSNVIIHGLHLYGCSTSV
LGNVLINESFGVEPVHPQDGDALTLRTATNIWIDHNSFSNSSDGLVDVTL
SSTGVTISNNLFFNHHKVMLLGHDDAYSDDKSMKVTVAFNQFGPNCGQRM
PRARYGLVHVANNNYDPWTIYAIGGSSNPTILSEGNSFTAPNESYKKQVT
IRIGCKTSSSCSNWVWQSTQDVFYNGAYFVSSGKYEGGNIYTKKEAFNVE
NGNATPQLTKNAGVLTCSLSKRC 541802 Cry j I precursor - Japanese cedar
MDSPCLVALLVFSFVIGSCFSDNPIDSCWRGDSNWAQNRMKLADCAVGFG
SSTMGGKGGDLYTVTNSDDDPVNPAPGTLRYGATRDRPLWIIFSGNMNIK
LKMPMYIAGYKTFDGRGAQVYIGNGGPCVFIKRVSNVIIHGLYLYGCSTS
VLGNVLINESFGVEPVHPQDGDALTLRTATNIWIDHNSFSNSSDGLVDVT -continued
```
LTSTGVTISNNLFFNHHKVMSLGHDDAYSDDKSMKVTVAFNQFGPNCGQR

MPRARYGLVHVANNNYDPWTIYAIGGSSNPTILSEGNSFTAPNESYKKQV

TIRIGCKTSSSCSNWVWQSTQDVFYNGAYFVSSGKYEGGNIYTKKEAFNV

ENGNATPHLTQNAGVLTCSLSKRC
```

Dog
Canis Sequences:

```
Can f 1
MKTLLLTIGFSLIAILQAQDTPALGKDTVAVSGKWYLKAMTADQEVPEKP

DSVTPMILKAQKGGNLEAKITMLTNGQCQNITVVLHKTSEPGKYTAYEGQ

RVVFIQPSPVRDHYILYCEGELHGRQIRMAKLLGRDPEQSQEALEDFREF

SRAKGLNQEILELAQSETCSPGGQ

Serum albumin fragment
EAYKSEIAHRYNDLGEEHFRGLVL

Serum albumin fragment
LSSAKERFKCASLQKFGDRAFKAWSVARLSQRFPKADFAEISKVVTDLTK

VHKECCHGDLLECADDRADLAKYMCENQDSISTKLKECCDKPVLEKSQCL

AEVERDELPGDLPSLAADFVEDKEVCKNYQEAKDVFLGTFLYEYSRRHPE

YSVSLLLRLAKEYEATLEKCCATDDPPTCYAKVLDEFKPLVDEPQNLVKT

NCELFEKLGEYGFQNALLVRYTKKAPQVSTPTLVVEVSRKLGKVGTKCCK

KPESERMSCADDFLS

Can f 2
MQLLLLTVGLALICGLQAQEGNHEEPQGGLEELSGRWHSVALASNKSDLI

KPWGHFRVFIHSMSAKDGNLHGDILIPQDGQCEKVSLTAFKTATSNKFDL

EYWGHNDLYLAEVDPKSYLILYMINQYNDDTSLVAHLMVRDLSRQQDFLP

AFESVCEDIGLHKDQIVVLSDDDRCQGSRD
```

Additional dog allergen protein (NCBI entrez accession): 1731859

Horse
Equus Sequences:

```
1575778 Equ c1
MKLLLLCLGLILVCAQQEENSDVAIRNFDISKISGEWYSIFLASDVKEKI

EENGSMRVFVDVIRALDNSSLYAEYQTKVNGECTEFPMVFDKTEEDGVYS

LNYDGYNVFRISEFENDEHIILYLVNFDKDRPFQLFEFYAREPDVSPEIK

EEFVKIVQKRGIVKENIIDLTKIDRCFQLRGNGVAQA

3121755 Equ c 2
SQXPQSETDYSQLSGEWNTIYGAASNIXK
```

Euroglyphus (Mite)
Euroglyphus Sequences:

```
Eur m 1 (variant)
TYACSINSVSLPSELDLRSLRTVTPIRMQGGCGSCWAFSGVASTESAYLA

YRNMSLDLAEQELVDCASQNGCHGDTIPRGIEYIQQNGVVQEHYYPYVAR

EQSCHRPNAQRYGLKNYCQISPPDSNKIRQALTQTHTAVAVIIGIKDLNA

FRHYDGRTIMQHDNGYQPNYHAVNIVGYGNTQGVDYWIVRNSWDTTWGDN

GYGYFAANINL

Eur m 1 (variant)
TYACSINSVSLPSELDLRSLRTVTPIRMQGGCGSCWAFSGVASTESAYLA

YRNMSLDLAEQELVDCASQNGCHGDTIPRGIEYIQQNGVVQEHYYPYVAR

EQSCHRPNAQRYGLKNYCQISPPDSNKIRQALTQTHTAVAVIIGIKDLNA

FRHYDGRTIMQHDNGYQPNYHAVNIVGYGNTQGVDYWIVRNSWDTTWGDN

GYGYFAANINL

Eur m 1 (variant)
ETNACSINGNAPAEIDLRQMRTVTPIRMQGGCGSCWAFSGVAATESAYLA

YRNQSLDLAEQELVDCASQNGCHGDTIPRGIEYIQHNGVVQESYYRYVAR

EQSCRRPNAQRFGISNYCQIYPPNANKIREALAQTHSAIAVIIGIKDLDA

FRHYDGRTIIQRDNGYQPNYHAVNIVGYSNAQGVDYWIVRNSWDTNWGDN

GYGYFAANIDL

Eur m 1 (variant)
ETSACRINSVNVPSELDLRSLRTVTPIRMQGGCGSCWAFSGVAATESAYL

AYRNTSLDLSEQELVDCASQHGCHGDTIPRGIEYIQQNGVVEERSYPYVA

REQQCRRPNSQHYGISNYCQIYPPDVKQIREALTQTHTAIAVIIGIKDLR

AFQHYDGRTIIQHDNGYQPNYHAVNIVGYGSTQGVDYWIVRNSWDTTWGD

SGYGYFQAGNNL
```

Poa (Grass) Sequences

```
113562 POLLEN ALLERGEN POA P 9
MAVQKYTVALFLVALVVGPAASYAADLSYGAPATPAAPAAGYTPAAPAGA

APKATTDEQKMIEKINVGFKAAVAAAGGVPAANKYKTFVATFGAASNKAF

AEALSTEPKGAAVDSSKAALTSKLDAAYKLAYKSAEGATPEAKYDDYVAT

LSEALRIIAGTLEVHGVKPAAEEVKATPAGELQVIDKVDAAFKVAATAAN

AAPANDKFTVFEAAFNDAIKASTGGAYQSYKFIPALEAAVKQSYAATVAT

APAVKYTVFETALKKAITAMSQAQKAAKPAAAATGTATAAVGAATGAATA

AAGGYKV

113561 POA P 9
MAVHQYTVALFLAVALVAGPAASYAADVGYGAPATLATPATPAAPAAGYT

PAAPAGAAPKATTDEQKLIEKINAGFKAAVAAAAGVPAVDKYKTFVATFG

TASNKAFAEALSTEPKGAAAASSNAVLTSKLDAAYKLAYKSAEGATPEAK

YDAYVATLSEALRIIAGTLEVHAVKPAGEEVKAIPAGELQVIDKVDAAFK

VAATAANAAPANDKFTVFEAAFNDAIKASTGGAYQSYKFIPALEAAVKQS

YAATVATAPAVKYTVFETALKKAITAMSQAQKAAKPAAAVTATATGAVGA

ATGAVGAATGAATAAAGGYKTGAATPTAGGYKV

113560 POA P 9
MDKANGAYKTALKAASAVAPAEKFPVFQATFDKNLKEGLSGPDAVGFAKK

LDAFIQTSYLSTKAAEPKEKFDLFVLSLTEVLRFMAGAVKAPPASKFPAK

PAPKVAAYTPAAPAGAAPKATTDEQKLIEKINVGFKAAVAAAAGVPAASK

YKTFVATFGAASNKAFAEALSTEPKGAAVASSKAVLTSKLDAAYKLAYKS

AEGATPEAKYDAYVATLSEALRIIAGTLEVHGVKPAAEEVKAIPAGELQV

IDKVDAAFKVAATAANAAPANDKFTVFEAAFNDAIKASTGGAYQSYKFIP
```

-continued

ALEAAVKQSYAATVATAPAVKYTVFETALKKAITAMSQAQKAAKPAAAVT

GTATSAVGAATGAATAAAGGYKV

Cockroach Sequences

2833325 Cr p1
MKTALVFAAVVAFVAARFPDHKDYKQLADKQFLAKQRDVLRLFHRVHQHN

ILNDQVEVGIPMTSKQTSATTVPPSGEAVHGVLQEGHARPRGEPFSVNYE

KHREQAIMLYDLLYFANDYDTFYKTACWARDRVNEGMFMYSFSIAVFHRD

DMQGVMLPPPYEVYPYLFVDHDVIHMAQKYWMKNAGSGEHHSHVIPVNFT

LRTQDHLLAYFTSDVNLNAFNTYYRYYYPSWYNTTLYGHNIDRRGEQFYY

TYKQIYARYFLERLSNDLPDVYPFYYSKPVKSAYNPNLRYHNGEEMPVRP

SNMYVTNFDLYYIADIKNYEKRVEDAIDFGYAFDEHMKPHSLYHDVHGME

YLADMIEGNMDSPNFYFYGSIYHMYHSMIGHIVDPYHKMGLAPSLEHPET

VLRDPVFYQLWKRVDHLFQKYKNRLPRYTHDELAFEGVKVENVDVGKLYT

YFEQYDMSLDMAVYVNNVDQISNVDVQLAVRLNHKPFTYNIEVSSDKAQD

VYVAVFLGPKYDYLGREYDLNDRRHYFVEMDRFPYHVGAGKTVIERNSHD

SNIIAPERDSYRTFYKKVQEAYEGKSQYYVDKGHNYCGYPENLLIPKGKK

GGQAYTFYVIVTPYVKQDEHDFEPYNYKAFSYCGVGSERKYPDNKPLGYP

FDRKIYSNDFYTPNMYFKDVIIFHKKYDEVGVQGH

2231297 Cr p2
INEIHSIIGLPPFVPPSRRHARRGVGINGLIDDVIAILPVDELKALFQEK

LETSPDFKALYDAIRSPEFQSIISTLNAMQRSEHHQNLRDKGVDVDHFIQ

LIRALFGLSRAARNLQDDLNDFLHSLEPISPRHRHGLPRQRRRSARVSAY

LHADDFHKIITTIEALPEFANFYNFLKEHGLDVVDYINEIHSIIGLPPFV

PPSRRHARRGVGINGLIDDVIAILPVDELKALFQEKLETSPDFKALYDAI

RSPEFQSIISTLNAMPEYQELLQNLRDKGVDVDHFIRVDQGTLRTLSSGQ

RNLQDDLNDFLALIPTDQILAIAMDYLANDAEVQELVAYLQSDDFHKIIT

TIEALPEFANFYNFLKEHGLDVVDYINEIHSIIGLPPFVPPSQRHARRGV

GINGLIDDVIAILPVDELKALFQEKLETSPDFKALYDAIDLRSSRA

1703445 Bla g 2
MIGLKLVTVLFAVATITHAAELQRVPLYKLVHVFINTQYAGITKIGNQNF

LTVFDSTSCNVVVASQECVGGACVCPNLQKYEKLKPKYISDGNVQVKFFD

TGSAVGRGIEDSLTISNLTTSQQDIVLADELSQEVCILSADVVVGIAAPG

CPNALKGKTVLENFVEENLIAPVFSIHHARFQDGEHFGEIIFGGSDWKYV

DGEFTYVPLVGDDSWKFRLDGVKIGDTTVAPAGTQAIIDTSKAIIVGPKA

YVNPINEAIGCVVEKTTTRRICKLDCSKIPSLPDVTFVINGRNFNISSQY

YIQQNGNLCYSGFQPCGHSDHFFIGDFFVDHYYSEFNWENKTMGFGRSVE

SV

1705483 Bla g 4
AVLALCATDTLANEDCFRHESLVPNLDYERFRGSWIIAAGTSEALTQYKC

WIDRFSYDDALVSKYTDSQGKNRTTIRGRTKFEGNKFTIDYNDKGKAFSA

PYSVLATDYENYAIVEGCPAAANGHVIYVQIRFSVRRFHPKLGDKEMIQH

YTLDQVNQHKKAIEEDLKHFNLKYEDLHSTCH

2326190 Bla g 5
YKLTYCPVKALGEPIRFLLSYGEKDFEDYRFQEGDWPNLKPSMPFGKTPV

LEIDGKQTHQSVAISRYLGKQFGLSGKDDWENLEIDMIVDTISDFRAAIA

NYHYDADENSKQKKWDPLKKETIPYYTKKFDEVVKANGGYLAAGKLTWAD

FYFVAILDYLNHMAKEDLVANQPNLKALREKVLGLPAIKAWVAKRPPTDL

Additional cockroach sequences (NCBI Entrez accession numbers):
2580504; 1580797; 1580794; 1362590; 544619; 544618; 15315104; 1580792; 1166573; 1176397; 21047849.

Allergen (General) Sequences:
NCBI accession numbers
2739154; 3719257; 3703107; 3687326; 3643813; 3087805; 1864024; 1493836; 1480457; 25910476; 25910474; 1575778; 763532; 746485; 163827; 163823; 3080761; 163825; 3608493; 3581965; 2253610; 2231297; 21047849; 3409499; 3409498; 3409497; 3409496; 3409495; 3409494; 3409493; 3409492; 3409491; 3409490; 34094104; 3409488; 3409487; 3409486; 3409485; 3409484; 3409483; 3409482; 3409481; 3409480; 3409479; 3409478; 3409477; 3409476; 3409475; 3409474; 3409473; 3409472; 3409471; 3409470; 3409469; 3409468; 3409467; 3409466; 3409465; 3409464; 3409463; 3409462; 3409461; 3409460; 3409459; 3409458; 3409457; 3409456; 3318885; 3396070; 3367732; 1916805; 3337403; 2851457; 2851456; 1351295; 549187; 136467; 1173367; 2499810; 2498582; 2498581; 1346478; 1171009; 126608; 114091; 2506771; 1706660; 1169665; 1169531; 232086; 4161048; 114922; 2497701; 1703232; 1703233; 1703233; 1703232; 3287877; 3122132; 3182907; 3121758; 3121756; 3121755; 3121746; 3121745; 3319925; 3319923; 3319921; 3319651; 33187104; 3318779; 3309647; 3309047; 3309045; 3309043; 3309041; 3309039; 3288200; 3288068; 2924494; 3256212; 3256210; 3243234; 3210053; 3210052; 3210051; 3210050; 3210049; 3210048; 3210047; 3210046; 3210045; 3210044; 3210043; 3210042; 3210041; 3210040; 3210039; 3210038; 3210037; 3210036; 3210035; 3210034; 3210033; 3210032; 3210031; 3210030; 3210029; 3210028; 3210027; 3210026; 3210025; 3210024; 3210023; 3210022; 3210021; 3210020; 3210019; 3210018; 3210017; 3210016; 3210015; 3210014; 3210013; 3210012; 3210011; 3210010; 3210009; 3210008; 3210007; 3210006; 3210005; 3210004; 3210003; 3210002; 3210001; 3210000; 3209999; 3201547; 2781152; 2392605; 2392604; 2781014; 1942360; 2554672; 2392209; 3114481; 3114480; 2981657; 3183706; 3152922; 3135503; 3135501; 3135499; 3135497; 2414158; 1321733; 1321731; 1321728; 1321726; 1321724; 1321722; 1321720; 1321718; 1321716; 1321714; 1321712; 3095075; 3062795; 3062793; 3062791; 2266625; 2266623; 2182106; 3044216; 2154736; 3021324; 3004467; 3005841; 3005839; 3004485; 3004473; 3004471; 3004469; 3004465; 2440053; 1805730; 2970629; 29591048; 2935527; 2935416; 809536; 730091; 585279; 584968; 2498195; 2833325; 2498604; 2498317; 2498299; 2493414; 2498586; 2498585; 2498576; 2497749; 2493446; 2493445; 1513216; 729944; 2498099; 548449; 465054; 465053; 465052; 548671; 548670; 548660; 548658; 548657; 2832430; 232084; 2500822; 2498118; 2498119; 2498119; 2498118; 1708296; 1708793; 416607; 416608; 416608;

416607; 2499791; 2498580; 2498579; 2498578; 2498577; 2497750; 1705483; 1703445; 1709542; 1709545; 17105104; 1352699; 1346568; 1346323; 1346322; 2507248; 11352240; 1352239; 1352237; 1352229; 1351935; 1350779; 1346806; 1346804; 1346803; 1170095; 1168701; 1352506; 1171011; 1171008; 1171005; 1171004; 1171002; 1171001; 1168710; 1168709; 1168708; 1168707; 1168706; 1168705; 1168704; 1168703; 1168702; 1168696; 1168391; 1168390; 1168348; 1173075; 1173074; 1173071; 1169290; 11610470; 1168402; 729764; 729320; 729979; 729970; 729315; 730050; 730049; 730048; 549194; 549193; 549192; 549191; 549190; 5491104; 549188; 549185; 549184; 549183; 549182; 549181; 549180; 549179; 464471; 585290; 416731; 1169666; 113478; 113479; 113477; 113476; 113475; 130975; 119656; 113562; 113561; 113560; 416610; 126387; 126386; 126385; 132270; 416611; 416612; 416612; 416611; 730035; 127205; 1352238; 125887; 549186; 137395; 730036; 133174; 114090; 131112; 126949; 129293; 124757; 129501; 416636; 2801531; 2796177; 2796175; 2677826; 2735118; 2735116; 2735114; 2735112; 2735110; 2735108; 2735106; 2735104; 2735102; 2735100; 2735098; 2735096; 2707295; 2154730; 2154728; 1684720; 2580504; 2465137; 2465135; 2465133; 2465131; 2465129; 2465127; 2564228; 2564226; 2564224; 2564222; 2564220; 2051993; 1313972; 1313970; 1313968; 1313966; 2443824; 2488684; 2488683; 2488682; 2488681; 2488680; 2488679; 2488678; 2326190; 2464905; 2415702; 2415700; 2415698; 2398759; 2398757; 2353266; 2338288; 1167836; 414703; 2276458; 1684718; 2293571; 1580797; 1580794; 2245508; 2245060; 1261972; 2190552; 1881574; 511953; 1532058; 1532056; 1532054; 1359436; 666007; 487661; 217308; 1731859; 217306; 217304; 1545803; 1514943; 577696; 516728; 506858; 493634; 493632; 2154734; 2154732; 543659; 1086046; 1086045; 2147643; 2147642; 1086003; 1086002; 1086001; 543675; 543623; 543509; 543491; 1364099; 2147108; 2147107; 1364001; 1085628; 631913; 631912; 631911; 2147092; 477301; 543482; 345521; 542131; 542130; 542129; 100636; 2146809; 480443; 2114497; 2144915; 72355; 71728; 319828; 1082946; 1082945; 1082944; 539716; 539715; 423193; 423192; 423191; 423190; 1079187; 627190; 6271104; 627188; 627187; 482382; 1362656; 627186; 627185; 627182; 482381; 85299; 85298; 2133756; 2133755; 1079186; 627181; 321044; 321043; 112559; 112558; 1362590; 2133564; 1085122; 10710471; 627144; 627143; 627142; 627141; 280576; 102835; 102834; 102833; 102832; 84703; 84702; 84700; 84699; 84698; 84696; 477888; 477505; 102575; 102572; 478272; 2130094; 629813; 629812; 542172; 542168; 542167; 481432; 320620; 280414; 626029; 542132; 320615; 320614; 100638; 100637; 100635; 82449; 320611; 320610; 280409; 320607; 320606; 539051; 539050; 539049; 539048; 322803; 280407; 100501; 100498; 100497; 100496; 1362137; 1362136; 1362135; 1362134; 1362133; 1362132; 1362131; 1362130; 1362129; 1362128; 100478; 21291041; 1076531; 1362049; 1076486; 2129817; 2129816; 2129815; 2129814; 2129813; 2129812; 2129805; 2129804; 2129802; 2129801; 2129800; 2129799; 479902; 479901; 2129477; 1076247; 629480; 1076242; 1076241; 541803; 541802; 280372; 280371; 1361968; 1361967; 1361966; 1361965; 1361964; 1361963; 1361962; 1361961; 1361960; 1361959; 320546; 2119763; 543622; 541804; 478825; 478824; 478823; 421788; 320545; 81444; 626037; 626028; 539056; 483123; 481398; 481397; 100733; 100732; 100639; 625532; 1083651; 322674; 322673; 81719; 81718; 2118430; 2118429; 2118428; 2118427; 419801; 419800; 419799; 419798; 282991; 100691; 322995; 322994; 101824; 626077; 414553; 398830; 1311457; 1916292; 1911819; 1911818; 1911659; 1911582; 467629; 467627; 467619; 467617; 915347; 1871507; 1322185; 1322183; 1047645; 1047647; 1850544; 1850542; 1850540; 2810417; 452742; 1842045; 1839305; 1836011; 1836010; 1829900; 18291049; 18291048; 18291047; 18291046; 18291045; 18291044; 1825459; 18010487; 159653; 1773369; 1769849; 1769847; 608690; 1040877; 1040875; 1438761; 1311513; 1311512; 1311511; 1311510; 1311509; 13116104; 1246120; 1246119; 1246118; 1246117; 1246116; 1478293; 1478292; 1311642; 1174278; 1174276; 1086972; 1086974; 1086976; 1086978; 1086978; 1086976; 1086974; 1086972; 999009; 999356; 999355; 994866; 994865; 913758; 913757; 913756; 913285; 913283; 926885; 807138; 632782; 601807; 46852; 633938; 544619; 544618; 453094; 451275; 451274; 407610; 407609; 404371; 409328; 299551; 299550; 264742; 261407; 255657; 250902; 250525; 1613674; 1613673; 1613672; 1613671; 1613670; 1613304; 1613303; 1613302; 1613240; 1613239; 1613238; 1612181; 1612180; 1612179; 1612178; 1612177; 1612176; 1612175; 1612174; 1612173; 1612172; 1612171; 1612170; 1612169; 1612168; 1612167; 1612166; 1612165; 1612164; 1612163; 1612162; 1612161; 1612160; 1612159; 1612158; 1612157; 1612156; 1612155; 1612154; 1612153; 1612152; 1612151; 1612150; 1612149; 1612148; 1612147; 1612146; 1612145; 1612144; 1612143; 1612142; 1612141; 1612140; 1612139; 1093120; 447712; 447711; 447710; 1587177; 158542; 1582223; 1582222; 15315104; 1580792; 886215; 15451047; 15451045; 15451043; 15451041; 15458104; 1545887; 1545885; 1545883; 1545881; 1545879; 1545877; 1545875; 166486; 1498496; 1460058; 972513; 1009442; 1009440; 1009438; 1009436; 1009434; 7413; 1421808; 551228; 452606; 32905; 1377859; 1364213; 1364212; 395407; 22690; 22688; 22686; 22684; 488605; 17680; 1052817; 1008445; 1008443; 992612; 706811; 886683; 747852; 939932; 19003; 1247377; 1247375; 1247373; 862307; 312284; 999462; 999460; 999458; 587450; 763064; 886209; 1176397; 1173557; 902012; 997915; 997914; 997913; 997912; 997911; 997910; 99790; 997908; 997907; 997906; 997905; 997904; 997903; 997902; 997901; 997900; 9971049; 9971048; 9971047; 9971046; 9971045; 9971044; 9971043; 9971042; 910984; 910983; 910982; 910981; 511604; 169631; 169629; 169627; 168316; 168314; 607633; 555616; 293902; 485371; 455288; 166447; 166445; 166443; 166435; 162551; 160780; 552080; 156719; 156715; 515957; 515956; 515955; 515954; 515953; 459163; 166953; 386678; 169865.

Particularly preferred T cell epitopes are derived from the allergens: cat dander protein Fel d1; House dust mite proteins Der P1, Der P2 and Der P7; Ragweed protein amb a 1.1, a 1.2, a1.3 or a1.4; Rye grass proteins lol p1 and lol p5; Timothy grass proteins phl p1 and phl p5; Bermuda grass protein Cyn d 5; *Alternaria* alternate proteins Alt a 1, Alt a 2 and Enolase (Alt a 6); Birch protein Bet v1 and P14; German Cockroach proteins Bla g 1, Bla g 2, Bla g 3, Bla g 4, Bla g 5 and Bla g 6; Mugwort protein Art v 1; Russian thistle protein Sal k 1 and Sal k 2; peanut Ara h1, Ara h2, Ara h3, Ara h4, Ara h5, Ara h6, plant profilins or lipid transfer proteins or a human leukocyte antigen.

Suitable autoimmune antigens from which the MHC Class II-binding T cell epitope may derive can of course be obtained and/or produced using known methods. Suitable autoimmune antigens include the major antigens in the following autoimmune diseases: Acute disseminated encephalomyelitis (ADEM); Addison's disease; Ankylosing spondylitis; Antiphospholipid antibody syndrome (APS); Aplastic anemia; Autoimmune hepatitis; Autoimmune Oophoritis; Coeliac disease; Crohn's disease; Diabetes mellitus type 1; Gestational pemphigoid; Goodpasture's syndrome; Graves' disease; Guillain-Barré syndrome (GBS); Hashimoto's disease; Idiopathic thrombocytopenic purpura; Kawasaki's Disease; Lupus erythematosus; Multiple sclerosis; Myasthenia gravis; Narcolepsy, Opsoclonus myoclonus syndrome (OMS); Optic neuritis; Ord's thyroiditis; Pemphigus; Pernicious anaemia; Polyarthritis in dogs; Primary biliary cirrhosis; Rheumatoid arthritis; Reiter's syndrome; Sjögren's syndrome; Takayasu's arteritis; Temporal arteritis (also known as "giant cell arteritis"); Warm autoimmune hemolytic anemia; Wegener's granulomatosis.

Other preferred eptiopes may be derived from antigens involved with maternal-foetal immunes responses, for example Rhesus D antigens involved in Rhesus D Haemolytic Disease of the Newborn.

Other preferred epitopes may be derived from antigens involved in graft-versus-host disease or transplant rejection (alloimmune responses), for example from MHC Class I molecules (otherwise referred to as human leukocyte antigens —HLA), preferably from the α3 domain and/or transmembrane domain of MHC Class I molecules, most preferably from the human MHC Class I molecule HLA-A2.

The epitopes may be of proteins which are administered to the individual, for example for therapy. Such proteins may act as neoantigens in the individual, such as for example in the situation where the individual does not express the protein. The therapeutic protein may be factor VIII, salcatonin or human growth hormone .

The following Examples illustrate the invention:

EXAMPLE 1

Peptides Derived from Human Leukocyte Antigens

The peptides in Table 2 derive from HLA-A2 and were identified by in silico analysis as containing MHC class II-binding T cell epitopes. Native sequences from HLA-A2 are in rows with a shaded background. Peptides marked with * were engineered to reduce dimer formation. Altered residues are shown in bold and underlined. Б =2-aminobutyric acid. The binding affinity of each peptide for different MHC class II molecules was then assessed in vitro by ELISA, as was the ability of the peptides to stimulate specific T cells.

TABLE 2

| TRA30  | H₂N | HAVSDHEATLRCWAL | COOH | SEQ ID NO: 1  |                        |
|--------|-----|-----------------|------|---------------|------------------------|
| TRA33* | H₂N | HAVSDHEATLRSWAL | COOH | SEQ ID NO: 2  | Engineered from TRA30  |
| TRA36* | H₂N | HAVSDHEATLRБWAL | COOH | SEQ ID NO: 3  | Engineered from TRA30  |
| TRA31  | H₂N | HPISDHEATLRCWAL | COOH | SEQ ID NO: 4  |                        |
| TRA34* | H₂N | HPISDHEATLRSWAL | COOH | SEQ ID NO: 5  | Engineered from TRA31  |
| TRA37* | H₂N | HPISDHEATLRБWAL | COOH | SEQ ID NO: 6  | Engineered from TRA31  |
| TRA32  | H₂N | HPVSDHEATLRCWAL | COOH | SEQ ID NO: 7  |                        |
| TRA35* | H₂N | HPVSDHEATLRSWAL | COOH | SEQ ID NO: 8  | Engineered from TRA32  |
| TRA38* | H₂N | HPVSDHEATLRБWAL | COOH | SEQ ID NO: 9  | Engineered from TRA32  |
| TRA39  | H₂N | RCWALSFYPAEITLT | COOH | SEQ ID NO: 10 |                        |
| TRA41* | H₂N | RSWALSFYPAEITLT | COOH | SEQ ID NO: 11 | Engineered from TRA39  |
| TRA40  | H₂N | RCWALGFYPAEITLT | COOH | SEQ ID NO: 12 |                        |
| TRA42* | H₂N | RSWALGFYPAEITLT | COOH | SEQ ID NO: 13 | Engineered from TRA40  |

Peptide TRA30 (HAVSDHEATLRCWAL—SEQ ID NO: 1) corresponds to amino acids 192-206 of HLA-A2 protein and is derived from the α3 domain of the HLA-A2 molecule. This peptide has a molecular weight of 1708. Peptide TRA31 (HPISDHEATLRCWAL—SEQ ID NO: 4) is an analogue of TRA30 and is also derived from the α3 domain of the HLA-A2 molecule, except that the alanine residue is replaced with a proline residue, and the valine residue is replaced with an isoleucine residue. TRA32 (HPVSDHEATLRCWAL—SEQ ID NO: 7) is another analogue of TRA30 and is also derived from the α3 domain of the HLA-A2 molecule, except that the alanine residue is replaced with a proline residue. Peptide TRA39 (RCWALSFYPAEITLT—SEQ ID NO: 10) corresponds to amino acids 202-216 of HLA-A2 protein, and is derived from the α3 domain of the HLA-A2 molecule. This peptide has a molecular weight of 1770. Peptide TRA 40 (RCWALGFYPAEITLT—SEQ ID NO: 12) is an analogue of TRA39, and is derived from the α3 domain of the HLA-A2 molecule, except that the serine residue at position 207 is replaced with a glycine residue.

All eight engineered peptides in Table 2 were engineered by the replacement of the cysteine residue with either serine or 2-aminobutyric acid (as shown) to reduce dimer formation and improve solubility. The following table illustrates the success of this strategy in that TRA33 and 36 have superior solubility to TRA 30, and TRA42 has superior solubility to TRA40.

| Peptide | Sequence (Single letter code) | Physicochemical properties ||||||
|---|---|---|---|---|---|---|---|
| | | Solubility mg/mL | Mw (Mono)* | Isoelectric point (pI)* | GRAVY* | Hydrophobic residues ||
| | | | | | | No. | % |
| TRA30 | HAVSDHEATLRCWAL | 7 | 1707.82 | 5.99 | -0.04 | 6 | 40% |
| TRA33 | HAVSDHEATLRSWAL | 8.5 | 1691.84 | 5.99 | -0.26 | 6 | 40% |
| TRA36 | HAVSDHEATLREWAL | 9.5 | 1689.43 | 5.99 | ND | 7 | 47% |
| TRA40 | RCWALGFYPAEITLT | NS, <0.7 | 1739.87 | 5.99 | 0.493 | 6 | 40% |
| TRA42 | RSWALGFYPAEITLT | 3.4 | 1723.89 | 6.00 | 0.273 | 6 | 40% |

Furthermore, some of the peptides above have been tested to determine whether modified peptides were more or less able to activate T cells than the original peptides. In particular, the peptides shown in the table below were tested against T cells from two subjects. The two subjects were renal transplant patients who were >1 yr post transplant and unselected for renal function. Subject 1 had a medium HLA peptide-specific T cell Elispot response whilst subject 2 had a very low Elispot response (see table below—original peptides are shaded grey).

The assay was performed as follows: Mononuclear cells are prepared from peripheral blood (PBMCs) of patients by ficoll gradient (30 mins). The PBMCs are incubated with peptides, positive control or negative control (medium only) in an Interferon gamma Elispot plate (48 hrs incubation). Following incubation, the Elispot plate is washed (30 mins) and the Anti-interferon gamma antibody-enzyme conjugate is added to Elispot plate (1.5 hr incubation). The Elispot plate is washed (30 mins) and the substrate is added to stain the Elispots (20 mins incubation). The plate is then read. The number of spots equates to the number of activated T cells.

As shown, in the subject (subject 1) with good responses, these were maintained when testing with modified peptides versus original peptides. Similarly, for the subject who did not respond to the original peptide (subject 2), modifying the peptides has not changed this. Thus, modification does not affect the ability of the peptides to activate T cells and in particular does not created a new false epitope. That is, engineering the peptides does not diminish their ability to induce an immune response.

EXAMPLE 2

Peptides Derived from House Dust Mite Allergens

| Peptide | Elispot count ||
|---|---|---|
| | Subject 1 | Subject 2 |
| TRA30 | 12.5 | 1.5 |
| TRA33 | 12.5 | 0.5 |
| TRA31 | 17.5 | 0.5 |
| TRA34 | 14 | 1.5 |
| TRA39 | 10.5 | 0.5 |
| TRA41 | 15.5 | 0 |
| TRA40 | 10.5 | 0.5 |
| TRA41 | 10.5 | 0 |

The peptides in Table 3 derive from major allergens from House Dust Mites and were identified by in silico analysis as containing MHC class II-binding T cell epitopes. Native sequences from House Dust Mite allergen proteins are in rows with a shaded background. Peptides marked with * were engineered to reduce dimer formation. Altered residues are shown in bold and underlined. B=2-aminobutyric acid. Binding affinity for each original peptide for different MHC class II molecules was assessed by in vitro binding studies.

TABLE 3

| | | | | | |
|---|---|---|---|---|---|
| HDM02 | H₂N | RTVTPIRMQGGCG | CO₂H | SEQ ID NO: 14 | |
| HDM02A* | H₂N | RTVTPIRMQGGSG | CO₂H | SEQ ID NO: 15 | Engineered from HDM02 |
| HDM02B* | H₂N | RTVTPIRMQGGBG | CO₂H | SEQ ID NO: 16 | Engineered from HDM02 |
| HDM03 | H₂N | RNQSLDLAEQELVDCASQH | CO₂H | SEQ ID NO: 17 | |
| HDM03D* | H₂N | RNQSLDLAEQELVDSASQH | CO₂H | SEQ ID NO: 18 | Engineered from HDM03 |
| HDM03E* | H₂N | RNQSLDLAEQELVDBASQH | CO₂H | SEQ ID NO: 19 | Engineered from HDM03 |
| HDM03Wa | H₂N | ELVDCASQHG | CO₂H | SEQ ID NO: 35 | |
| HDM03W | H₂N | ELVDSASQHG | CO₂H | SEQ ID NO: 36 | Engineered from HDM03Wa |
| HDM03Wb | H₂N | ELVDBASQHG | CO₂H | SEQ ID NO: 61 | Engineered from HDM03Wa |
| HDM06A | H₂N | RYVAREQSCRRP | CO₂H | SEQ ID NO: 20 | |
| HDM06A* | H₂N | RYVAREQSSRRP | CO₂H | SEQ ID NO: 21 | Engineered from HDM06 |
| HDM06B* | H₂N | RYVAREQSBRRP | CO₂H | SEQ ID NO: 22 | Engineered from HDM06 |
| HDM19 | H₂N | DQVDVKDCANHEIKK | CO₂H | SEQ ID NO: 23 | |
| HDM19A* | H₂N | DQVDVKDSANHEIKK | CO₂H | SEQ ID NO: 24 | Engineered from HDM19 |
| HDM19B* | H₂N | DQVDVKDBANHEIKK | CO₂H | SEQ ID NO: 25 | Engineered from HDM19 |
| HDM26 | H₂N | GVLACAIATHAKIR | CO₂H | SEQ ID NO: 26 | |
| HDM26B* | H₂N | GVLASAIATHAKIR | CO₂H | SEQ ID NO: 27 | Engineered from HDM26 |
| HDM26C* | H₂N | GVLABAIATHAKIR | CO₂H | SEQ ID NO: 28 | Engineered from HDM26 |
| HDM100 | H₂N | RFGISNYCQIYPPNVNK | CO₂H | SEQ ID NO: 29 | |
| HDM100A* | H₂N | RFGISNYSQIYPPNVNK | CO₂H | SEQ ID NO: 54 | Engineered from HDM100 |
| HDM100B* | H₂N | RFGISNYBQIYPPNVNK | CO₂H | SEQ ID NO: 30 | Engineered from HDM100 |
| HDM101 | H₂N | NYCQIYPPNVNKIREA | CO₂H | SEQ ID NO: 31 | |
| HDM101A* | H₂N | NYSQIYPPNVNKIREA | CO₂H | SEQ ID NO: 55 | Engineered from HDM101 |
| HDM101B* | H₂N | NYBQIYPPNVNKIREA | CO₂H | SEQ ID NO: 32 | Engineered from HDM101 |
| HDM102 | H₂N | NAQRFGISNYCQI | CO₂H | SEQ ID NO: 33 | |
| HDM102A* | H₂N | NAQRFGISNYSQI | CO₂H | SEQ ID NO: 56 | Engineered from HDM102 |
| HDM102B* | H₂N | NAQRFGISNYBQI | CO₂H | SEQ ID NO: 34 | Engineered from HDM102 |
| HDM203A | H₂N | DLRQMRTVTPIRMQGGCGS | CO₂H | SEQ ID NO: 57 | |
| HDM203B* | H₂N | DLRQMRTVTPIRMQGGSGS | CO₂H | SEQ ID NO: 58 | Engineered from HDM203A |

Peptides HDM02, HDM03, HDM06, HDM100, 101, 102 and 203 derive from the major dust mite allergen Der p1. Peptides HDM19 and HDM26 derive from the major dust mite allergen Der p2. All the engineered peptides in Table 3 were engineered by the replacement of the cysteine residue with either serine or 2-aminobutyric acid (as shown) to reduce dimer formation.

The suitability of several of the above engineered peptides for use in tolerisation to treat or prevent house dust mite allergy is demonstrated below. The following Table presents results from a cytokine release assay performed on PBMCs taken from a population of house dust mite allergic individuals (N=number of individuals in population). A positive response is considered to be production of at least 100 pg/ml of cytokine. As shown, the number of individuals in the population who produce the cytokines IFN-γ and IL-13 in response to the peptides indicated is not significantly altered by the engineering process. Thus, engineering the peptides does not diminish their ability to induce an immune response.

Cytokine secretion profiles from PBMC's were analysed in response to the peptide stimulation using the peptides indicated. Supernatants from the cytokine release assay were tested for the presence of 2 cytokines, IFN-γ and IL-13, using either an ELISA assay or a multiplex bead array assay.

A typical cytokine release assay requires 40×10⁶ PBMC's per subject. In more detail, 250 μl of a 200 μg/ml solution of the appropriate antigen or peptide concentration is distributed into the appropriate wells of 48 well plates. Plates are the incubated in a humidified 5% CO₂ incubator at 37° C. for a maximum of 4 hours. 250 μl of a 5×10⁶ cell/ml PBMC suspension is then added to each well and the plates returned to the incubator for 5 days. Following stimulation, samples of culture supernatant are harvested for testing by ELISA or multiplex bead assay according to standard protocols.

| Peptide | Sequence | Responders with IFN-g >100 | Responders with IL-13 >100 |
|---|---|---|---|
| N = 55 | | | |
| HDM101 | NYCQIYPPNVNKIREA | 2 | 1 |
| HDM101A | NYSQIYPPNVNKIREA | 4 | 4 |
| HDM101B | NYBQIYPPNVNKIREA | 1 | 2 |
| HDM102 | NAQRFGISNYCQI | 16 | 13 |
| HDM102A | NAQRFGISNYSQI | 14 | 16 |
| HDM102B | NAQRFGISNYBQI | 15 | 17 |
| HDM100 | RFGISNYCQIYPPNVNK | 6 | 6 |
| HDM100A | RFGISNYSQIYPPNVNK | 10 | 8 |
| HDM100B | RFGISNYBQIYPPNVNK | 6 | 10 |

FIG. 1 shows the results of a similar assay for IL10 production in response to HDM203A and 203B in a population of 34 house dust mite allergic individuals. Once again, the responses of all individuals were not significantly different in the engineered versus non-engineered peptides.

EXAMPLE 3

Peptides Derived from Ragweed Allergens

The peptides below derive from the major allergen in Ragweed pollen (Amb a 1, NCBI Acc. No. AAA32669) and were identified by in silico analysis as containing MHC class II-binding T cell epitopes. Native sequences from ragweed allergen proteins are in rows with a shaded background. Peptides marked with * were engineered to reduce dimer formation. Altered residues are shown in bold and underlined. Binding affinity for each original peptide for different MHC class II molecules was assessed by in vitro binding studies.

| | | | | | |
|---|---|---|---|---|---|
| RGW02A | $H_2N$ | GSSQIWIDHCSLSKA | $CO_2H$ | SEQ ID NO: 59 | |
| RGW02* | $H_2N$ | GSSQIWIDHSSLSKS | $CO_2H$ | SEQ ID NO: 60 | Engineered from RGW02B |

Using methods equivalent to those in Example 2, these peptides were tested for the ability to induce cytokine production in PBMCs taken from a population of ragweed allergic individuals. The levels of IFN-gamma produced by each subject are shown in FIG. 2. As is shown, the engineered peptide (RGW02) does not induce significantly different responses to the non-engineered peptide (RGW02B).

Accordingly the engineered peptide is suitable for use in tolerisation for treatment or prevention of ragweed pollen allergy.

An equivalent substitution could be made with 2 aminobutyric acid to give RGW02c: GSSQIWIDB SLSKS (SEQ ID NO. 72).

The suitability of several of the above engineered peptides for use in tolerisation to treat or prevent ragweed allergy is demonstrated below. The following Table presents results from a cytokine release assay performed on PBMCs taken from seven ragweed allergic individuals (A-G). As shown, the level of production of IL-10 by the modified peptide (RGW02) is not significantly different to the level produced by the original peptide (RGW02A) Thus, engineering the peptide does not diminish its ability to induce an immune response.

Cytokine secretion profiles from PBMC's were analysed in response to the peptide stimulation using the peptide indicated. Supernatants from the cytokine release assay were tested for the presence of IL-10, using either an ELISA assay or a multiplex bead array assay.

A typical cytokine release assay requires $40\times10^6$ PBMC's per subject. In more detail, 250 μl of a 200 μg/ml solution of the appropriate antigen or peptide concentration is distributed into the appropriate wells of 48 well plates. Plates are the incubated in a humidified 5% $CO_2$ incubator at 37° C. for a maximum of 4 hours. 250 μl of a $5\times10^6$ cell/ml PBMC suspension is then added to each well and the plates returned to the incubator for 5 days. Following stimulation, samples of culture supernatant are harvested for testing by ELISA or multiplex bead assay according to standard protocols.

| Subject | Peptide | IL-10 (pg/ml) |
|---|---|---|
| A | RGW02 | 248.91 |
| A | RGW02A | 255.52 |
| B | RGW02 | 227.18 |
| B | RGW02A | 224.34 |
| C | RGW02 | 452.45 |
| C | RGW02A | 486.75 |
| D | RGW02 | 80.54 |
| D | RGW02A | 67.40 |
| E | RGW02 | 310.34 |
| E | RGW02A | 323.84 |
| F | RGW02 | 203.12 |
| F | RGW02A | 225.41 |
| G | RGW02 | 283.75 |
| G | RGW02A | 240.41 |

EXAMPLE 4

Peptides Derived from Cat Allergens

The peptides in Table 4 derive from the major cat allergen Fel d1, identified by in vitro analysis as containing MHC class II-binding T cell epitopes. Each of the five peptides contains a single cysteine residue, the side-chain of which contains a thiol functional group. Although free thiols can exist in the free state, they are readily oxidised to form intermolecular disulphide bridges or cystine residues. Oxidation of the cysteine residues present in the peptides will result in the formation of dimers. These dimers may arise due to crosslinking of two peptides with the same sequence in individual formulations, or different peptides within a mixture.

While individual peptides have a maximum chain length of 17 amino acids, dimerization will result in larger molecules that could trigger mast cell degranulation with a concomitant release of histamine. Obviously this is undesirable, but the presence of cysteine residues in some of the selected peptides may result in this effect being observed.

Consequently, the primary focus of this Example was to assess the ability of each agent or mixture of agents, to reduce or inhibit the formation of peptide dimers arising through the oxidation of free thiols to form intermolecular disulphide bridges. The output of the Example is the identification of agents which may be included in a formulation or composition of each of the individual peptides to reduce dimer formation.

TABLE 4

| Peptide | Amino acid sequence[a] | Molecular weight (Da) | Isoelectric point[a] | |
|---|---|---|---|---|
| MLA01 | CPAVKRDVDLFLT | 1476.77 | 5.95 | SEQ ID NO: 37 |
| MLA04 | KALPVVLENARILKNCV | 1880.35 | 9.31 | SEQ ID NO: 38 |
| MLA05 | RILKNCVDAKMTEEDKE | 2022.34 | 5.11 | SEQ ID NO: 39 |
| MLA12 | TAMKKIQDCYVENGLI | 1826.18 | 5.73 | SEQ ID NO: 40 |
| MLA15 | ISSSKDCMGEAVQNTV | 1668.88 | 4.37 | SEQ ID NO: 41 |

[a]Data generated from primary sequence information using ProtParam tool at the ExPASy Molecular Biology Server (http://www.expasy.org)

These sequences may also be engineered to replace cysteine residues as described above. Thus:

| MLA01a | SPAVKRDVDLFLT | SEQ ID NO: 62 |
| MLA01b | BPAVKRDVDLFLT | SEQ ID NO: 63 |
| MLA04a | KALPVVLENARILKNSV | SEQ ID NO: 64 |
| MLA04b | KALPVVLENARILKNBV | SEQ ID NO: 65 |
| MLA05a | RILKNSVDAKMTEEDKE | SEQ ID NO: 66 |
| MLA05b | RILKNBVDAKMTEEDKE | SEQ ID NO: 67 |
| MLA12a | TAMKKIQDSYVENGLI | SEQ ID NO: 68 |
| MLA12b | TAMKKIQDBYVENGLI | SEQ ID NO: 69 |
| MLA15a | ISSSKDSMGEAVQNTV | SEQ ID NO: 70 |
| MLA15b | ISSSKDBMGEAVQNTV | SEQ ID NO: 71 |

The engineered peptides are not tested further in this Example.

Methods

The peptides used in this study have a minimum purity of >90%. The effectiveness of each additive to reduce dimer formation was assessed by size exclusion chromatography (SEC) and RP-HPLC. In SEC, molecules are separated based upon their apparent molecular weight. Smaller molecules can distribute into a greater proportion of the column matrix and are retained for longer than analytes of higher molecular weight. Dimers will elute from the column with an apparent molecular weight approximately twice that of the corresponding monomers. Separation by RP-HPLC separates species based on differences in their hydrophobicities. The amount of dimer formed is determined as a percentage of the total peak area ratio (% PAR) for the chromatogram.

Basic Formulations

Studies were conducted using a universal matrix into which each of the potential agents were added to the appropriate concentration. The universal matrix was prepared in deionised water and contained
  5 mM hydrochloric acid (HCl)
  140 mM sodium chloride (NaCl)

The 5 mM HCl was utilised to provide a low pH environment, i.e. ca. pH 2.3. At low pH the free thiol groups will be fully protonated and as such are much less susceptible to oxidation than at pH>6. The low pH provides an environment that promotes the solubility of each of the peptides. At pH 2.3 all the peptides should exhibit cationic properties, i.e. be positively charged, and therefore should be soluble to some extent. HCl has been used at concentration of up to 10% v/v in intravenous injections.

NaCl was included at 140 mM to produce a matrix with an ionic strength roughly equivalent to the physiological environment, i.e. isotonic. Since the peptides will be administered intradermally during Clinical studies it is important that the formulations used are close to isotonic. It is expected that similar effects would be observed in low tonicity matrices.

Agents Tested

The agents added to the universal matrix are shown in Table 5 together with the concentrations at which they were used.

TABLE 5

| Agent | Concentration in universal matrix (% w/v) | Properties |
|---|---|---|
| Control | N/A | N/A |
| Ascorbic acid | 1.0 | Antioxidant |
| Butylated hydroxyanisole (BHA) | 0.002 | Antioxidant, Preservative |
| Butylated hydroxytoluene (BHT) | 0.002 | Antioxidant, Preservative |
| Sodium metabisulphite | 1.0 | Antioxidant |
| Sodium thiosulphate | 0.1 | Antioxidant |
| Cysteine hydrochloride | 0.5 | Antioxidant, Reducing agent |
| L-Methionine hydrochloride | 0.5 | Antioxidant, Reducing agent |
| 1-Thioglycerol | 0.5 | Antioxidant, Preservative |
| Thioglycollic acid | 0.2 | Reducing agent |
| Sodium citrate | 1.0 | Chelating agent |
| Disodium EDTA | 1.0 | Chelating agent |
| Mixture 1 | | |
| Disodium EDTA | 1.0 | |
| Methionine | 0.5 | |
| BHA | 0.002 | |
| Mixture 2 | | |
| Disodium EDTA | 1.0 | |
| Thioglycerol | 0.5 | |
| BHA | 0.002 | |

Results

The level of dimer formation in the presence of each agent is shown in Table 6. Agents which successfully reduced dimer formation are highlighted in bold.

TABLE 6

| | | Percentage dimer formation (% PAR) | | | | | | |
|---|---|---|---|---|---|---|---|---|
| | | 72 hrs | | 1 week | | 2 weeks | | 5 weeks |
| Additive | T = 0 | 25° C./ 60% RH | 5° C. | 25° C./ 60% RH | 5° C. | 25° C./ 60% RH | −20° C. | 5° C. |
| Control | 1.16 | 6.52 | 3.20 | 8.72 | 3.23 | 11.43 | 2.42 | 7.51 |
| Ascorbic acid | 0.14 | 1.76 | 0.53 | 5.62 | ND | ND | ND | ND |
| BHA | 1.56 | 8.80 | 4.38 | 10.10 | ND | ND | ND | ND |
| BHT | 1.25 | 11.48 | 7.13 | 12.67 | ND | ND | ND | ND |
| Na metabisulphite | 0.32 | 0.12 | 2.49 | 1.41 | ND | ND | ND | ND |
| Na thiosulphate | —* | —* | —* | —* | ND | ND | ND | ND |
| Cysteine HCl | 0.35 | 0.18 | 0.38 | 0.24 | 0.02 | 0.02 | 0.23 | 0.69 |
| DL-Methionine | 1.20 | 3.78 | 2.01 | 6.70 | ND | ND | ND | ND |
| 1-Thioglycerol | 0.22 | 0.46 | 0.63 | 0.36 | 0.35 | 0.37 | 0.38 | 1.43 |
| Na citrate | 43.82 | 43.48 | 43.86 | 42.95 | ND | ND | ND | ND |
| Disodium EDTA | 1.26 | 4.64 | 7.27 | 12.60 | ND | ND | ND | ND |
| Mix 1 BHA EDTA DL-Methionine | 6.44 | 16.87 | 22.76 | 20.24 | ND | ND | ND | ND |
| Mix 2 BHA EDTA 1-Thioglycerol | 0.60 | 0.29 | 0.70 | 0.67 | 1.67 | 1.29 | 0.33 | 2.08 |

—* Not available due to unusual chromatography
ND None detected
RH Relative humidity The data generated by size exclusion chromatography on samples prepared as above and stored for up to one week identified two agents, 1-Thioglycerol and Cysteine hydrochloride, as being effective at preventing peptide dimer formation. In addition, a mixture of agents, i.e. EDTA, BHA and 1-Thioglycerol (Mix 2), also appeared to prevent dimer formation. Of the remaining agents ascorbic acid and DL-Methionine appear to retard dimer formation compared to the control matrix, i.e. 5 mM HCl and 140 mM NaCl, but the presence of the other additives resulted in increased dimer formation.

Evaluation of dimer content was continued for the peptide mixtures prepared in the Control matrix and the matrices containing 1-Thioglycerol, L-Cysteine hydrochloride and Mix 2 at two week and five week timepoints under the conditions as shown in Table 6.

Following the generation of data from the preliminary screening a further piece of work was undertaken to evaluate the ability of matrices containing Cysteine hydrochloride and 1-thioglycerol to inhibit the propensity of individual cysteine containing peptides and mixed pairs of these peptides to dimerize compared to the matrix alone. For each excipient mixtures of all the possible binary peptide combinations were prepared. Samples were analysed by RP-HPLC immediately and after storage at 25° C./60% RH for one week. The amounts of dimer formed are presented in Table 7. The amount of dimer formed is determined as a percentage of the total peak area ratio (% PAR) for the chromatogram in each case.

The effectiveness of Cysteine hydrochloride in preventing dimerization is considered to proceed through the formation of cysteinylated peptides.

TABLE 7

| | | Percentage peak area ratio (% PAR) | | | | | | | | |
|---|---|---|---|---|---|---|---|---|---|---|
| | | T = 0 | | | T = 72 h | | | T = 1 week | | |
| Peptide(s) in sample | Dimers formed | Control | Cysteine | 1-Thioglycerol | Control | Cysteine | 1-Thioglycerol | Control | Cysteine | 1-Thioglycerol |
| MLA01 | MLA01 | 3.85 | 0.49 | ND | 43.81 | ND | ND | 66.81 | ND | ND |
| MLA04 | MLA04 | ND | ND | ND | 2.51 | ND | ND | 4.76 | ND | ND |
| MLA05 | MLA05 | 0.55 | ND | ND | 1.99 | ND | ND | 1.65 | 0.21 | ND |
| MLA12 | MLA12 | ND | ND | ND | 0.46 | ND | ND | 1.72 | ND | ND |
| MLA01 | MLA01 | 2.92 | 0.48 | ND | 35.47 | ND | ND | 39.49 | 0.52 | ND |
| MLA04 | MLA04 | ND | ND | ND | 1.32 | ND | ND | 2.71 | ND | ND |
| | MLA01 + 04 | ND | ND | ND | 10.84 | ND | ND | 18.44 | 0.61 | ND |
| MLA01 | MLA01 | 2.73 | 0.73 | ND | 41.11 | ND | ND | 45.59 | 0.26 | ND |
| MLA05 | MLA05 | 0.35 | ND | ND | 2.21 | ND | ND | 3.18 | ND | ND |
| | MLA01 + 05 | 0.67 | ND | ND | 14.2 | ND | ND | 18.35 | 0.25 | ND |
| MLA01 | MLA01 | 2.7 | 0.2 | ND | 29.62 | ND | ND | 40.03 | 0.23 | ND |
| MLA12 | MLA12 | ND | ND | ND | 2.09 | 0.1 | ND | 3.43 | 0.18 | ND |
| | MLA01 + 12 | 0.23 | ND | ND | 9.92 | 0.28 | ND | 17.19 | 0.51 | ND |
| MLA04 | MLA04 | ND | ND | ND | 0.91 | ND | ND | 2.32 | ND | ND |
| MLA05 | MLA05 | ND | ND | ND | 2.25 | ND | ND | 3.26 | ND | ND |
| | MLA04 + 05 | ND | ND | ND | 2.59 | 0.29 | ND | 6.1 | 1.42 | ND |
| MLA04 | MLA04 | ND | ND | ND | 0.44 | ND | ND | 2.42 | ND | ND |

TABLE 7-continued

| Peptide(s) in sample | Dimers formed | Percentage peak area ratio (% PAR) | | | | | | | | |
|---|---|---|---|---|---|---|---|---|---|---|
| | | T = 0 | | | T = 72 h | | | T = 1 week | | |
| | | Control | Cysteine | 1-Thioglycerol | Control | Cysteine | 1-Thioglycerol | Control | Cysteine | 1-Thioglycerol |
| MLA12 | MLA12 | ND | ND | ND | 1.1 | 0.33 | ND | 2.13 | 0.32 | ND |
| | MLA04 + 12 | ND | ND | ND | 2.38 | ND | ND | 6.28 | ND | ND |
| MLA05 | MLA05 | ND | ND | ND | 8.17 | ND | ND | 1.85 | ND | ND |
| MLA12 | MLA12 | ND | ND | ND | 9.78 | ND | ND | 1.28 | ND | ND |
| | MLA05 + 12 | ND | 1.49 | ND | 20.9 | 10.48 | 0.28 | 4.4 | 17.85 | 0.97 |

ND None detected

EXAMPLE 4

Peptides Derived from Proteins Associated with Auto- and Allo-Immune Diseases All of the peptides in tables 8, 9 and 10 derive from proteins associated with allo-immune diseases as indicated, and were previously identified by in silico or in vitro analysis as containing MHC class II-binding T cell epitopes. Native sequences from the proteins are in rows with a shaded background. Peptides marked with * were engineered to reduce dimer formation. Altered residues are shown in bold and underlined.

TABLE 8

Neonatal Alloimmune Thrombocytopenia

| NAIT01 | H₂N AWCSDEALPL COOH | SEQ ID NO: 40 |
|---|---|---|
| NAIT01A* | H₂N AWSSDEALPL COOH | SEQ ID NO: 41 Engineered from NAIT01 |

Derived from platelet glycoprotein IIIa

TABLE 9

Haemolytic Disease of the Newborn

| HDN28 | H₂N AYFGLSVAWCLPKPL COOH | SEQ ID NO: 42 |
|---|---|---|
| HDN28* | H₂N AYFGLSVAWSLPKPL COOH | SEQ ID NO: 43 Engineered from HDN28 |

Derived from Rhesus blood group D antigen

TABLE 10

Alloimmune Thrombocytopenia

| AIT02 | H₂N TTRGVSSCQQCLAVS COOH | SEQ ID NO: 44 |
|---|---|---|
| AIT02A* | H₂N TTRGVSSSQQSLAVS COON | SEQ ID NO: 45 Engineered from AIT02 |
| AIT47 | H₂N DLPEELSLSFNATCL COOH | SEQ ID NO: 46 |
| AIT47A* | H₂N DLPEELSLSFNATSL COOH | SEQ ID NO: 47 Engineered from AIT47 |
| AIT53 | H₂N FKDSLIVQVTFDCDC COOH | SEQ ID NO: 48 |
| AIT53A* | H₂N FKDSLIVQVTFDSDS COOH | SEQ ID NO: 49 Engineered from AIT53 |
| AIT70 | H₂N PGSYEDTCEKCPTCP COOH | SEQ ID NO: 50 |
| AIT70A* | H₂N PGSYEDTSEKSPTSP COON | SEQ ID NO: 51 Engineered from AIT70 |
| AIT77 | H₂N DDCVVRFQYYEDSSG COOH | SEQ ID NO: 52 |
| AIT77A* | H₂N DDSVVRFQYYEDSSG COOH | SEQ ID NO: 53 Engineered from AIT77 |

Derived from platelet glycoprotein IIIa

The invention claimed is:

1. A composition comprising:

i) at least one peptide of up to 25 amino acids in length which comprises or consists of the sequence corresponding to any one of SEQ ID NO: 37 (MLA01), SEQ ID NO: 38 (MLA04), SEQ ID NO: 39 (MLA05), or SEQ ID NO: 40 (MLA12); and ii) at least one agent which inhibits peptide dimer formation and which is selected from thioglycerol and thioanisole.

2. A composition according to claim 1, comprising at least a first and a second peptide, wherein the first and second peptide each comprise or consist of a different comprise or consist of the sequences corresponding to:t sequence selected from the sequences of SEQ ID NO: 37 (MLA01), SEQ ID NO: 38 (MLA04), SEQ ID NO: 39 (MLA05), or SEQ ID NO: 40 (MLA12).

3. A composition according to claim 2, wherein the first and second peptides comprise or consist of the sequences corresponding to:
a) SEQ ID NOS: 37 (MLA01) and 38 (MLA04);
b) SEQ ID NOS: 37 (MLA01) and 39 (MLA05);
c) SEQ ID NOS: 37 (MLA01) and 40 (MLA12);
d) SEQ ID NOS: 38 (MLA04) and 39 (MLA05);
e) SEQ ID NOS: 38 (MLA04) and 40 (MLA12); or
f) SEQ ID NOS: 39 (MLA05) and 40 (MLA12), respectively.

4. A composition according to claim 1, wherein the agent is thioglycerol.

* * * * *

SEQUENCE LISTING

<160> NUMBER OF SEQ ID NOS: 177

<210> SEQ ID NO 1
<211> LENGTH: 15
<212> TYPE: PRT
<213> ORGANISM: Homo sapiens

<400> SEQUENCE: 1

His Ala Val Ser Asp His Glu Ala Thr Leu Arg Cys Trp Ala Leu
1               5                   10                  15

```
<210> SEQ ID NO 2
<211> LENGTH: 15
<212> TYPE: PRT
<213> ORGANISM: Artificial sequence
<220> FEATURE:
<223> OTHER INFORMATION: TRA33* synthetic peptide

<400> SEQUENCE: 2

His Ala Val Ser Asp His Glu Ala Thr Leu Arg Ser Trp Ala Leu
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: TRA36* synthetic peptide
<220> FEATURE:
<221> NAME/KEY: MOD_RES
<222> LOCATION: (12)..(12)
<223> OTHER INFORMATION: Xaa = Abu

<400> SEQUENCE: 3

His Ala Val Ser Asp His Glu Ala Thr Leu Arg Xaa Trp Ala Leu
1               5                   10                  15

<210> SEQ ID NO 4
<211> LENGTH: 15
<212> TYPE: PRT
<213> ORGANISM: Homo sapiens

<400> SEQUENCE: 4

His Pro Ile Ser Asp His Glu Ala Thr Leu Arg Cys Trp Ala Leu
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: TRA34* synthetic peptide

<400> SEQUENCE: 5

His Pro Ile Ser Asp His Glu Ala Thr Leu Arg Ser Trp Ala Leu
1               5                   10                  15

<210> SEQ ID NO 6
<211> LENGTH: 15
<212> TYPE: PRT
<213> ORGANISM: Artificial sequence
<220> FEATURE:
<223> OTHER INFORMATION: TRA37* synthetic peptide
<220> FEATURE:
<221> NAME/KEY: MOD_RES
<222> LOCATION: (12)..(12)
<223> OTHER INFORMATION: Xaa = Abu

<400> SEQUENCE: 6

His Pro Ile Ser Asp His Glu Ala Thr Leu Arg Xaa Trp Ala Leu
1               5                   10                  15

<210> SEQ ID NO 7
<211> LENGTH: 15
<212> TYPE: PRT
<213> ORGANISM: Homo sapiens

<400> SEQUENCE: 7
```

```
His Pro Val Ser Asp His Glu Ala Thr Leu Arg Cys Trp Ala Leu
1               5                   10                  15
```

<210> SEQ ID NO 8
<211> LENGTH: 15
<212> TYPE: PRT
<213> ORGANISM: Artificial sequence
<220> FEATURE:
<223> OTHER INFORMATION: TRA35* synthetic peptide

<400> SEQUENCE: 8

```
His Pro Val Ser Asp His Glu Ala Thr Leu Arg Ser Trp Ala Leu
1               5                   10                  15
```

<210> SEQ ID NO 9
<211> LENGTH: 15
<212> TYPE: PRT
<213> ORGANISM: Artificial sequence
<220> FEATURE:
<223> OTHER INFORMATION: TRA38* synthetic peptide
<220> FEATURE:
<221> NAME/KEY: MOD_RES
<222> LOCATION: (12)..(12)
<223> OTHER INFORMATION: Xaa = Abu

<400> SEQUENCE: 9

```
His Pro Val Ser Asp His Glu Ala Thr Leu Arg Xaa Trp Ala Leu
1               5                   10                  15
```

<210> SEQ ID NO 10
<211> LENGTH: 15
<212> TYPE: PRT
<213> ORGANISM: Homo sapiens

<400> SEQUENCE: 10

```
Arg Cys Trp Ala Leu Ser Phe Tyr Pro Ala Glu Ile Thr Leu Thr
1               5                   10                  15
```

<210> SEQ ID NO 11
<211> LENGTH: 15
<212> TYPE: PRT
<213> ORGANISM: Artificial sequence
<220> FEATURE:
<223> OTHER INFORMATION: TRA41* synthetic peptide

<400> SEQUENCE: 11

```
Arg Ser Trp Ala Leu Ser Phe Tyr Pro Ala Glu Ile Thr Leu Thr
1               5                   10                  15
```

<210> SEQ ID NO 12
<211> LENGTH: 15
<212> TYPE: PRT
<213> ORGANISM: Homo sapiens

<400> SEQUENCE: 12

```
Arg Cys Trp Ala Leu Gly Phe Tyr Pro Ala Glu Ile Thr Leu Thr
1               5                   10                  15
```

<210> SEQ ID NO 13
<211> LENGTH: 15
<212> TYPE: PRT
<213> ORGANISM: Artificial sequence
<220> FEATURE:
<223> OTHER INFORMATION: TRA42* synthetic peptide

<400> SEQUENCE: 13

```
Arg Ser Trp Ala Leu Gly Phe Tyr Pro Ala Glu Ile Thr Leu Thr
1               5                   10                  15
```

-continued

```
<210> SEQ ID NO 14
<211> LENGTH: 13
<212> TYPE: PRT
<213> ORGANISM: Dermatophagoides pteronyssinus

<400> SEQUENCE: 14

Arg Thr Val Thr Pro Ile Arg Met Gln Gly Gly Cys Gly
1               5                   10

<210> SEQ ID NO 15
<211> LENGTH: 13
<212> TYPE: PRT
<213> ORGANISM: Artificial sequence
<220> FEATURE:
<223> OTHER INFORMATION: HDM02A* synthetic peptide

<400> SEQUENCE: 15

Arg Thr Val Thr Pro Ile Arg Met Gln Gly Gly Ser Gly
1               5                   10

<210> SEQ ID NO 16
<211> LENGTH: 13
<212> TYPE: PRT
<213> ORGANISM: Artificial sequence
<220> FEATURE:
<223> OTHER INFORMATION: HDM02B* synthetic peptide
<220> FEATURE:
<221> NAME/KEY: MOD_RES
<222> LOCATION: (12)..(12)
<223> OTHER INFORMATION: Xaa = Abu

<400> SEQUENCE: 16

Arg Thr Val Thr Pro Ile Arg Met Gln Gly Gly Xaa Gly
1               5                   10

<210> SEQ ID NO 17
<211> LENGTH: 19
<212> TYPE: PRT
<213> ORGANISM: Dermatophagoides pteronyssinus

<400> SEQUENCE: 17

Arg Asn Gln Ser Leu Asp Leu Ala Glu Gln Glu Leu Val Asp Cys Ala
1               5                   10                  15

Ser Gln His

<210> SEQ ID NO 18
<211> LENGTH: 19
<212> TYPE: PRT
<213> ORGANISM: Artificial sequence
<220> FEATURE:
<223> OTHER INFORMATION: HDM03D* synthetic peptide

<400> SEQUENCE: 18

Arg Asn Gln Ser Leu Asp Leu Ala Glu Gln Glu Leu Val Asp Ser Ala
1               5                   10                  15

Ser Gln His

<210> SEQ ID NO 19
<211> LENGTH: 19
<212> TYPE: PRT
<213> ORGANISM: Artificial sequence
<220> FEATURE:
<223> OTHER INFORMATION: HDM03E* synthetic peptide
<220> FEATURE:
<221> NAME/KEY: MOD_RES
<222> LOCATION: (15)..(15)
```

```
<223> OTHER INFORMATION: Xaa = Abu

<400> SEQUENCE: 19

Arg Asn Gln Ser Leu Asp Leu Ala Glu Gln Glu Leu Val Asp Xaa Ala
1               5                   10                  15

Ser Gln His

<210> SEQ ID NO 20
<211> LENGTH: 12
<212> TYPE: PRT
<213> ORGANISM: Dermatophagoides pteronyssinus

<400> SEQUENCE: 20

Arg Tyr Val Ala Arg Glu Gln Ser Cys Arg Arg Pro
1               5                   10

<210> SEQ ID NO 21
<211> LENGTH: 12
<212> TYPE: PRT
<213> ORGANISM: Artificial sequence
<220> FEATURE:
<223> OTHER INFORMATION: HDM06A* synthetic peptide

<400> SEQUENCE: 21

Arg Tyr Val Ala Arg Glu Gln Ser Ser Arg Arg Pro
1               5                   10

<210> SEQ ID NO 22
<211> LENGTH: 12
<212> TYPE: PRT
<213> ORGANISM: Artificial sequence
<220> FEATURE:
<223> OTHER INFORMATION: HDM06B* synthetic peptide
<220> FEATURE:
<221> NAME/KEY: MOD_RES
<222> LOCATION: (9)..(9)
<223> OTHER INFORMATION: Xaa = Abu

<400> SEQUENCE: 22

Arg Tyr Val Ala Arg Glu Gln Ser Xaa Arg Arg Pro
1               5                   10

<210> SEQ ID NO 23
<211> LENGTH: 15
<212> TYPE: PRT
<213> ORGANISM: Dermatophagoides pteronyssinus

<400> SEQUENCE: 23

Asp Gln Val Asp Val Lys Asp Cys Ala Asn His Glu Ile Lys Lys
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: HDM19A* synthetic peptide

<400> SEQUENCE: 24

Asp Gln Val Asp Val Lys Asp Ser Ala Asn His Glu Ile Lys Lys
1               5                   10                  15

<210> SEQ ID NO 25
<211> LENGTH: 15
<212> TYPE: PRT
<213> ORGANISM: Artificial sequence
<220> FEATURE:
```

-continued

```
<223> OTHER INFORMATION: HDM19B* synthetic peptide
<220> FEATURE:
<221> NAME/KEY: MOD_RES
<222> LOCATION: (8)..(8)
<223> OTHER INFORMATION: Xaa = Abu

<400> SEQUENCE: 25

Asp Gln Val Asp Val Lys Asp Xaa Ala Asn His Glu Ile Lys Lys
1               5                   10                  15

<210> SEQ ID NO 26
<211> LENGTH: 14
<212> TYPE: PRT
<213> ORGANISM: Dermatophagoides pteronyssinus

<400> SEQUENCE: 26

Gly Val Leu Ala Cys Ala Ile Ala Thr His Ala Lys Ile Arg
1               5                   10

<210> SEQ ID NO 27
<211> LENGTH: 14
<212> TYPE: PRT
<213> ORGANISM: Artificial sequence
<220> FEATURE:
<223> OTHER INFORMATION: HDM26B* synthetic peptide

<400> SEQUENCE: 27

Gly Val Leu Ala Ser Ala Ile Ala Thr His Ala Lys Ile Arg
1               5                   10

<210> SEQ ID NO 28
<211> LENGTH: 14
<212> TYPE: PRT
<213> ORGANISM: Artificial sequence
<220> FEATURE:
<223> OTHER INFORMATION: HDM26C* synthetic peptide
<220> FEATURE:
<221> NAME/KEY: MOD_RES
<222> LOCATION: (5)..(5)
<223> OTHER INFORMATION: Xaa = Abu

<400> SEQUENCE: 28

Gly Val Leu Ala Xaa Ala Ile Ala Thr His Ala Lys Ile Arg
1               5                   10

<210> SEQ ID NO 29
<211> LENGTH: 17
<212> TYPE: PRT
<213> ORGANISM: Dermatophagoides pteronyssinus

<400> SEQUENCE: 29

Arg Phe Gly Ile Ser Asn Tyr Cys Gln Ile Tyr Pro Pro Asn Val Asn
1               5                   10                  15

Lys

<210> SEQ ID NO 30
<211> LENGTH: 17
<212> TYPE: PRT
<213> ORGANISM: Artificial sequence
<220> FEATURE:
<223> OTHER INFORMATION: HDM100B* synthetic peptide
<220> FEATURE:
<221> NAME/KEY: MOD_RES
<222> LOCATION: (8)..(8)
<223> OTHER INFORMATION: Xaa = Abu

<400> SEQUENCE: 30

Arg Phe Gly Ile Ser Asn Tyr Xaa Gln Ile Tyr Pro Pro Asn Val Asn
```

Lys

<210> SEQ ID NO 31
<211> LENGTH: 16
<212> TYPE: PRT
<213> ORGANISM: Dermatophagoides pteronyssinus

<400> SEQUENCE: 31

Asn Tyr Cys Gln Ile Tyr Pro Pro Asn Val Asn Lys Ile Arg Glu Ala
1               5                   10                  15

<210> SEQ ID NO 32
<211> LENGTH: 16
<212> TYPE: PRT
<213> ORGANISM: Artificial sequence
<220> FEATURE:
<223> OTHER INFORMATION: HDM101B* synthetic peptide
<220> FEATURE:
<221> NAME/KEY: MOD_RES
<222> LOCATION: (3)..(3)
<223> OTHER INFORMATION: Xaa = Abu

<400> SEQUENCE: 32

Asn Tyr Xaa Gln Ile Tyr Pro Pro Asn Val Asn Lys Ile Arg Glu Ala
1               5                   10                  15

<210> SEQ ID NO 33
<211> LENGTH: 13
<212> TYPE: PRT
<213> ORGANISM: Dermatophagoides pteronyssinus

<400> SEQUENCE: 33

Asn Ala Gln Arg Phe Gly Ile Ser Asn Tyr Cys Gln Ile
1               5                   10

<210> SEQ ID NO 34
<211> LENGTH: 13
<212> TYPE: PRT
<213> ORGANISM: Artificial sequence
<220> FEATURE:
<223> OTHER INFORMATION: HDM102B* synthetic peptide
<220> FEATURE:
<221> NAME/KEY: MOD_RES
<222> LOCATION: (11)..(11)
<223> OTHER INFORMATION: Xaa = Abu

<400> SEQUENCE: 34

Asn Ala Gln Arg Phe Gly Ile Ser Asn Tyr Xaa Gln Ile
1               5                   10

<210> SEQ ID NO 35
<211> LENGTH: 10
<212> TYPE: PRT
<213> ORGANISM: Dermatophagoides pteronyssinus

<400> SEQUENCE: 35

Glu Leu Val Asp Cys Ala Ser Gln His Gly
1               5                   10

<210> SEQ ID NO 36
<211> LENGTH: 10
<212> TYPE: PRT
<213> ORGANISM: Artificial sequence
<220> FEATURE:
<223> OTHER INFORMATION: HDM03W synthetic peptide

<400> SEQUENCE: 36

```
Glu Leu Val Asp Ser Ala Ser Gln His Gly
1               5                   10
```

<210> SEQ ID NO 37
<211> LENGTH: 13
<212> TYPE: PRT
<213> ORGANISM: Felis catus

<400> SEQUENCE: 37

```
Cys Pro Ala Val Lys Arg Asp Val Asp Leu Phe Leu Thr
1               5                   10
```

<210> SEQ ID NO 38
<211> LENGTH: 17
<212> TYPE: PRT
<213> ORGANISM: Felis catus

<400> SEQUENCE: 38

```
Lys Ala Leu Pro Val Val Leu Glu Asn Ala Arg Ile Leu Lys Asn Cys
1               5                   10                  15

Val
```

<210> SEQ ID NO 39
<211> LENGTH: 17
<212> TYPE: PRT
<213> ORGANISM: Felis catus

<400> SEQUENCE: 39

```
Arg Ile Leu Lys Asn Cys Val Asp Ala Lys Met Thr Glu Glu Asp Lys
1               5                   10                  15

Glu
```

<210> SEQ ID NO 40
<211> LENGTH: 16
<212> TYPE: PRT
<213> ORGANISM: Felis catus

<400> SEQUENCE: 40

```
Thr Ala Met Lys Lys Ile Gln Asp Cys Tyr Val Glu Asn Gly Leu Ile
1               5                   10                  15
```

<210> SEQ ID NO 41
<211> LENGTH: 16
<212> TYPE: PRT
<213> ORGANISM: Felis catus

<400> SEQUENCE: 41

```
Ile Ser Ser Ser Lys Asp Cys Met Gly Glu Ala Val Gln Asn Thr Val
1               5                   10                  15
```

<210> SEQ ID NO 42
<211> LENGTH: 15
<212> TYPE: PRT
<213> ORGANISM: Homo sapiens

<400> SEQUENCE: 42

```
Ala Tyr Phe Gly Leu Ser Val Ala Trp Cys Leu Pro Lys Pro Leu
1               5                   10                  15
```

<210> SEQ ID NO 43
<211> LENGTH: 15
<212> TYPE: PRT
<213> ORGANISM: Artificial sequence
<220> FEATURE:

-continued

<223> OTHER INFORMATION: HDN28A* synthetic peptide

<400> SEQUENCE: 43

Ala Tyr Phe Gly Leu Ser Val Ala Trp Ser Leu Pro Lys Pro Leu
1               5                   10                  15

<210> SEQ ID NO 44
<211> LENGTH: 15
<212> TYPE: PRT
<213> ORGANISM: Homo sapiens

<400> SEQUENCE: 44

Thr Thr Arg Gly Val Ser Ser Cys Gln Gln Cys Leu Ala Val Ser
1               5                   10                  15

<210> SEQ ID NO 45
<211> LENGTH: 15
<212> TYPE: PRT
<213> ORGANISM: Artificial sequence
<220> FEATURE:
<223> OTHER INFORMATION: AIT02A* synthetic peptide

<400> SEQUENCE: 45

Thr Thr Arg Gly Val Ser Ser Ser Gln Gln Ser Leu Ala Val Ser
1               5                   10                  15

<210> SEQ ID NO 46
<211> LENGTH: 15
<212> TYPE: PRT
<213> ORGANISM: Homo sapiens

<400> SEQUENCE: 46

Asp Leu Pro Glu Glu Leu Ser Leu Ser Phe Asn Ala Thr Cys Leu
1               5                   10                  15

<210> SEQ ID NO 47
<211> LENGTH: 15
<212> TYPE: PRT
<213> ORGANISM: Artificial sequence
<220> FEATURE:
<223> OTHER INFORMATION: AIT47A* synthetic peptide

<400> SEQUENCE: 47

Asp Leu Pro Glu Glu Leu Ser Leu Ser Phe Asn Ala Thr Ser Leu
1               5                   10                  15

<210> SEQ ID NO 48
<211> LENGTH: 15
<212> TYPE: PRT
<213> ORGANISM: Homo sapiens

<400> SEQUENCE: 48

Phe Lys Asp Ser Leu Ile Val Gln Val Thr Phe Asp Cys Asp Cys
1               5                   10                  15

<210> SEQ ID NO 49
<211> LENGTH: 15
<212> TYPE: PRT
<213> ORGANISM: Artificial sequence
<220> FEATURE:
<223> OTHER INFORMATION: AIT53A* synthetic peptide

<400> SEQUENCE: 49

Phe Lys Asp Ser Leu Ile Val Gln Val Thr Phe Asp Ser Asp Ser
1               5                   10                  15

```
<210> SEQ ID NO 50
<211> LENGTH: 15
<212> TYPE: PRT
<213> ORGANISM: Homo sapiens

<400> SEQUENCE: 50

Pro Gly Ser Tyr Glu Asp Thr Cys Glu Lys Cys Pro Thr Cys Pro
1               5                   10                  15

<210> SEQ ID NO 51
<211> LENGTH: 15
<212> TYPE: PRT
<213> ORGANISM: Artificial sequence
<220> FEATURE:
<223> OTHER INFORMATION: AIT70A* synthetic peptide

<400> SEQUENCE: 51

Pro Gly Ser Tyr Glu Asp Thr Ser Glu Lys Ser Pro Thr Ser Pro
1               5                   10                  15

<210> SEQ ID NO 52
<211> LENGTH: 15
<212> TYPE: PRT
<213> ORGANISM: Homo sapiens

<400> SEQUENCE: 52

Asp Asp Cys Val Val Arg Phe Gln Tyr Tyr Glu Asp Ser Ser Gly
1               5                   10                  15

<210> SEQ ID NO 53
<211> LENGTH: 15
<212> TYPE: PRT
<213> ORGANISM: Artificial sequence
<220> FEATURE:
<223> OTHER INFORMATION: AIT77A* synthetic peptide

<400> SEQUENCE: 53

Asp Asp Ser Val Val Arg Phe Gln Tyr Tyr Glu Asp Ser Ser Gly
1               5                   10                  15

<210> SEQ ID NO 54
<211> LENGTH: 17
<212> TYPE: PRT
<213> ORGANISM: Artificial sequence
<220> FEATURE:
<223> OTHER INFORMATION: HDM100A* synthetic peptide

<400> SEQUENCE: 54

Arg Phe Gly Ile Ser Asn Tyr Ser Gln Ile Tyr Pro Pro Asn Val Asn
1               5                   10                  15

Lys

<210> SEQ ID NO 55
<211> LENGTH: 16
<212> TYPE: PRT
<213> ORGANISM: Artificial sequence
<220> FEATURE:
<223> OTHER INFORMATION: HDM101A* synthetic peptide

<400> SEQUENCE: 55

Asn Tyr Ser Gln Ile Tyr Pro Pro Asn Val Asn Lys Ile Arg Glu Ala
1               5                   10                  15

<210> SEQ ID NO 56
<211> LENGTH: 13
<212> TYPE: PRT
<213> ORGANISM: Artificial sequence
```

-continued

```
<220> FEATURE:
<223> OTHER INFORMATION: HDM102A* synthetic peptide

<400> SEQUENCE: 56

Asn Ala Gln Arg Phe Gly Ile Ser Asn Tyr Ser Gln Ile
1               5                   10

<210> SEQ ID NO 57
<211> LENGTH: 19
<212> TYPE: PRT
<213> ORGANISM: Dermatophagoides pteronyssinus

<400> SEQUENCE: 57

Asp Leu Arg Gln Met Arg Thr Val Thr Pro Ile Arg Met Gln Gly Gly
1               5                   10                  15

Cys Gly Ser

<210> SEQ ID NO 58
<211> LENGTH: 19
<212> TYPE: PRT
<213> ORGANISM: Artificial sequence
<220> FEATURE:
<223> OTHER INFORMATION: HDM203B* synthetic peptide

<400> SEQUENCE: 58

Asp Leu Arg Gln Met Arg Thr Val Thr Pro Ile Arg Met Gln Gly Gly
1               5                   10                  15

Ser Gly Ser

<210> SEQ ID NO 59
<211> LENGTH: 15
<212> TYPE: PRT
<213> ORGANISM: Ambrosia artemisiifolia

<400> SEQUENCE: 59

Gly Ser Ser Gln Ile Trp Ile Asp His Cys Ser Leu Ser Lys Ala
1               5                   10                  15

<210> SEQ ID NO 60
<211> LENGTH: 15
<212> TYPE: PRT
<213> ORGANISM: Artificial sequence
<220> FEATURE:
<223> OTHER INFORMATION: RGW02* synthetic peptide

<400> SEQUENCE: 60

Gly Ser Ser Gln Ile Trp Ile Asp His Ser Ser Leu Ser Lys Ser
1               5                   10                  15

<210> SEQ ID NO 61
<211> LENGTH: 10
<212> TYPE: PRT
<213> ORGANISM: Artificial sequence
<220> FEATURE:
<223> OTHER INFORMATION: HDM03Wb synthetic peptide
<220> FEATURE:
<221> NAME/KEY: MOD_RES
<222> LOCATION: (5)..(5)
<223> OTHER INFORMATION: Xaa = Abu

<400> SEQUENCE: 61

Glu Leu Val Asp Xaa Ala Ser Gln His Gly
1               5                   10

<210> SEQ ID NO 62
<211> LENGTH: 13
```

```
<212> TYPE: PRT
<213> ORGANISM: Artificial sequence
<220> FEATURE:
<223> OTHER INFORMATION: MLA01a synthetic peptide

<400> SEQUENCE: 62

Ser Pro Ala Val Lys Arg Asp Val Asp Leu Phe Leu Thr
1               5                   10

<210> SEQ ID NO 63
<211> LENGTH: 13
<212> TYPE: PRT
<213> ORGANISM: Artificial sequence
<220> FEATURE:
<223> OTHER INFORMATION: MLA01b synthetic peptide
<220> FEATURE:
<221> NAME/KEY: MOD_RES
<222> LOCATION: (1)..(1)
<223> OTHER INFORMATION: Xaa = Abu

<400> SEQUENCE: 63

Xaa Pro Ala Val Lys Arg Asp Val Asp Leu Phe Leu Thr
1               5                   10

<210> SEQ ID NO 64
<211> LENGTH: 17
<212> TYPE: PRT
<213> ORGANISM: Artificial sequence
<220> FEATURE:
<223> OTHER INFORMATION: MLA04a synthetic peptide

<400> SEQUENCE: 64

Lys Ala Leu Pro Val Val Leu Glu Asn Ala Arg Ile Leu Lys Asn Ser
1               5                   10                  15

Val

<210> SEQ ID NO 65
<211> LENGTH: 17
<212> TYPE: PRT
<213> ORGANISM: Artificial sequence
<220> FEATURE:
<223> OTHER INFORMATION: MLA04b synthetic peptide
<220> FEATURE:
<221> NAME/KEY: MOD_RES
<222> LOCATION: (16)..(16)
<223> OTHER INFORMATION: Xaa = Abu

<400> SEQUENCE: 65

Lys Ala Leu Pro Val Val Leu Glu Asn Ala Arg Ile Leu Lys Asn Xaa
1               5                   10                  15

Val

<210> SEQ ID NO 66
<211> LENGTH: 17
<212> TYPE: PRT
<213> ORGANISM: Artificial sequence
<220> FEATURE:
<223> OTHER INFORMATION: MLA05a synthetic peptide

<400> SEQUENCE: 66

Arg Ile Leu Lys Asn Ser Val Asp Ala Lys Met Thr Glu Glu Asp Lys
1               5                   10                  15

Glu

<210> SEQ ID NO 67
<211> LENGTH: 17
<212> TYPE: PRT
```

```
<213> ORGANISM: Artificial sequence
<220> FEATURE:
<223> OTHER INFORMATION: MLA05b synthetic peptide
<220> FEATURE:
<221> NAME/KEY: MOD_RES
<222> LOCATION: (6)..(6)
<223> OTHER INFORMATION: Xaa = Abu

<400> SEQUENCE: 67

Arg Ile Leu Lys Asn Xaa Val Asp Ala Lys Met Thr Glu Glu Asp Lys
1               5                   10                  15

Glu

<210> SEQ ID NO 68
<211> LENGTH: 16
<212> TYPE: PRT
<213> ORGANISM: Artificial sequence
<220> FEATURE:
<223> OTHER INFORMATION: MLA12a synthetic peptide

<400> SEQUENCE: 68

Thr Ala Met Lys Lys Ile Gln Asp Ser Tyr Val Glu Asn Gly Leu Ile
1               5                   10                  15

<210> SEQ ID NO 69
<211> LENGTH: 16
<212> TYPE: PRT
<213> ORGANISM: Artificial sequence
<220> FEATURE:
<223> OTHER INFORMATION: MLA12b synthetic peptide
<220> FEATURE:
<221> NAME/KEY: MOD_RES
<222> LOCATION: (9)..(9)
<223> OTHER INFORMATION: Xaa = Abu

<400> SEQUENCE: 69

Thr Ala Met Lys Lys Ile Gln Asp Xaa Tyr Val Glu Asn Gly Leu Ile
1               5                   10                  15

<210> SEQ ID NO 70
<211> LENGTH: 16
<212> TYPE: PRT
<213> ORGANISM: Artificial sequence
<220> FEATURE:
<223> OTHER INFORMATION: MLA15a synthetic peptide

<400> SEQUENCE: 70

Ile Ser Ser Ser Lys Asp Ser Met Gly Glu Ala Val Gln Asn Thr Val
1               5                   10                  15

<210> SEQ ID NO 71
<211> LENGTH: 16
<212> TYPE: PRT
<213> ORGANISM: Artificial sequence
<220> FEATURE:
<223> OTHER INFORMATION: MLA15b synthetic peptide
<220> FEATURE:
<221> NAME/KEY: MOD_RES
<222> LOCATION: (7)..(7)
<223> OTHER INFORMATION: Xaa = Abu

<400> SEQUENCE: 71

Ile Ser Ser Ser Lys Asp Xaa Met Gly Glu Ala Val Gln Asn Thr Val
1               5                   10                  15

<210> SEQ ID NO 72
<211> LENGTH: 15
<212> TYPE: PRT
<213> ORGANISM: Artificial sequence
```

```
<220> FEATURE:
<223> OTHER INFORMATION: RGW02c synthetic peptide
<220> FEATURE:
<221> NAME/KEY: MOD_RES
<222> LOCATION: (10)..(10)
<223> OTHER INFORMATION: Xaa = Abu

<400> SEQUENCE: 72

Gly Ser Ser Gln Ile Trp Ile Asp His Xaa Ser Leu Ser Lys Ser
1               5                   10                  15

<210> SEQ ID NO 73
<211> LENGTH: 10
<212> TYPE: PRT
<213> ORGANISM: Homo sapiens

<400> SEQUENCE: 73

Ala Trp Cys Ser Asp Glu Ala Leu Pro Leu
1               5                   10

<210> SEQ ID NO 74
<211> LENGTH: 10
<212> TYPE: PRT
<213> ORGANISM: Artificial sequence
<220> FEATURE:
<223> OTHER INFORMATION: NAIT01A* synthetic peptide

<400> SEQUENCE: 74

Ala Trp Ser Ser Asp Glu Ala Leu Pro Leu
1               5                   10

<210> SEQ ID NO 75
<211> LENGTH: 320
<212> TYPE: PRT
<213> ORGANISM: Dermatophagoides pteronyssinus

<400> SEQUENCE: 75

Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
    130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190
```

```
Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
        210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
                260                 265                 270

Val Gly Tyr Ser Asn Ala Gln Gly Val Asp Tyr Trp Ile Val Arg Asn
                275                 280                 285

Ser Trp Asp Thr Asn Trp Gly Asp Asn Gly Tyr Gly Tyr Phe Ala Ala
        290                 295                 300

Asn Ile Asp Leu Met Met Ile Glu Glu Tyr Pro Tyr Val Val Ile Leu
305                 310                 315                 320

<210> SEQ ID NO 76
<211> LENGTH: 146
<212> TYPE: PRT
<213> ORGANISM: Dermatophagoides pteronyssinus

<400> SEQUENCE: 76

Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
                20                  25                  30

Val Leu Val Pro Gly Cys His Gly Ser Glu Pro Cys Ile Ile His Arg
        35                  40                  45

Gly Lys Pro Phe Gln Leu Glu Ala Val Phe Glu Ala Asn Gln Asn Thr
    50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Val Met
        115                 120                 125

Gly Asp Asp Gly Val Leu Ala Cys Ala Ile Ala Thr His Ala Lys Ile
    130                 135                 140

Arg Asp
145

<210> SEQ ID NO 77
<211> LENGTH: 261
<212> TYPE: PRT
<213> ORGANISM: Dermatophagoides pteronyssinus

<400> SEQUENCE: 77

Met Ile Ile Tyr Asn Ile Leu Ile Val Leu Leu Ala Ile Asn Thr
1               5                   10                  15

Leu Ala Asn Pro Ile Leu Pro Ala Ser Pro Asn Ala Thr Ile Val Gly
                20                  25                  30

Gly Glu Lys Ala Leu Ala Gly Glu Cys Pro Tyr Gln Ile Ser Leu Gln
        35                  40                  45

Ser Ser Ser His Phe Cys Gly Gly Thr Ile Leu Asp Glu Tyr Trp Ile
```

-continued

```
                50                  55                  60
Leu Thr Ala Ala His Cys Val Ala Gly Gln Thr Ala Ser Lys Leu Ser
 65                  70                  75                  80

Ile Arg Tyr Asn Ser Leu Lys His Ser Leu Gly Gly Glu Lys Ile Ser
                 85                  90                  95

Val Ala Lys Ile Phe Ala His Glu Lys Tyr Asp Ser Tyr Gln Ile Asp
            100                 105                 110

Asn Asp Ile Ala Leu Ile Lys Leu Lys Ser Pro Met Lys Leu Asn Gln
        115                 120                 125

Lys Asn Ala Lys Ala Val Gly Leu Pro Ala Lys Gly Ser Asp Val Lys
    130                 135                 140

Val Gly Asp Gln Val Arg Val Ser Gly Trp Gly Tyr Leu Glu Glu Gly
145                 150                 155                 160

Ser Tyr Ser Leu Pro Ser Glu Leu Arg Arg Val Asp Ile Ala Val Val
                165                 170                 175

Ser Arg Lys Glu Cys Asn Glu Leu Tyr Ser Lys Ala Asn Ala Glu Val
            180                 185                 190

Thr Asp Asn Met Ile Cys Gly Gly Asp Val Ala Asn Gly Gly Lys Asp
        195                 200                 205

Ser Cys Gln Gly Asp Ser Gly Gly Pro Val Val Asp Val Lys Asn Asn
    210                 215                 220

Gln Val Val Gly Ile Val Ser Trp Gly Tyr Gly Cys Ala Arg Lys Gly
225                 230                 235                 240

Tyr Pro Gly Val Tyr Thr Arg Val Gly Asn Phe Ile Asp Trp Ile Glu
                245                 250                 255

Ser Lys Arg Ser Gln
            260

<210> SEQ ID NO 78
<211> LENGTH: 19
<212> TYPE: PRT
<213> ORGANISM: Dermatophagoides pteronyssinus
<220> FEATURE:
<221> NAME/KEY: UNSURE
<222> LOCATION: (3)..(3)
<223> OTHER INFORMATION: Xaa = unknown
<220> FEATURE:
<221> NAME/KEY: UNSURE
<222> LOCATION: (10)..(10)
<223> OTHER INFORMATION: Xaa = unknown
<220> FEATURE:
<221> NAME/KEY: UNSURE
<222> LOCATION: (16)..(16)
<223> OTHER INFORMATION: Xaa = unknown

<400> SEQUENCE: 78

Lys Tyr Xaa Asn Pro His Phe Ile Gly Xaa Arg Ser Val Ile Thr Xaa
 1               5                  10                  15

Leu Met Glu

<210> SEQ ID NO 79
<211> LENGTH: 132
<212> TYPE: PRT
<213> ORGANISM: Dermatophagoides pteronyssinus

<400> SEQUENCE: 79

Met Lys Phe Ile Ile Ala Phe Phe Val Ala Thr Leu Ala Val Met Thr
 1               5                  10                  15

Val Ser Gly Glu Asp Lys Lys His Asp Tyr Gln Asn Glu Phe Asp Phe
            20                  25                  30
```

```
Leu Leu Met Glu Arg Ile His Glu Gln Ile Lys Lys Gly Glu Leu Ala
        35                  40                  45

Leu Phe Tyr Leu Gln Glu Gln Ile Asn His Phe Glu Glu Lys Pro Thr
    50                  55                  60

Lys Glu Met Lys Asp Lys Ile Val Ala Glu Met Asp Thr Ile Ile Ala
65                  70                  75                  80

Met Ile Asp Gly Val Arg Gly Val Leu Asp Arg Leu Met Gln Arg Lys
                85                  90                  95

Asp Leu Asp Ile Phe Glu Gln Tyr Asn Leu Glu Met Ala Lys Lys Ser
                100                 105                 110

Gly Asp Ile Leu Glu Arg Asp Leu Lys Lys Glu Ala Arg Val Lys
                115                 120                 125

Lys Ile Glu Val
    130

<210> SEQ ID NO 80
<211> LENGTH: 20
<212> TYPE: PRT
<213> ORGANISM: Dermatophagoides pteronyssinus
<220> FEATURE:
<221> NAME/KEY: UNSURE
<222> LOCATION: (4)..(4)
<223> OTHER INFORMATION: Xaa = unknown

<400> SEQUENCE: 80

Ala Ile Gly Xaa Gln Pro Ala Glu Ala Glu Ala Pro Phe Gln Ile
1               5                   10                  15

Ser Leu Met Lys
            20

<210> SEQ ID NO 81
<211> LENGTH: 215
<212> TYPE: PRT
<213> ORGANISM: Dermatophagoides pteronyssinus

<400> SEQUENCE: 81

Met Met Lys Leu Leu Leu Ile Ala Ala Ala Ala Phe Val Ala Val Ser
1               5                   10                  15

Ala Asp Pro Ile His Tyr Asp Lys Ile Thr Glu Glu Ile Asn Lys Ala
                20                  25                  30

Val Asp Glu Ala Val Ala Ala Ile Glu Lys Ser Glu Thr Phe Asp Pro
            35                  40                  45

Met Lys Val Pro Asp His Ser Asp Lys Phe Glu Arg His Ile Gly Ile
    50                  55                  60

Ile Asp Leu Lys Gly Glu Leu Asp Met Arg Asn Ile Gln Val Arg Gly
65                  70                  75                  80

Leu Lys Gln Met Lys Arg Val Gly Asp Ala Asn Val Lys Ser Glu Asp
                85                  90                  95

Gly Val Val Lys Ala His Leu Leu Val Gly Val His Asp Asp Val Val
                100                 105                 110

Ser Met Glu Tyr Asp Leu Ala Tyr Lys Leu Gly Asp Leu His Pro Asn
            115                 120                 125

Thr His Val Ile Ser Asp Ile Gln Asp Phe Val Val Glu Leu Ser Leu
        130                 135                 140

Glu Val Ser Glu Glu Gly Asn Met Thr Leu Thr Ser Phe Glu Val Arg
145                 150                 155                 160

Gln Phe Ala Asn Val Val Asn His Ile Gly Gly Leu Ser Ile Leu Asp
                165                 170                 175
```

-continued

Pro Ile Phe Ala Val Leu Ser Asp Val Leu Thr Ala Ile Phe Gln Asp
        180                 185                 190

Thr Val Arg Ala Glu Met Thr Lys Val Leu Ala Pro Ala Phe Lys Lys
        195                 200                 205

Glu Leu Glu Arg Asn Asn Gln
        210                 215

<210> SEQ ID NO 82
<211> LENGTH: 18
<212> TYPE: PRT
<213> ORGANISM: Dermatophagoides pteronyssinus

<400> SEQUENCE: 82

Ile Val Gly Gly Ser Asn Ala Ser Pro Gly Asp Ala Val Tyr Gln Ile
1               5                   10                  15

Ala Leu

<210> SEQ ID NO 83
<211> LENGTH: 319
<212> TYPE: PRT
<213> ORGANISM: Dermatophagoides farinae

<400> SEQUENCE: 83

Met Lys Phe Val Leu Ala Ile Ala Ser Leu Leu Val Leu Thr Val Tyr
1               5                   10                  15

Ala Arg Pro Ala Ser Ile Lys Thr Phe Glu Phe Lys Lys Ala Phe Asn
            20                  25                  30

Lys Asn Tyr Ala Thr Val Glu Glu Glu Val Ala Arg Lys Asn Phe
        35                  40                  45

Leu Glu Ser Leu Lys Tyr Val Glu Ala Asn Lys Gly Ala Ile Asn His
    50                  55                  60

Leu Ser Asp Leu Ser Leu Asp Glu Phe Lys Asn Arg Tyr Leu Met Ser
65                  70                  75                  80

Ala Glu Ala Phe Glu Gln Leu Lys Thr Gln Phe Asp Leu Asn Ala Glu
                85                  90                  95

Thr Ser Ala Cys Arg Ile Asn Ser Val Asn Val Pro Ser Glu Leu Asp
            100                 105                 110

Leu Arg Ser Leu Arg Thr Val Thr Pro Ile Arg Met Gln Gly Gly Cys
        115                 120                 125

Gly Ser Cys Trp Ala Phe Ser Gly Val Ala Ala Thr Glu Ser Ala Tyr
    130                 135                 140

Leu Ala Tyr Arg Asn Thr Ser Leu Asp Leu Ser Glu Gln Glu Leu Val
145                 150                 155                 160

Asp Cys Ala Ser Gln His Gly Cys His Gly Asp Thr Ile Pro Arg Gly
                165                 170                 175

Ile Glu Tyr Ile Gln Gln Asn Gly Val Val Glu Glu Arg Ser Tyr Pro
            180                 185                 190

Tyr Val Ala Arg Glu Gln Arg Cys Arg Arg Pro Asn Ser Gln His Tyr
        195                 200                 205

Gly Ile Ser Asn Tyr Cys Gln Ile Tyr Pro Pro Asp Val Lys Gln Ile
    210                 215                 220

Arg Glu Ala Leu Thr Gln Thr His Thr Ala Ile Ala Val Ile Ile Gly
225                 230                 235                 240

Ile Lys Asp Leu Arg Ala Phe Gln His Tyr Asp Gly Arg Thr Ile Ile
                245                 250                 255

Gln His Asp Asn Gly Tyr Gln Pro Asn Tyr His Ala Val Asn Ile Val
            260                 265                 270

```
Gly Tyr Gly Ser Thr Gln Gly Asp Asp Tyr Trp Ile Val Arg Asn Ser
            275                 280                 285

Trp Asp Thr Thr Trp Gly Asp Ser Gly Tyr Gly Tyr Phe Gln Ala Gly
            290                 295                 300

Asn Asn Leu Met Met Ile Glu Gln Tyr Pro Tyr Val Val Ile Met
305                 310                 315

<210> SEQ ID NO 84
<211> LENGTH: 146
<212> TYPE: PRT
<213> ORGANISM: Dermatophagoides farinae

<400> SEQUENCE: 84

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Leu Ile
        115                 120                 125

Gly Asp Asn Gly Val Leu Ala Cys Ala Ile Ala Thr His Gly Lys Ile
    130                 135                 140

Arg Asp
145

<210> SEQ ID NO 85
<211> LENGTH: 259
<212> TYPE: PRT
<213> ORGANISM: Dermatophagoides farinae

<400> SEQUENCE: 85

Met Met Ile Leu Thr Ile Val Val Leu Ala Ala Asn Ile Leu Ala
1               5                   10                  15

Thr Pro Ile Leu Pro Ser Ser Pro Asn Ala Thr Ile Val Gly Gly Val
            20                  25                  30

Lys Ala Gln Ala Gly Asp Cys Pro Tyr Gln Ile Ser Leu Gln Ser Ser
        35                  40                  45

Ser His Phe Cys Gly Gly Ser Ile Leu Asp Glu Tyr Trp Ile Leu Thr
    50                  55                  60

Ala Ala His Cys Val Asn Gly Gln Ser Ala Lys Lys Leu Ser Ile Arg
65                  70                  75                  80

Tyr Asn Thr Leu Lys His Ala Ser Gly Gly Glu Lys Ile Gln Val Ala
                85                  90                  95

Glu Ile Tyr Gln His Glu Asn Tyr Asp Ser Met Thr Ile Asp Asn Asp
            100                 105                 110

Val Ala Leu Ile Lys Leu Lys Thr Pro Met Thr Leu Asp Gln Thr Asn
        115                 120                 125
```

```
Ala Lys Pro Val Pro Leu Pro Ala Gln Gly Ser Asp Val Lys Val Gly
            130                 135                 140

Asp Lys Ile Arg Val Ser Gly Trp Gly Tyr Leu Gln Glu Gly Ser Tyr
145                 150                 155                 160

Ser Leu Pro Ser Glu Leu Gln Arg Val Asp Ile Asp Val Val Ser Arg
                165                 170                 175

Glu Gln Cys Asp Gln Leu Tyr Ser Lys Ala Gly Ala Asp Val Ser Glu
            180                 185                 190

Asn Met Ile Cys Gly Gly Asp Val Ala Asn Gly Gly Val Asp Ser Cys
        195                 200                 205

Gln Gly Asp Ser Gly Gly Pro Val Val Asp Val Ala Thr Lys Gln Ile
    210                 215                 220

Val Gly Ile Val Ser Trp Gly Tyr Gly Cys Ala Arg Lys Gly Tyr Pro
225                 230                 235                 240

Gly Val Tyr Thr Arg Val Gly Asn Phe Val Asp Trp Ile Glu Ser Lys
                245                 250                 255

Arg Ser Gln

<210> SEQ ID NO 86
<211> LENGTH: 20
<212> TYPE: PRT
<213> ORGANISM: Dermatophagoides farinae

<400> SEQUENCE: 86

Ala Val Gly Gly Gln Asp Ala Asp Leu Ala Glu Ala Pro Phe Gln Ile
1               5                   10                  15

Ser Leu Leu Lys
            20

<210> SEQ ID NO 87
<211> LENGTH: 213
<212> TYPE: PRT
<213> ORGANISM: Dermatophagoides farinae

<400> SEQUENCE: 87

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
            20                  25                  30

Ile Asp Asp Ala Ile Ala Ala Ile Glu Gln Ser Glu Thr Ile Asp Pro
        35                  40                  45

Met Lys Val Pro Asp His Ala Asp Lys Phe Glu Arg His Val Gly Ile
50                  55                  60

Val Asp Phe Lys Gly Glu Leu Ala Met Arg Asn Ile Glu Ala Arg Gly
65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
            100                 105                 110

Ser Met Glu Tyr Asp Leu Ala Tyr Lys Leu Gly Asp Leu His Pro Thr
        115                 120                 125

Thr His Val Ile Ser Asp Ile Gln Asp Phe Val Ala Leu Ser Leu
    130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175
```

```
Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
        195                 200                 205

Glu Leu Glu Lys Asn
    210

<210> SEQ ID NO 88
<211> LENGTH: 138
<212> TYPE: PRT
<213> ORGANISM: Hevea brasiliensis

<400> SEQUENCE: 88

Met Ala Glu Asp Glu Asn Gln Gln Gly Gln Gly Glu Gly Leu Lys
1               5                   10                  15

Tyr Leu Gly Phe Val Gln Asp Ala Ala Thr Tyr Ala Val Thr Thr Phe
                20                  25                  30

Ser Asn Val Tyr Leu Phe Ala Lys Asp Lys Ser Gly Pro Leu Gln Pro
            35                  40                  45

Gly Val Asp Ile Ile Glu Gly Pro Val Lys Asn Val Ala Val Pro Leu
        50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
        115                 120                 125

Ile Leu Ala Lys Val Phe Tyr Gly Glu Asn
        130                 135

<210> SEQ ID NO 89
<211> LENGTH: 204
<212> TYPE: PRT
<213> ORGANISM: Hevea brasiliensis

<400> SEQUENCE: 89

Met Ala Glu Glu Val Glu Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
                20                  25                  30

Tyr Ala Lys Asp Ile Ser Gly Pro Leu Lys Pro Gly Val Asp Thr Ile
            35                  40                  45

Glu Asn Val Val Lys Thr Val Val Thr Pro Val Tyr Tyr Ile Pro Leu
        50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
        115                 120                 125

Asn Leu Glu Pro Lys Ala Glu Gln Tyr Ala Val Ile Thr Trp Arg Ala
        130                 135                 140
```

```
Leu Asn Lys Leu Pro Leu Val Pro Gln Val Ala Asn Val Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
        195                 200

<210> SEQ ID NO 90
<211> LENGTH: 263
<212> TYPE: PRT
<213> ORGANISM: Lolium perenne

<400> SEQUENCE: 90

Met Ala Ser Ser Ser Val Leu Leu Val Ala Leu Phe Ala Val
1               5                   10                  15

Phe Leu Gly Ser Ala His Gly Ile Ala Lys Val Pro Pro Gly Pro Asn
                20                  25                  30

Ile Thr Ala Glu Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
50                  55                  60

Gly Tyr Lys Asn Val Asp Lys Ala Pro Phe Asn Gly Met Thr Gly Cys
65                  70                  75                  80

Gly Asn Thr Pro Ile Phe Lys Asp Gly Arg Gly Cys Gly Ser Cys Phe
                85                  90                  95

Glu Ile Lys Cys Thr Lys Pro Glu Ser Cys Ser Gly Glu Ala Val Thr
            100                 105                 110

Val Thr Ile Thr Asp Asp Asn Glu Glu Pro Ile Ala Pro Tyr His Phe
        115                 120                 125

Asp Leu Ser Gly His Ala Phe Gly Ser Met Ala Lys Lys Gly Glu Glu
    130                 135                 140

Gln Asn Val Arg Ser Ala Gly Glu Leu Glu Leu Gln Phe Arg Arg Val
145                 150                 155                 160

Lys Cys Lys Tyr Pro Asp Asp Thr Lys Pro Thr Phe His Val Glu Lys
                165                 170                 175

Ala Ser Asn Pro Asn Tyr Leu Ala Ile Leu Val Lys Tyr Val Asp Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Val Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Ser Glu Phe Glu Asp Val Ile Pro Glu Gly Trp Lys Ala
                245                 250                 255

Asp Thr Ser Tyr Ser Ala Lys
            260

<210> SEQ ID NO 91
<211> LENGTH: 97
<212> TYPE: PRT
<213> ORGANISM: Lolium perenne

<400> SEQUENCE: 91

Ala Ala Pro Val Glu Phe Thr Val Glu Lys Gly Ser Asp Glu Lys Asn
```

```
                 1               5                  10                 15
Leu Ala Leu Ser Ile Lys Tyr Asn Lys Glu Gly Asp Ser Met Ala Glu
                20                  25                 30

Val Glu Leu Lys Glu His Gly Ser Asn Glu Trp Leu Ala Leu Lys Lys
                35                  40                 45

Asn Gly Asp Gly Val Trp Glu Ile Lys Ser Asp Lys Pro Leu Lys Gly
                50                  55                 60

Pro Phe Asn Phe Arg Phe Val Ser Glu Lys Gly Met Arg Asn Val Phe
 65                 70                  75                    80

Asp Asp Val Val Pro Ala Asp Phe Lys Val Gly Thr Thr Tyr Lys Pro
                85                  90                 95

Glu

<210> SEQ ID NO 92
<211> LENGTH: 97
<212> TYPE: PRT
<213> ORGANISM: Lolium perenne

<400> SEQUENCE: 92

Thr Lys Val Asp Leu Thr Val Glu Lys Gly Ser Asp Ala Lys Thr Leu
 1               5                  10                 15

Val Leu Asn Ile Lys Tyr Thr Arg Pro Gly Asp Thr Leu Ala Glu Val
                20                  25                 30

Glu Leu Arg Gln His Gly Ser Glu Glu Trp Glu Pro Met Thr Lys Lys
                35                  40                 45

Gly Asn Leu Trp Glu Val Lys Ser Ala Lys Pro Leu Thr Gly Pro Met
                50                  55                 60

Asn Phe Arg Phe Leu Ser Lys Gly Gly Met Lys Asn Val Phe Asp Glu
 65                 70                  75                    80

Val Ile Pro Thr Ala Phe Thr Val Gly Lys Thr Tyr Thr Pro Glu Tyr
                85                  90                 95

Asn

<210> SEQ ID NO 93
<211> LENGTH: 308
<212> TYPE: PRT
<213> ORGANISM: Lolium perenne

<400> SEQUENCE: 93

Met Ala Val Gln Lys Tyr Thr Val Ala Leu Phe Leu Arg Arg Gly Pro
 1               5                  10                 15

Arg Gly Gly Pro Gly Arg Ser Tyr Ala Ala Asp Ala Gly Tyr Thr Pro
                20                  25                 30

Ala Ala Ala Ala Thr Pro Ala Thr Pro Ala Ala Thr Pro Ala Gly Gly
                35                  40                 45

Trp Arg Glu Gly Asp Asp Arg Arg Ala Glu Ala Ala Gly Gly Arg Gln
                50                  55                 60

Arg Leu Ala Ser Arg Gln Pro Trp Pro Leu Pro Thr Pro Leu Arg
 65                 70                  75                    80

Arg Thr Ser Ser Arg Ser Ser Arg Pro Pro Ser Pro Ser Pro Pro Arg
                85                  90                 95

Ala Ser Ser Pro Thr Ser Ala Ala Lys Ala Pro Gly Leu Ile Pro Lys
                100                 105                110

Leu Asp Thr Ala Tyr Asp Val Ala Tyr Lys Ala Ala Glu Ala His Pro
                115                 120                125

Arg Gly Gln Val Arg Arg Leu Arg His Cys Pro His Arg Ser Leu Arg
```

```
                130                 135                 140
Val Ile Ala Gly Ala Leu Glu Val His Ala Val Lys Pro Ala Thr Glu
145                 150                 155                 160

Glu Val Leu Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
                180                 185                 190

Pro Thr Asn Asp Lys Phe Thr Val Phe Glu Ser Ala Phe Asn Lys Ala
                195                 200                 205

Leu Asn Glu Cys Thr Gly Gly Ala Met Arg Pro Thr Ser Ser Ser Pro
210                 215                 220

Pro Ser Arg Pro Arg Ser Ser Arg Pro Thr Pro Pro Ser Pro Ala
225                 230                 235                 240

Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
                260                 265                 270

Ala Ala Thr Ala Ala Ala Thr Val Ala Thr Ala Ala Thr Ala Ala
                275                 280                 285

Ala Val Leu Pro Pro Pro Leu Leu Val Val Gln Ser Leu Ile Ser Leu
                290                 295                 300

Leu Ile Tyr Tyr
305

<210> SEQ ID NO 94
<211> LENGTH: 339
<212> TYPE: PRT
<213> ORGANISM: Lolium perenne

<400> SEQUENCE: 94

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Thr Pro Ala Ala Pro Ala Thr Ala Ala Thr Pro Ala
                35                  40                  45

Thr Pro Ala Thr Pro Ala Thr Pro Ala Ala Val Pro Ser Gly Lys Ala
50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
                100                 105                 110

Gly Leu Ala Ser Gly Tyr Ala Asp Gln Ser Lys Asn Gln Leu Thr Ser
                115                 120                 125

Lys Leu Asp Ala Ala Leu Lys Leu Ala Tyr Glu Ala Ala Gln Gly Ala
                130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
                180                 185                 190

Ile Asp Lys Val Asp Ala Ala Tyr Arg Thr Ala Ala Thr Ala Ala Asn
```

```
                195                 200                 205
Ala Ala Pro Ala Asn Asp Lys Phe Thr Val Phe Glu Asn Thr Phe Asn
210                 215                 220

Asn Ala Ile Lys Val Ser Leu Gly Ala Ala Tyr Asp Ser Tyr Lys Phe
225                 230                 235                 240

Ile Pro Thr Leu Val Ala Ala Val Lys Gln Ala Tyr Ala Ala Lys Gln
                245                 250                 255

Ala Thr Ala Pro Glu Val Lys Tyr Thr Val Ser Glu Thr Ala Leu Lys
                260                 265                 270

Lys Ala Val Thr Ala Met Ser Glu Ala Lys Glu Ala Thr Pro Ala
                275                 280                 285

Ala Ala Thr Ala Thr Pro Thr Pro Ala Ala Thr Ala Thr Ala
290                 295                 300

Thr Pro Ala Ala Ala Tyr Ala Thr Ala Thr Pro Ala Ala Ala Thr Ala
305                 310                 315                 320

Thr Ala Thr Pro Ala Ala Ala Thr Ala Thr Pro Ala Ala Ala Gly Gly
                325                 330                 335

Tyr Lys Val

<210> SEQ ID NO 95
<211> LENGTH: 339
<212> TYPE: PRT
<213> ORGANISM: Lolium perenne

<400> SEQUENCE: 95

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Thr Pro Ala Ala Pro Ala Thr Ala Ala Thr Pro Ala
                35                  40                  45

Thr Pro Ala Thr Pro Ala Thr Pro Ala Ala Val Pro Ser Gly Lys Ala
50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
                100                 105                 110

Gly Leu Ala Ser Gly Tyr Ala Asp Gln Ser Lys Asn Gln Leu Thr Ser
                115                 120                 125

Lys Leu Asp Ala Ala Leu Lys Leu Ala Tyr Glu Ala Ala Gln Gly Ala
130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
                180                 185                 190

Ile Asp Lys Val Asp Ala Ala Tyr Arg Thr Ala Thr Ala Ala Asn
                195                 200                 205

Ala Ala Pro Ala Asn Asp Lys Phe Thr Val Phe Glu Asn Thr Phe Asn
210                 215                 220

Asn Ala Ile Lys Val Ser Leu Gly Ala Ala Tyr Asp Ser Tyr Lys Phe
225                 230                 235                 240
```

```
Ile Pro Thr Leu Val Ala Ala Val Lys Gln Ala Tyr Ala Ala Lys Gln
                245                 250                 255

Ala Thr Ala Pro Glu Val Lys Tyr Thr Val Ser Glu Thr Ala Leu Lys
            260                 265                 270

Lys Ala Val Thr Ala Met Ser Glu Ala Lys Glu Ala Thr Pro Ala
        275                 280                 285

Ala Ala Ala Thr Ala Thr Pro Thr Pro Ala Ala Thr Ala Thr Ala
    290                 295                 300

Thr Pro Ala Ala Ala Tyr Ala Thr Ala Thr Pro Ala Ala Thr Ala
305                 310                 315                 320

Thr Ala Thr Pro Ala Ala Ala Thr Ala Thr Pro Ala Ala Gly Gly
            325                 330                 335

Tyr Lys Val

<210> SEQ ID NO 96
<211> LENGTH: 134
<212> TYPE: PRT
<213> ORGANISM: Lolium perenne
<220> FEATURE:
<221> NAME/KEY: UNSURE
<222> LOCATION: (103)..(103)
<223> OTHER INFORMATION: Xaa = unknown

<400> SEQUENCE: 96

Asp Lys Gly Pro Gly Phe Val Val Thr Gly Arg Val Tyr Cys Asp Pro
1               5                   10                  15

Cys Arg Ala Gly Phe Glu Thr Asn Val Ser His Asn Val Glu Gly Ala
            20                  25                  30

Thr Val Ala Val Asp Cys Arg Pro Phe Asp Gly Gly Glu Ser Lys Leu
        35                  40                  45

Lys Ala Glu Ala Thr Thr Asp Lys Asp Gly Trp Tyr Lys Ile Glu Ile
    50                  55                  60

Asp Gln Asp His Gln Glu Glu Ile Cys Glu Val Val Leu Ala Lys Ser
65                  70                  75                  80

Pro Asp Lys Ser Cys Ser Glu Ile Glu Glu Phe Arg Asp Arg Ala Arg
                85                  90                  95

Val Pro Leu Thr Ser Asn Xaa Gly Ile Lys Gln Gln Gly Ile Arg Tyr
            100                 105                 110

Ala Asn Pro Ile Ala Phe Phe Arg Lys Glu Pro Leu Lys Glu Cys Gly
        115                 120                 125

Gly Ile Leu Gln Ala Tyr
    130

<210> SEQ ID NO 97
<211> LENGTH: 145
<212> TYPE: PRT
<213> ORGANISM: Olea europaea

<400> SEQUENCE: 97

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30

Phe Ile Pro Gly Ala Ser Leu Arg Leu Gln Cys Lys Asp Lys Glu Asn
        35                  40                  45

Gly Asp Val Thr Phe Thr Glu Val Gly Tyr Thr Arg Ala Glu Gly Leu
    50                  55                  60
```

```
Tyr Ser Met Leu Val Glu Arg Asp His Lys Asn Glu Phe Cys Glu Ile
 65                  70                  75                  80

Thr Leu Ile Ser Ser Gly Arg Lys Asp Cys Asn Glu Ile Pro Thr Glu
                 85                  90                  95

Gly Trp Ala Lys Pro Ser Leu Lys Phe Lys Leu Asn Thr Val Asn Gly
            100                 105                 110

Thr Thr Arg Thr Val Asn Pro Leu Gly Phe Phe Lys Lys Glu Ala Leu
        115                 120                 125

Pro Lys Cys Ala Gln Val Tyr Asn Lys Leu Gly Met Tyr Pro Pro Asn
    130                 135                 140

Met
145

<210> SEQ ID NO 98
<211> LENGTH: 133
<212> TYPE: PRT
<213> ORGANISM: Parietaria judaica

<400> SEQUENCE: 98

Met Arg Thr Val Ser Met Ala Ala Leu Val Val Ile Ala Ala Ala Leu
  1               5                  10                  15

Ala Trp Thr Ser Ser Ala Glu Pro Ala Pro Ala Pro Ala Pro Gly Glu
                 20                  25                  30

Glu Ala Cys Gly Lys Val Val Gln Asp Ile Met Pro Cys Leu His Phe
             35                  40                  45

Val Lys Gly Glu Glu Lys Glu Pro Ser Lys Cys Cys Ser Gly Thr
 50                  55                  60

Lys Lys Leu Ser Glu Glu Val Lys Thr Thr Glu Gln Lys Arg Glu Ala
 65                  70                  75                  80

Cys Lys Cys Ile Val Arg Ala Thr Lys Gly Ile Ser Gly Ile Lys Asn
                 85                  90                  95

Glu Leu Val Ala Glu Val Pro Lys Lys Cys Asp Ile Lys Thr Thr Leu
            100                 105                 110

Pro Pro Ile Thr Ala Asp Phe Asp Cys Ser Lys Ile Gln Ser Thr Ile
        115                 120                 125

Phe Arg Gly Tyr Tyr
    130

<210> SEQ ID NO 99
<211> LENGTH: 133
<212> TYPE: PRT
<213> ORGANISM: Parietaria judaica

<400> SEQUENCE: 99

Met Val Arg Ala Leu Met Pro Cys Leu Pro Phe Val Gln Gly Lys Glu
  1               5                  10                  15

Lys Glu Pro Ser Lys Gly Cys Cys Ser Gly Ala Lys Arg Leu Asp Gly
                 20                  25                  30

Glu Thr Lys Thr Gly Pro Gln Arg Val His Ala Cys Glu Cys Ile Gln
             35                  40                  45

Thr Ala Met Lys Thr Tyr Ser Asp Ile Asp Gly Lys Leu Val Ser Glu
 50                  55                  60

Val Pro Lys His Cys Gly Ile Asp Ser Lys Leu Pro Pro Ile Asp
 65                  70                  75                  80

Val Asn Met Asp Cys Lys Thr Val Gly Val Pro Arg Gln Pro Gln
                 85                  90                  95

Leu Pro Val Ser Leu Arg His Gly Pro Val Thr Gly Pro Ser Asp Pro
```

```
                    100                 105                 110
Ala His Lys Ala Arg Leu Glu Arg Pro Gln Ile Arg Val Pro Pro Pro
        115                 120                 125

Ala Pro Glu Lys Ala
        130

<210> SEQ ID NO 100
<211> LENGTH: 133
<212> TYPE: PRT
<213> ORGANISM: Parietaria judaica

<400> SEQUENCE: 100

Met Arg Thr Val Ser Met Ala Leu Val Val Ile Ala Ala Ala Ala Leu
1               5                   10                  15

Ala Trp Thr Ser Ser Ala Glu Leu Ala Ser Ala Pro Ala Pro Gly Glu
            20                  25                  30

Gly Pro Cys Gly Lys Val Val His Ile Met Pro Cys Leu Lys Phe
        35                  40                  45

Val Lys Gly Glu Glu Lys Glu Pro Ser Lys Ser Cys Cys Ser Gly Thr
    50                  55                  60

Lys Lys Leu Ser Glu Glu Val Lys Thr Thr Glu Gln Lys Arg Glu Ala
65                  70                  75                  80

Cys Lys Cys Ile Val Ala Ala Thr Lys Gly Ile Ser Gly Ile Lys Asn
                85                  90                  95

Glu Leu Val Ala Glu Val Pro Lys Lys Cys Gly Ile Thr Thr Thr Leu
            100                 105                 110

Pro Pro Ile Thr Ala Asp Phe Asp Cys Ser Lys Ile Glu Ser Thr Ile
        115                 120                 125

Phe Arg Gly Tyr Tyr
        130

<210> SEQ ID NO 101
<211> LENGTH: 176
<212> TYPE: PRT
<213> ORGANISM: Parietaria judaica

<400> SEQUENCE: 101

Met Arg Thr Val Ser Ala Pro Ser Ala Val Ala Leu Val Val Ile Val
1               5                   10                  15

Ala Ala Gly Leu Ala Trp Thr Ser Leu Ala Ser Val Ala Pro Pro Ala
            20                  25                  30

Pro Ala Pro Gly Ser Glu Glu Thr Cys Gly Thr Val Val Arg Ala Leu
        35                  40                  45

Met Pro Cys Leu Pro Phe Val Gln Gly Lys Glu Lys Glu Pro Ser Lys
    50                  55                  60

Gly Cys Cys Ser Gly Ala Lys Arg Leu Asp Gly Glu Thr Lys Thr Gly
65                  70                  75                  80

Leu Gln Arg Val His Ala Cys Glu Cys Ile Gln Thr Ala Met Lys Thr
                85                  90                  95

Tyr Ser Asp Ile Asp Gly Lys Leu Val Ser Glu Val Pro Lys His Cys
            100                 105                 110

Gly Ile Val Asp Ser Lys Leu Pro Pro Ile Asp Val Asn Met Asp Cys
        115                 120                 125

Lys Thr Leu Gly Val Val Pro Arg Gln Pro Gln Leu Pro Val Ser Leu
    130                 135                 140

Arg His Gly Pro Val Thr Gly Pro Ser Asp Pro Ala His Lys Ala Arg
145                 150                 155                 160
```

Leu Glu Arg Pro Gln Ile Arg Val Pro Pro Ala Pro Glu Lys Ala
            165                 170                 175

<210> SEQ ID NO 102
<211> LENGTH: 138
<212> TYPE: PRT
<213> ORGANISM: Parietaria judaica

<400> SEQUENCE: 102

Met Arg Thr Val Ser Ala Arg Ser Ser Val Ala Leu Val Val Ile Val
1               5                   10                  15

Ala Ala Val Leu Val Trp Thr Ser Ala Ser Val Ala Pro Ala Pro
            20                  25                  30

Ala Pro Gly Ser Glu Glu Thr Cys Gly Thr Val Val Gly Ala Leu Met
            35                  40                  45

Pro Cys Leu Pro Phe Val Gln Gly Lys Glu Lys Glu Pro Ser Lys Gly
    50                  55                  60

Cys Cys Ser Gly Ala Lys Arg Leu Asp Gly Glu Thr Lys Thr Gly Pro
65                  70                  75                  80

Gln Arg Val His Ala Cys Glu Cys Ile Gln Thr Ala Met Lys Thr Tyr
                85                  90                  95

Ser Asp Ile Asp Gly Lys Leu Val Ser Glu Val Pro Lys His Cys Gly
            100                 105                 110

Ile Val Asp Ser Lys Leu Pro Pro Ile Asp Val Asn Met Asp Cys Lys
        115                 120                 125

Thr Leu Gly Val Leu His Tyr Lys Gly Asn
    130                 135

<210> SEQ ID NO 103
<211> LENGTH: 143
<212> TYPE: PRT
<213> ORGANISM: Parietaria judaica

<400> SEQUENCE: 103

Met Val Arg Ala Leu Met Pro Cys Leu Pro Phe Val Gln Gly Lys Glu
1               5                   10                  15

Lys Glu Pro Ser Lys Gly Cys Cys Ser Gly Ala Lys Arg Leu Asp Gly
            20                  25                  30

Glu Thr Lys Thr Gly Pro Gln Arg Val His Ala Cys Glu Cys Ile Gln
        35                  40                  45

Thr Ala Met Lys Thr Tyr Ser Asp Ile Asp Gly Lys Leu Val Ser Glu
    50                  55                  60

Val Pro Lys His Cys Gly Ile Val Asp Ser Lys Leu Pro Pro Ile Asp
65                  70                  75                  80

Val Asn Met Asp Cys Lys Thr Val Gly Val Val Pro Arg Gln Pro Gln
                85                  90                  95

Leu Pro Val Ser Leu Arg His Gly Pro Val Thr Gly Pro Ser Arg Ser
            100                 105                 110

Arg Pro Pro Thr Lys His Gly Trp Arg Asp Pro Arg Leu Glu Phe Arg
        115                 120                 125

Pro Pro His Arg Lys Lys Pro Asn Pro Ala Phe Ser Thr Leu Gly
    130                 135                 140

<210> SEQ ID NO 104
<211> LENGTH: 263
<212> TYPE: PRT
<213> ORGANISM: Phleum pratense

<400> SEQUENCE: 104

| Met | Ala | Ser | Ser | Ser | Val | Leu | Leu | Val | Val | Leu | Phe | Ala | Val |
| 1 | | | | 5 | | | | | 10 | | | | 15 |

| Phe | Leu | Gly | Ser | Ala | Tyr | Gly | Ile | Pro | Lys | Val | Pro | Gly | Pro | Asn |
| | | | 20 | | | | | 25 | | | | | 30 | |

| Ile | Thr | Ala | Thr | Tyr | Gly | Asp | Lys | Trp | Leu | Asp | Ala | Lys | Ser | Thr | Trp |
| | | | 35 | | | | | 40 | | | | | 45 | | |

| Tyr | Gly | Lys | Pro | Thr | Gly | Ala | Gly | Pro | Lys | Asp | Asn | Gly | Gly | Ala | Cys |
| | 50 | | | | | 55 | | | | | 60 | | | | |

| Gly | Tyr | Lys | Asp | Val | Asp | Lys | Pro | Pro | Phe | Ser | Gly | Met | Thr | Gly | Cys |
| 65 | | | | | 70 | | | | | 75 | | | | | 80 |

| Gly | Asn | Thr | Pro | Ile | Phe | Lys | Ser | Gly | Arg | Gly | Cys | Gly | Ser | Cys | Phe |
| | | | | 85 | | | | | 90 | | | | | 95 | |

| Glu | Ile | Lys | Cys | Thr | Lys | Pro | Glu | Ala | Cys | Ser | Gly | Glu | Pro | Val | Val |
| | | | 100 | | | | | 105 | | | | | 110 | | |

| Val | His | Ile | Thr | Asp | Asp | Asn | Glu | Glu | Pro | Ile | Ala | Pro | Tyr | His | Phe |
| | | | 115 | | | | | 120 | | | | | 125 | | |

| Asp | Leu | Ser | Gly | His | Ala | Phe | Gly | Ala | Met | Ala | Lys | Lys | Gly | Asp | Glu |
| | | 130 | | | | | 135 | | | | | 140 | | | |

| Gln | Lys | Leu | Arg | Ser | Ala | Gly | Glu | Leu | Glu | Leu | Gln | Phe | Arg | Arg | Val |
| 145 | | | | | 150 | | | | | 155 | | | | | 160 |

| Lys | Cys | Lys | Tyr | Pro | Glu | Gly | Thr | Lys | Val | Thr | Phe | His | Val | Glu | Lys |
| | | | | 165 | | | | | 170 | | | | | 175 | |

| Gly | Ser | Asn | Pro | Asn | Tyr | Leu | Ala | Leu | Leu | Val | Lys | Tyr | Val | Asn | Gly |
| | | | 180 | | | | | 185 | | | | | 190 | | |

| Asp | Gly | Asp | Val | Val | Ala | Val | Asp | Ile | Lys | Glu | Lys | Gly | Lys | Asp | Lys |
| | | 195 | | | | | 200 | | | | | 205 | | | |

| Trp | Ile | Glu | Leu | Lys | Glu | Ser | Trp | Gly | Ala | Ile | Trp | Arg | Ile | Asp | Thr |
| 210 | | | | | 215 | | | | | 220 | | | | | |

| Pro | Asp | Lys | Leu | Thr | Gly | Pro | Phe | Thr | Val | Arg | Tyr | Thr | Thr | Glu | Gly |
| 225 | | | | | 230 | | | | | 235 | | | | | 240 |

| Gly | Thr | Lys | Thr | Glu | Ala | Glu | Asp | Val | Ile | Pro | Glu | Gly | Trp | Lys | Ala |
| | | | | 245 | | | | | 250 | | | | | 255 | |

| Asp | Thr | Ser | Tyr | Glu | Ser | Lys |
| | | | | 260 | | |

<210> SEQ ID NO 105
<211> LENGTH: 262
<212> TYPE: PRT
<213> ORGANISM: Phleum pratense

<400> SEQUENCE: 105

| Met | Ala | Ser | Ser | Ser | Val | Leu | Leu | Val | Val | Ala | Leu | Phe | Ala | Val |
| 1 | | | | 5 | | | | | 10 | | | | | 15 |

| Phe | Leu | Gly | Ser | Ala | His | Gly | Ile | Pro | Lys | Val | Pro | Gly | Pro | Asn |
| | | | 20 | | | | | 25 | | | | | 30 | |

| Ile | Thr | Ala | Thr | Tyr | Gly | Asp | Lys | Trp | Leu | Asp | Ala | Lys | Ser | Thr | Trp |
| | | | 35 | | | | | 40 | | | | | 45 | | |

| Tyr | Gly | Lys | Pro | Thr | Ala | Ala | Gly | Pro | Lys | Asp | Asn | Gly | Gly | Ala | Cys |
| | 50 | | | | | 55 | | | | | 60 | | | | |

| Gly | Tyr | Lys | Asp | Val | Asp | Lys | Pro | Pro | Phe | Ser | Gly | Met | Thr | Gly | Cys |
| 65 | | | | | 70 | | | | | 75 | | | | | 80 |

| Gly | Asn | Thr | Pro | Ile | Phe | Lys | Ser | Gly | Arg | Gly | Cys | Gly | Ser | Cys | Phe |
| | | | | 85 | | | | | 90 | | | | | 95 | |

| Glu | Ile | Lys | Cys | Thr | Lys | Pro | Glu | Ala | Cys | Ser | Gly | Glu | Pro | Val | Val |

```
                100                 105                 110
Val His Ile Thr Asp Asp Asn Glu Glu Pro Ile Ala Ala Tyr His Phe
                115                 120                 125

Asp Leu Ser Gly Ile Ala Phe Gly Ser Met Ala Lys Lys Gly Asp Glu
                130                 135                 140

Gln Lys Leu Arg Ser Ala Gly Glu Val Glu Ile Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Phe Ser Gly Asp
                180                 185                 190

Gly Asp Val Val Ala Val Asp Ile Lys Glu Lys Gly Lys Asp Lys Trp
                195                 200                 205

Ile Ala Leu Lys Glu Ser Trp Gly Ala Ile Trp Arg Ile Asp Thr Pro
                210                 215                 220

Glu Val Leu Lys Gly Pro Phe Thr Val Arg Tyr Thr Thr Glu Gly Gly
225                 230                 235                 240

Thr Lys Ala Arg Ala Lys Asp Val Ile Pro Glu Gly Trp Lys Ala Asp
                245                 250                 255

Thr Ala Tyr Glu Ser Lys
                260

<210> SEQ ID NO 106
<211> LENGTH: 122
<212> TYPE: PRT
<213> ORGANISM: Phleum pratense

<400> SEQUENCE: 106

Met Ser Met Ala Ser Ser Ser Ser Ser Leu Leu Ala Met Ala Val
1               5                   10                  15

Leu Ala Ala Leu Phe Ala Gly Ala Trp Cys Val Pro Lys Val Thr Phe
                20                  25                  30

Thr Val Glu Lys Gly Ser Asn Glu Lys His Leu Ala Val Leu Val Lys
                35                  40                  45

Tyr Glu Gly Asp Thr Met Ala Glu Val Glu Leu Arg Glu His Gly Ser
                50                  55                  60

Asp Glu Trp Val Ala Met Thr Lys Gly Glu Gly Gly Val Trp Thr Phe
65                  70                  75                  80

Asp Ser Glu Glu Pro Leu Gln Gly Pro Phe Asn Phe Arg Phe Leu Thr
                85                  90                  95

Glu Lys Gly Met Lys Asn Val Phe Asp Asp Val Val Pro Glu Lys Tyr
                100                 105                 110

Thr Ile Gly Ala Thr Tyr Ala Pro Glu Glu
                115                 120

<210> SEQ ID NO 107
<211> LENGTH: 276
<212> TYPE: PRT
<213> ORGANISM: Phleum pratense

<400> SEQUENCE: 107

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
                20                  25                  30

Lys Ile Asn Asp Gly Phe Lys Ala Ala Leu Ala Ala Ala Ala Gly Val
                35                  40                  45
```

```
Pro Pro Ala Asp Lys Tyr Lys Thr Phe Val Ala Thr Phe Gly Ala Ala
    50                  55                  60

Ser Asn Lys Ala Phe Ala Glu Gly Leu Ser Ala Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
                100                 105                 110

Tyr Asp Ala Tyr Val Ala Thr Leu Ser Glu Ala Leu Arg Ile Ile Ala
                115                 120                 125

Gly Thr Leu Glu Val His Ala Val Lys Pro Ala Ala Glu Glu Val Lys
            130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
                180                 185                 190

Gly Gly Ala Tyr Glu Ser Tyr Lys Phe Ile Pro Ala Leu Glu Ala Ala
            195                 200                 205

Val Lys Gln Ala Tyr Ala Ala Thr Val Ala Thr Ala Pro Glu Val Lys
210                 215                 220

Tyr Thr Val Phe Glu Thr Ala Leu Lys Lys Ala Phe Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
            260                 265                 270

Gly Tyr Lys Val
        275

<210> SEQ ID NO 108
<211> LENGTH: 276
<212> TYPE: PRT
<213> ORGANISM: Phleum pratense

<400> SEQUENCE: 108

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
                20                  25                  30

Lys Ile Asn Asp Gly Phe Lys Ala Ala Leu Ala Ala Ala Ala Gly Val
            35                  40                  45

Pro Pro Ala Asp Lys Tyr Lys Thr Phe Val Ala Thr Phe Gly Ala Ala
    50                  55                  60

Ser Asn Lys Ala Phe Ala Glu Gly Leu Ser Ala Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
                100                 105                 110

Tyr Asp Ala Tyr Val Ala Thr Leu Ser Glu Ala Leu Arg Ile Ile Ala
                115                 120                 125

Gly Thr Leu Glu Val His Ala Val Lys Pro Ala Ala Glu Glu Val Lys
            130                 135                 140
```

```
Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Ala Ile Lys Ala Ser Thr
            180                 185                 190

Gly Gly Ala Tyr Glu Ser Tyr Lys Phe Ile Pro Ala Leu Glu Ala Ala
            195                 200                 205

Val Lys Gln Ala Tyr Ala Ala Thr Val Ala Thr Ala Pro Glu Val Lys
            210                 215                 220

Tyr Thr Val Phe Glu Thr Ala Leu Lys Lys Ala Ile Thr Ala Met Ser
225                 230                 235                 240

Glu Ala Gln Lys Ala Ala Lys Pro Ala Thr Glu Ala Thr Ala
            245                 250                 255

Thr Ala Ala Val Gly Ala Ala Thr Gly Ala Ala Thr Ala Ala Thr Gly
            260                 265                 270

Gly Tyr Lys Val
            275

<210> SEQ ID NO 109
<211> LENGTH: 284
<212> TYPE: PRT
<213> ORGANISM: Phleum pratense

<400> SEQUENCE: 109

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
                20                  25                  30

Gly Ala Ala Ala Gly Lys Ala Thr Thr Glu Glu Gln Lys Leu Ile Glu
            35                  40                  45

Asp Ile Asn Val Gly Phe Lys Ala Ala Val Ala Ala Ala Ala Ser Val
50                  55                  60

Pro Ala Ala Asp Lys Phe Lys Thr Phe Glu Ala Ala Phe Thr Ser Ser
65                  70                  75                  80

Ser Lys Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
            115                 120                 125

Ile Ala Gly Ala Leu Glu Val His Ala Val Lys Pro Val Thr Glu Glu
130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
            195                 200                 205

Leu Glu Ala Ala Val Lys Gln Ala Tyr Ala Ala Thr Val Ala Ala Ala
            210                 215                 220

Pro Gln Val Lys Tyr Ala Val Phe Glu Ala Ala Leu Thr Lys Ala Ile
225                 230                 235                 240
```

```
Thr Ala Met Ser Glu Val Gln Lys Val Ser Gln Pro Ala Thr Gly Ala
            245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
            275                 280

<210> SEQ ID NO 110
<211> LENGTH: 286
<212> TYPE: PRT
<213> ORGANISM: Phleum pratense

<400> SEQUENCE: 110

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Gly Ala Gly Val Gln Pro Ala Asp Lys Tyr
50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
            115                 120                 125

Thr Leu Ser Glu Ala Leu Arg Ile Ile Ala Gly Thr Leu Glu Val His
        130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Thr Ala Thr Ala Thr Ala Ala Val Gly Ala
            260                 265                 270

Ala Thr Gly Ala Ala Thr Ala Ala Thr Gly Gly Tyr Lys Val
            275                 280                 285

<210> SEQ ID NO 111
<211> LENGTH: 287
<212> TYPE: PRT
<213> ORGANISM: Phleum pratense

<400> SEQUENCE: 111
```

```
Met Ala Val Gln Lys Tyr Thr Val Ala Leu Phe Leu Ala Val Ala Leu
1               5                   10                  15

Val Ala Gly Pro Ala Ala Ser Tyr Ala Ala Asp Ala Gly Tyr Ala Pro
            20                  25                  30

Ala Thr Pro Ala Ala Ala Gly Ala Glu Ala Gly Lys Ala Thr Thr Glu
            35                  40                  45

Glu Gln Lys Leu Ile Glu Asp Ile Asn Val Gly Phe Lys Ala Ala Val
        50                  55                  60

Ala Ala Ala Ala Ser Val Pro Ala Ala Asp Lys Phe Lys Thr Phe Glu
65                  70                  75                  80

Ala Ala Phe Thr Ser Ser Lys Ala Ala Thr Ala Lys Ala Pro Gly
                85                  90                  95

Leu Val Pro Lys Leu Asp Ala Ala Tyr Ser Val Ser Tyr Lys Ala Ala
            100                 105                 110

Val Gly Ala Thr Pro Glu Ala Lys Phe Asp Ser Phe Val Ala Ser Leu
            115                 120                 125

Thr Glu Ala Leu Arg Val Ile Ala Gly Ala Leu Glu Val His Ala Val
            130                 135                 140

Lys Pro Val Thr Glu Glu Pro Gly Met Ala Lys Ile Pro Ala Gly Glu
145                 150                 155                 160

Leu Gln Ile Ile Asp Lys Ile Asp Ala Ala Phe Lys Val Ala Ala Thr
                165                 170                 175

Ala Ala Ala Thr Ala Pro Ala Asp Thr Val Phe Glu Ala Ala Phe Asn
            180                 185                 190

Lys Ala Ile Lys Glu Ser Thr Gly Gly Ala Tyr Asp Thr Tyr Lys Cys
            195                 200                 205

Ile Pro Ser Leu Glu Ala Ala Val Lys Gln Tyr Ala Ala Thr Val
            210                 215                 220

Ala Ala Ala Pro Gln Val Lys Tyr Ala Val Phe Glu Ala Ala Leu Thr
225                 230                 235                 240

Lys Ala Ile Thr Ala Met Ser Glu Val Gln Lys Val Ser Gln Pro Ala
                245                 250                 255

Thr Gly Ala Ala Thr Val Ala Ala Gly Ala Ala Thr Thr Ala Ala Gly
            260                 265                 270

Ala Ala Ser Gly Ala Ala Thr Val Ala Gly Gly Tyr Lys Val
            275                 280                 285
```

<210> SEQ ID NO 112
<211> LENGTH: 290
<212> TYPE: PRT
<213> ORGANISM: Phleum pratense

<400> SEQUENCE: 112

```
Met Ala Val Gln Lys Tyr Thr Val Ala Leu Phe Leu Ala Val Ala Leu
1               5                   10                  15

Val Ala Gly Pro Ala Ala Ser Tyr Ala Ala Asp Ala Gly Tyr Ala Pro
            20                  25                  30

Ala Thr Pro Ala Ala Ala Gly Ala Glu Ala Gly Lys Ala Thr Thr Glu
            35                  40                  45

Glu Gln Lys Leu Ile Glu Asp Ile Asn Val Gly Phe Lys Ala Ala Val
        50                  55                  60

Ala Ala Ala Ala Ser Val Pro Ala Ala Asp Lys Phe Lys Thr Phe Glu
65                  70                  75                  80

Ala Ala Phe Thr Ser Ser Lys Ala Ala Thr Ala Lys Ala Pro Gly
                85                  90                  95
```

```
Leu Val Pro Lys Leu Asp Ala Ala Tyr Ser Val Ala Tyr Lys Ala Ala
                100                 105                 110

Val Gly Ala Thr Pro Glu Ala Lys Phe Asp Ser Phe Val Ala Ser Leu
            115                 120                 125

Thr Glu Ala Leu Arg Val Ile Ala Gly Ala Leu Glu Val His Ala Val
        130                 135                 140

Lys Pro Val Thr Glu Asp Pro Ala Trp Pro Lys Ile Pro Ala Gly Glu
145                 150                 155                 160

Leu Gln Ile Ile Asp Lys Ile Asp Ala Ala Phe Lys Val Ala Ala Thr
                165                 170                 175

Ala Ala Ala Thr Ala Pro Ala Asp Lys Phe Thr Val Phe Glu Ala
            180                 185                 190

Ala Phe Asn Lys Ala Ile Lys Glu Ser Thr Gly Gly Ala Tyr Asp Thr
        195                 200                 205

Tyr Lys Cys Ile Pro Ser Leu Glu Ala Ala Val Lys Gln Ala Tyr Ala
    210                 215                 220

Ala Thr Val Ala Ala Pro Gln Val Lys Tyr Ala Val Phe Glu Ala
225                 230                 235                 240

Ala Leu Thr Lys Ala Ile Thr Ala Met Ser Glu Val Gln Lys Val Ser
                245                 250                 255

Gln Pro Ala Thr Gly Ala Ala Thr Val Ala Ala Gly Ala Ala Thr Thr
            260                 265                 270

Ala Thr Gly Ala Ala Ser Gly Ala Ala Thr Val Ala Ala Gly Gly Tyr
        275                 280                 285

Lys Val
    290

<210> SEQ ID NO 113
<211> LENGTH: 265
<212> TYPE: PRT
<213> ORGANISM: Phleum pratense

<400> SEQUENCE: 113

Ala Asp Ala Gly Tyr Ala Pro Ala Thr Pro Ala Ala Ala Gly Ala Glu
1               5                   10                  15

Ala Gly Lys Ala Thr Thr Glu Glu Gln Lys Leu Ile Glu Asp Ile Asn
            20                  25                  30

Val Gly Phe Lys Ala Ala Val Ala Ala Ala Ser Val Pro Ala Ala
        35                  40                  45

Asp Lys Phe Lys Thr Phe Glu Ala Ala Phe Thr Ser Ser Ser Lys Ala
    50                  55                  60

Ala Thr Ala Lys Ala Pro Gly Leu Val Pro Lys Leu Asp Ala Ala Tyr
65                  70                  75                  80

Ser Val Ala Tyr Lys Ala Ala Val Gly Ala Thr Pro Glu Ala Lys Phe
                85                  90                  95

Asp Ser Phe Val Ala Ser Leu Thr Glu Ala Leu Arg Val Ile Ala Gly
            100                 105                 110

Ala Leu Glu Val His Ala Val Lys Pro Val Thr Glu Glu Pro Gly Met
        115                 120                 125

Ala Lys Ile Pro Ala Gly Glu Leu Gln Ile Ile Asp Lys Ile Asp Ala
    130                 135                 140

Ala Phe Lys Val Ala Ala Thr Ala Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175
```

```
Thr Gly Gly Ala Tyr Asp Thr Tyr Lys Cys Ile Pro Ser Leu Glu Ala
            180                 185                 190

Ala Val Lys Gln Ala Tyr Ala Ala Thr Val Ala Ala Ala Pro Gln Val
            195                 200                 205

Lys Tyr Ala Val Phe Glu Ala Ala Leu Thr Lys Ala Ile Thr Ala Met
            210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                    245                 250                 255

Thr Val Ala Ala Gly Gly Tyr Lys Val
            260                 265

<210> SEQ ID NO 114
<211> LENGTH: 295
<212> TYPE: PRT
<213> ORGANISM: Phleum pratense

<400> SEQUENCE: 114

Ser Val Lys Arg Ser Asn Gly Ser Ala Glu Val His Arg Gly Ala Val
1               5                   10                  15

Pro Arg Arg Gly Pro Arg Gly Gly Pro Gly Arg Ser Tyr Ala Ala Asp
            20                  25                  30

Ala Gly Tyr Ala Pro Ala Thr Pro Ala Ala Gly Glu Ala Gly
            35                  40                  45

Lys Ala Thr Thr Glu Glu Gln Lys Leu Ile Glu Asp Ile Asn Val Gly
    50                  55                  60

Phe Lys Ala Ala Val Ala Ala Ala Ser Val Pro Ala Ala Asp Lys
65                  70                  75                  80

Phe Lys Thr Phe Glu Ala Ala Phe Thr Ser Ser Lys Ala Thr
                85                  90                  95

Ala Lys Ala Pro Gly Leu Val Pro Lys Leu Asp Ala Ala Tyr Ser Val
            100                 105                 110

Ala Tyr Lys Ala Ala Val Gly Ala Thr Pro Glu Ala Lys Phe Asp Ser
            115                 120                 125

Phe Val Ala Ser Leu Thr Glu Ala Leu Arg Val Ile Ala Gly Ala Leu
            130                 135                 140

Glu Val His Ala Val Lys Pro Val Thr Glu Glu Pro Gly Met Ala Lys
145                 150                 155                 160

Ile Pro Ala Gly Glu Leu Gln Ile Ile Asp Lys Ile Asp Ala Ala Phe
                165                 170                 175

Lys Val Ala Ala Thr Ala Ala Thr Ala Pro Ala Asp Asp Lys Phe
            180                 185                 190

Thr Val Phe Glu Ala Ala Phe Asn Lys Ala Ile Lys Glu Ser Thr Gly
            195                 200                 205

Gly Ala Tyr Asp Thr Tyr Lys Cys Ile Pro Ser Leu Gly Ala Ala Val
            210                 215                 220

Lys Gln Ala Tyr Ala Ala Thr Val Ala Ala Pro Gln Val Lys Tyr
225                 230                 235                 240

Ala Val Phe Glu Ala Ala Leu Thr Lys Ala Ile Thr Ala Met Ser Glu
                245                 250                 255

Val Gln Lys Val Ser Gln Pro Ala Thr Gly Ala Ala Thr Val Ala Ala
            260                 265                 270

Gly Ala Ala Thr Thr Ala Ala Gly Ala Ala Ser Gly Ala Ala Thr Val
            275                 280                 285
```

```
Ala Ala Gly Gly Tyr Lys Val
    290             295

<210> SEQ ID NO 115
<211> LENGTH: 312
<212> TYPE: PRT
<213> ORGANISM: Phleum pratense

<400> SEQUENCE: 115

Met Ala Val His Gln Tyr Thr Val Ala Leu Phe Leu Ala Val Ala Leu
1               5                   10                  15

Val Ala Gly Pro Ala Gly Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
        35                  40                  45

Ala Pro Ala Gly Ala Glu Pro Ala Gly Lys Ala Thr Thr Glu Glu Gln
    50                  55                  60

Lys Leu Ile Glu Lys Ile Asn Ala Gly Phe Lys Ala Ala Leu Ala Ala
65                  70                  75                  80

Ala Ala Gly Val Pro Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Ser Lys Ala Ala Leu Thr Ser Lys
        115                 120                 125

Leu Asp Ala Ala Tyr Lys Leu Ala Tyr Lys Thr Ala Glu Gly Ala Thr
    130                 135                 140

Pro Glu Ala Lys Tyr Asp Ala Tyr Val Ala Thr Val Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Ala Lys Pro Ala Ala Ala Ala
        275                 280                 285

Thr Ala Thr Ala Thr Ala Ala Val Gly Ala Ala Thr Gly Ala Ala Thr
    290                 295                 300

Ala Ala Thr Gly Gly Tyr Lys Val
305                 310

<210> SEQ ID NO 116
<211> LENGTH: 276
<212> TYPE: PRT
<213> ORGANISM: Phleum pratense

<400> SEQUENCE: 116

Ala Asp Leu Gly Tyr Gly Gly Pro Ala Thr Pro Ala Ala Pro Ala Glu
```

```
                1               5                  10                 15
Ala Ala Pro Ala Gly Lys Ala Thr Thr Glu Glu Gln Lys Leu Ile Glu
                    20                  25                  30

Lys Ile Asn Asp Gly Phe Lys Ala Ala Leu Ala Ala Ala Gly Val
            35                  40                  45

Pro Pro Ala Asp Lys Tyr Lys Thr Phe Val Ala Thr Phe Gly Ala Ala
        50                  55                  60

Ser Asn Lys Ala Phe Ala Glu Gly Leu Ser Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
                100                 105                 110

Tyr Asp Ala Tyr Val Ala Thr Leu Ser Glu Ala Leu Arg Ile Ile Ala
            115                 120                 125

Gly Thr Leu Glu Val His Ala Val Lys Pro Ala Glu Glu Val Lys
        130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
            180                 185                 190

Gly Gly Ala Tyr Glu Ser Tyr Lys Phe Ile Pro Ala Leu Glu Ala Ala
        195                 200                 205

Val Lys Gln Ala Tyr Ala Ala Thr Val Ala Thr Ala Pro Glu Val Lys
    210                 215                 220

Tyr Thr Val Phe Glu Thr Ala Leu Lys Lys Ala Phe Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
            260                 265                 270

Gly Tyr Lys Val
        275

<210> SEQ ID NO 117
<211> LENGTH: 284
<212> TYPE: PRT
<213> ORGANISM: Phleum pratense

<400> SEQUENCE: 117

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Thr Glu Glu Gln Lys Leu Ile Glu
        35                  40                  45

Asp Ile Asn Val Gly Phe Lys Ala Ala Val Ala Ala Ala Ala Ser Val
    50                  55                  60

Pro Ala Ala Asp Lys Phe Lys Thr Phe Glu Ala Ala Phe Thr Ser Ser
65                  70                  75                  80

Ser Lys Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
```

```
                100             105                 110
Ala Lys Phe Asp Ser Phe Val Ala Ser Leu Thr Glu Ala Leu Arg Val
            115                 120                 125

Ile Ala Gly Ala Leu Glu Val His Ala Val Lys Pro Val Thr Glu Glu
        130                 135             140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
            195                 200                 205

Leu Glu Ala Ala Val Lys Gln Ala Tyr Ala Ala Thr Val Ala Ala Ala
        210                 215                 220

Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
                245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
            275                 280

<210> SEQ ID NO 118
<211> LENGTH: 286
<212> TYPE: PRT
<213> ORGANISM: Phleum pratense

<400> SEQUENCE: 118

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Gly Ala Gly Val Gln Pro Ala Asp Lys Tyr
    50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
        115                 120                 125

Thr Leu Ser Glu Ala Leu Arg Ile Ile Ala Gly Thr Leu Glu Val His
    130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
```

-continued

```
                195                 200                 205
Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Thr Ala Thr Ala Thr Ala Ala Val Gly Ala
                260                 265                 270

Ala Thr Gly Ala Ala Thr Ala Ala Thr Gly Gly Tyr Lys Val
                275                 280                 285
```

<210> SEQ ID NO 119
<211> LENGTH: 281
<212> TYPE: PRT
<213> ORGANISM: Phleum pratense

<400> SEQUENCE: 119

```
Ala Val Pro Arg Arg Gly Pro Arg Gly Gly Pro Gly Arg Ser Tyr Ala
1               5                   10                  15

Ala Asp Ala Gly Tyr Ala Pro Ala Thr Pro Ala Ala Ala Gly Ala Glu
                20                  25                  30

Ala Gly Lys Ala Thr Thr Glu Glu Gln Lys Leu Ile Glu Asp Ile Asn
            35                  40                  45

Val Gly Phe Lys Ala Ala Val Ala Ala Ala Ser Val Pro Ala Gly
    50                  55                  60

Asp Lys Phe Lys Thr Phe Glu Ala Ala Phe Thr Ser Ser Ser Lys Ala
65                  70                  75                  80

Ala Thr Ala Lys Ala Pro Gly Leu Val Pro Lys Leu Asp Ala Ala Tyr
                85                  90                  95

Ser Val Ala Tyr Lys Ala Ala Val Gly Ala Thr Pro Glu Ala Lys Phe
                100                 105                 110

Asp Ser Phe Val Ala Ser Leu Thr Glu Ala Leu Arg Val Ile Ala Gly
            115                 120                 125

Ala Leu Glu Val His Ala Val Lys Pro Val Thr Glu Glu Pro Gly Met
130                 135                 140

Ala Lys Ile Pro Ala Gly Glu Leu Gln Ile Ile Asp Lys Ile Asp Ala
145                 150                 155                 160

Ala Phe Lys Val Ala Ala Thr Ala Ala Thr Ala Pro Ala Asp Asp
                165                 170                 175

Lys Phe Thr Val Phe Glu Ala Ala Phe Asn Lys Ala Ile Lys Glu Ser
                180                 185                 190

Thr Gly Gly Ala Tyr Asp Thr Tyr Lys Cys Ile Pro Ser Leu Glu Ala
            195                 200                 205

Ala Val Lys Gln Ala Tyr Ala Ala Thr Val Ala Ala Pro Gln Val
    210                 215                 220

Lys Tyr Ala Val Phe Glu Ala Ala Leu Thr Lys Ala Ile Thr Ala Met
225                 230                 235                 240

Ser Glu Val Gln Lys Val Ser Gln Pro Ala Thr Gly Ala Ala Thr Val
                245                 250                 255

Ala Ala Gly Ala Ala Thr Thr Ala Thr Gly Ala Ala Ser Gly Ala Ala
                260                 265                 270

Thr Val Ala Ala Gly Gly Tyr Lys Val
                275                 280
```

```
<210> SEQ ID NO 120
<211> LENGTH: 280
<212> TYPE: PRT
<213> ORGANISM: Phleum pratense

<400> SEQUENCE: 120

Met Ala Val Pro Arg Gly Pro Arg Gly Pro Gly Arg Ser Tyr
1               5                   10                  15

Thr Ala Asp Ala Gly Tyr Ala Pro Ala Thr Pro Ala Ala Gly Ala
            20                  25                  30

Ala Ala Gly Lys Ala Thr Thr Glu Glu Gln Lys Leu Ile Glu Asp Ile
        35                  40                  45

Asn Val Gly Phe Lys Ala Ala Val Ala Ala Arg Gln Arg Pro Ala Ala
    50                  55                  60

Asp Lys Phe Lys Thr Phe Glu Ala Ala Ser Pro Arg His Pro Arg Pro
65                  70                  75                  80

Leu Arg Gln Gly Ala Gly Leu Val Pro Lys Leu Asp Ala Ala Tyr Ser
                85                  90                  95

Val Ala Tyr Lys Ala Ala Val Gly Ala Thr Pro Glu Ala Lys Phe Asp
            100                 105                 110

Ser Phe Val Ala Ser Leu Thr Glu Ala Leu Arg Val Ile Ala Gly Ala
        115                 120                 125

Leu Glu Val His Ala Val Lys Pro Val Thr Glu Glu Pro Gly Met Ala
    130                 135                 140

Lys Ile Pro Ala Gly Glu Leu Gln Ile Ile Asp Lys Ile Asp Ala Ala
145                 150                 155                 160

Phe Lys Val Ala Ala Thr Ala Ala Thr Ala Pro Ala Asp Asp Lys
                165                 170                 175

Phe Thr Val Phe Glu Ala Ala Phe Asn Lys Ala Ile Lys Glu Ser Thr
            180                 185                 190

Gly Gly Ala Tyr Asp Thr Tyr Lys Cys Ile Pro Ser Leu Glu Ala Ala
        195                 200                 205

Val Lys Gln Ala Tyr Ala Ala Thr Val Ala Ala Ala Glu Val Lys
    210                 215                 220

Tyr Ala Val Phe Glu Ala Ala Leu Thr Lys Ala Ile Thr Ala Met Ser
225                 230                 235                 240

Glu Val Gln Lys Val Ser Gln Pro Ala Thr Gly Ala Ala Thr Val Ala
                245                 250                 255

Ala Gly Ala Ala Thr Thr Ala Ala Gly Ala Ala Ser Gly Ala Ala Thr
            260                 265                 270

Val Ala Ala Gly Gly Tyr Lys Val
        275                 280

<210> SEQ ID NO 121
<211> LENGTH: 312
<212> TYPE: PRT
<213> ORGANISM: Phleum pratense

<400> SEQUENCE: 121

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
        35                  40                  45

Ala Pro Ala Glu Ala Ala Pro Ala Gly Lys Ala Thr Thr Glu Glu Gln
    50                  55                  60
```

```
Lys Leu Ile Glu Lys Ile Asn Ala Gly Phe Lys Ala Ala Leu Ala Ala
 65                  70                  75                  80

Ala Ala Gly Val Gln Pro Ala Asp Lys Tyr Arg Thr Phe Val Ala Thr
                 85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Ala Asn Ala Ala Pro
        195                 200                 205

Ala Asn Asp Lys Phe Thr Val Phe Glu Ala Ala Phe Asn Asp Ala Ile
210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Thr Val Ala Thr Ala
                245                 250                 255

Pro Glu Val Lys Tyr Thr Val Phe Glu Thr Ala Leu Lys Lys Ala Ile
                260                 265                 270

Thr Ala Met Ser Glu Ala Gln Lys Ala Ala Lys Pro Ala Ala Ala Ala
            275                 280                 285

Thr Ala Thr Ala Thr Ala Ala Val Gly Ala Ala Thr Gly Ala Ala Thr
        290                 295                 300

Ala Ala Thr Gly Gly Tyr Lys Val
305                 310

<210> SEQ ID NO 122
<211> LENGTH: 257
<212> TYPE: PRT
<213> ORGANISM: Phleum pratense

<400> SEQUENCE: 122

Glu Ala Pro Ala Gly Lys Ala Thr Thr Glu Glu Gln Lys Leu Ile Glu
  1               5                  10                  15

Lys Ile Asn Ala Gly Phe Lys Ala Ala Leu Ala Arg Arg Leu Gln Pro
                 20                  25                  30

Ala Asp Lys Tyr Arg Thr Phe Val Ala Thr Phe Gly Pro Ala Ser Asn
             35                  40                  45

Lys Ala Phe Ala Glu Gly Leu Ser Gly Glu Pro Lys Gly Ala Ala Glu
         50                  55                  60

Ser Ser Lys Ala Ala Leu Thr Ser Lys Leu Asp Ala Ala Tyr Lys
 65                  70                  75                  80

Leu Ala Tyr Lys Thr Ala Glu Gly Ala Thr Pro Glu Ala Lys Tyr Asp
                 85                  90                  95

Ala Tyr Val Ala Thr Leu Ser Glu Ala Leu Arg Ile Ile Ala Gly Thr
            100                 105                 110

Leu Glu Val His Ala Val Lys Pro Ala Ala Glu Glu Val Lys Val Ile
        115                 120                 125
```

Pro Ala Ala Glu Leu Gln Val Ile Glu Lys Val Asp Ala Ala Phe Lys
            130                 135                 140

Val Ala Ala Thr Ala Ala Asn Ala Ala Pro Ala Asn Asp Lys Phe Thr
145                 150                 155                 160

Val Phe Glu Ala Ala Phe Asn Asp Glu Ile Lys Ala Ser Thr Gly Gly
                165                 170                 175

Ala Tyr Glu Ser Tyr Lys Phe Ile Pro Ala Leu Glu Ala Ala Val Lys
            180                 185                 190

Gln Ala Tyr Ala Ala Thr Val Ala Thr Ala Pro Glu Val Lys Tyr Thr
                195                 200                 205

Val Phe Glu Thr Ala Leu Lys Lys Ala Ile Thr Ala Met Ser Glu Ala
            210                 215                 220

Gln Lys Ala Ala Lys Pro Pro Leu Pro Pro Pro Gln Pro Pro
225                 230                 235                 240

Pro Leu Ala Ala Thr Gly Ala Ala Thr Ala Thr Gly Gly Tyr Lys
                245                 250                 255

Val

<210> SEQ ID NO 123
<211> LENGTH: 312
<212> TYPE: PRT
<213> ORGANISM: Phleum pratense

<400> SEQUENCE: 123

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
                20                  25                  30

Ala Thr Pro Ala Ala Pro Ala Ala Gly Tyr Thr Pro Ala Thr Pro Ala
            35                  40                  45

Ala Pro Ala Glu Ala Ala Pro Ala Gly Lys Ala Thr Thr Glu Glu Gln
        50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Thr Ala Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

```
Leu Glu Ala Ala Val Lys Gln Ala Tyr Ala Ala Thr Val Ala Thr Ala
                245                 250                 255
Pro Glu Val Lys Tyr Thr Val Phe Glu Thr Ala Leu Lys Lys Ala Ile
            260                 265                 270
Thr Ala Met Ser Glu Ala Gln Lys Ala Lys Pro Ala Ala Ala Ala
        275                 280                 285
Thr Ala Thr Ala Thr Ala Ala Val Gly Ala Ala Thr Gly Ala Ala Thr
    290                 295                 300
Ala Ala Thr Gly Gly Tyr Lys Val
305                 310
```

<210> SEQ ID NO 124
<211> LENGTH: 280
<212> TYPE: PRT
<213> ORGANISM: Phleum pratense

<400> SEQUENCE: 124

```
Met Ala Val Pro Arg Gly Pro Arg Gly Pro Gly Arg Ser Tyr
1               5                   10                  15
Thr Ala Asp Ala Gly Tyr Ala Pro Ala Thr Pro Ala Ala Gly Ala
            20                  25                  30
Ala Ala Gly Lys Ala Thr Thr Glu Glu Gln Lys Leu Ile Glu Asp Ile
        35                  40                  45
Asn Val Gly Phe Lys Ala Ala Val Ala Ala Arg Gln Arg Pro Ala Ala
50                  55                  60
Asp Lys Phe Lys Thr Phe Glu Ala Ala Ser Pro Arg His Pro Arg Pro
65                  70                  75                  80
Leu Arg Gln Gly Ala Gly Leu Val Pro Lys Leu Asp Ala Ala Tyr Ser
                85                  90                  95
Val Ala Tyr Lys Ala Ala Val Gly Ala Thr Pro Glu Ala Lys Phe Asp
            100                 105                 110
Ser Phe Val Ala Ser Leu Thr Glu Ala Leu Arg Val Ile Ala Gly Ala
        115                 120                 125
Leu Glu Val His Ala Val Lys Pro Val Thr Glu Glu Pro Gly Met Ala
    130                 135                 140
Lys Ile Pro Ala Gly Glu Leu Gln Ile Ile Asp Lys Ile Asp Ala Ala
145                 150                 155                 160
Phe Lys Val Ala Ala Thr Ala Ala Thr Ala Pro Ala Asp Asp Lys
                165                 170                 175
Phe Thr Val Phe Glu Ala Ala Phe Asn Lys Ala Ile Lys Glu Ser Thr
            180                 185                 190
Gly Gly Ala Tyr Asp Thr Tyr Lys Cys Ile Pro Ser Leu Glu Ala Ala
        195                 200                 205
Val Lys Gln Ala Tyr Ala Ala Thr Val Ala Ala Ala Glu Val Lys
    210                 215                 220
Tyr Ala Val Phe Glu Ala Ala Leu Thr Lys Ala Ile Thr Ala Met Ser
225                 230                 235                 240
Glu Val Gln Lys Val Ser Gln Pro Ala Thr Gly Ala Ala Thr Val Ala
                245                 250                 255
Ala Gly Ala Ala Thr Thr Ala Ala Gly Ala Ala Ser Gly Ala Ala Thr
            260                 265                 270
Val Ala Ala Gly Gly Tyr Lys Val
        275                 280
```

<210> SEQ ID NO 125
<211> LENGTH: 285

```
<212> TYPE: PRT
<213> ORGANISM: Phleum pratense

<400> SEQUENCE: 125

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Gly Ala Gly Val Gln Pro Ala Asp Lys Tyr
    50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
        115                 120                 125

Thr Leu Ser Glu Ala Leu Arg Ile Ile Ala Gly Thr Leu Glu Val His
    130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Pro Pro Leu Pro Pro Pro Gln Pro Pro Leu Ala Ala
            260                 265                 270

Thr Gly Ala Ala Thr Ala Ala Thr Gly Gly Tyr Lys Val
        275                 280                 285

<210> SEQ ID NO 126
<211> LENGTH: 312
<212> TYPE: PRT
<213> ORGANISM: Phleum pratense

<400> SEQUENCE: 126

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Thr Pro Ala
        35                  40                  45

Ala Pro Ala Glu Ala Ala Pro Ala Gly Lys Ala Thr Thr Glu Glu Gln
    50                  55                  60

Lys Leu Ile Glu Lys Ile Asn Ala Gly Phe Lys Ala Ala Leu Ala Ala
```

```
                65                  70                  75                  80
Ala Ala Gly Val Gln Pro Ala Asp Lys Tyr Arg Thr Phe Val Ala Thr
                    85                  90                  95

Phe Gly Ala Ala Ser Asn Lys Ala Phe Ala Glu Gly Leu Ser Gly Glu
                100                 105                 110

Pro Lys Gly Ala Ala Glu Ser Ser Lys Ala Ala Leu Thr Ser Lys
                115                 120                 125

Leu Asp Ala Ala Tyr Lys Leu Ala Tyr Lys Thr Ala Glu Gly Ala Thr
130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
                180                 185                 190

Val Asp Ala Ala Phe Lys Val Ala Thr Ala Ala Asn Ala Ala Pro
    195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Thr Val Ala Thr Ala
                245                 250                 255

Pro Glu Val Lys Tyr Thr Val Phe Glu Thr Ala Leu Lys Lys Ala Ile
                260                 265                 270

Thr Ala Met Ser Glu Ala Gln Lys Ala Lys Pro Ala Ala Ala
                275                 280                 285

Thr Ala Thr Ala Thr Ala Ala Val Gly Ala Ala Thr Gly Ala Ala Thr
    290                 295                 300

Ala Ala Thr Gly Gly Tyr Lys Val
305                 310

<210> SEQ ID NO 127
<211> LENGTH: 138
<212> TYPE: PRT
<213> ORGANISM: Phleum pratense

<400> SEQUENCE: 127

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
                20                  25                  30

Thr Glu Glu Gln Lys Leu Ile Glu Asp Val Asn Ala Ser Phe Arg Ala
            35                  40                  45

Ala Met Ala Thr Thr Ala Asn Val Pro Pro Ala Asp Lys Tyr Lys Thr
50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
                100                 105                 110

Ala Phe Val Leu His Phe Ser Glu Ala Leu Arg Ile Ile Ala Gly Thr
                115                 120                 125

Pro Glu Val His Ala Val Lys Pro Gly Ala
            130                 135
```

<210> SEQ ID NO 128
<211> LENGTH: 57
<212> TYPE: PRT
<213> ORGANISM: Phleum pratense

<400> SEQUENCE: 128

```
Ser Lys Ala Pro Gln Leu Val Pro Lys Leu Asp Glu Val Tyr Asn Ala
1               5                   10                  15

Ala Tyr Asn Ala Ala Asp His Ala Ala Pro Glu Asp Lys Tyr Glu Ala
            20                  25                  30

Phe Val Leu His Phe Ser Glu Ala Leu His Ile Ile Ala Gly Thr Pro
        35                  40                  45

Glu Val His Ala Val Lys Pro Gly Ala
    50                  55
```

<210> SEQ ID NO 129
<211> LENGTH: 80
<212> TYPE: PRT
<213> ORGANISM: Phleum pratense

<400> SEQUENCE: 129

```
Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
    50                  55                  60

His Ile Ile Ala Gly Thr Pro Glu Val His Ala Val Lys Pro Gly Ala
65                  70                  75                  80
```

<210> SEQ ID NO 130
<211> LENGTH: 106
<212> TYPE: PRT
<213> ORGANISM: Phleum pratense

<400> SEQUENCE: 130

```
Thr Glu Glu Gln Lys Leu Ile Glu Asp Val Asn Ala Ser Phe Arg Ala
1               5                   10                  15

Ala Met Ala Thr Thr Ala Asn Val Pro Pro Ala Asp Lys Tyr Lys Thr
            20                  25                  30

Leu Glu Ala Ala Phe Thr Val Ser Ser Lys Arg Asn Leu Ala Asp Ala
        35                  40                  45

Val Ser Lys Ala Pro Gln Leu Val Pro Lys Leu Asp Glu Val Tyr Asn
    50                  55                  60

Ala Ala Tyr Asn Ala Ala Asp His Ala Ala Pro Glu Asp Lys Tyr Glu
65                  70                  75                  80

Ala Phe Val Leu His Phe Ser Glu Ala Leu Arg Ile Ile Ala Gly Thr
                85                  90                  95

Pro Glu Val His Ala Val Lys Pro Gly Ala
            100                 105
```

<210> SEQ ID NO 131
<211> LENGTH: 138
<212> TYPE: PRT
<213> ORGANISM: Phleum pratense

```
<400> SEQUENCE: 131

Met Ala Ala His Lys Phe Met Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Ile Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu His Ile Ile Ala Gly Thr
        115                 120                 125

Pro Glu Val His Ala Val Lys Pro Gly Ala
    130                 135

<210> SEQ ID NO 132
<211> LENGTH: 132
<212> TYPE: PRT
<213> ORGANISM: Phleum pratense

<400> SEQUENCE: 132

Met Val Ala Met Phe Leu Ala Val Ala Val Leu Gly Leu Ala Thr
1               5                   10                  15

Ser Pro Thr Ala Glu Gly Gly Lys Ala Thr Thr Glu Glu Gln Lys Leu
            20                  25                  30

Ile Glu Asp Val Asn Ala Ser Phe Arg Ala Ala Met Ala Thr Thr Ala
        35                  40                  45

Asn Val Pro Pro Ala Asp Lys Tyr Lys Thr Phe Glu Ala Ala Phe Thr
    50                  55                  60

Val Ser Ser Lys Arg Asn Leu Ala Asp Ala Val Ser Lys Ala Pro Gln
65                  70                  75                  80

Leu Val Pro Lys Leu Asp Glu Val Tyr Asn Ala Ala Tyr Asn Ala Ala
                85                  90                  95

Asp His Ala Ala Pro Glu Asp Lys Tyr Glu Ala Phe Val Leu His Phe
            100                 105                 110

Ser Glu Ala Leu Arg Ile Ile Ala Gly Thr Pro Glu Val His Ala Val
        115                 120                 125

Lys Pro Gly Ala
    130

<210> SEQ ID NO 133
<211> LENGTH: 78
<212> TYPE: PRT
<213> ORGANISM: Phleum pratense

<400> SEQUENCE: 133

Met Ala Asp Asp Met Glu Arg Ile Phe Lys Arg Phe Asp Thr Asn Gly
1               5                   10                  15

Asp Gly Lys Ile Ser Leu Ser Glu Leu Thr Asp Ala Leu Arg Thr Leu
            20                  25                  30

Gly Ser Thr Ser Ala Asp Glu Val Gln Arg Met Met Ala Glu Ile Asp
        35                  40                  45
```

```
Thr Asp Gly Asp Gly Phe Ile Asp Phe Asn Glu Phe Ile Ser Phe Cys
     50                  55                  60

Asn Ala Asn Pro Gly Leu Met Lys Asp Val Ala Lys Val Phe
 65                  70                  75
```

<210> SEQ ID NO 134
<211> LENGTH: 131
<212> TYPE: PRT
<213> ORGANISM: Phleum pratense

<400> SEQUENCE: 134

```
Met Ser Trp Gln Thr Tyr Val Asp Glu His Leu Met Cys Glu Ile Glu
 1               5                  10                  15

Gly His His Leu Ala Ser Ala Ala Ile Leu Gly His Asp Gly Thr Val
                20                  25                  30

Trp Ala Gln Ser Ala Asp Phe Pro Gln Phe Lys Pro Glu Glu Ile Thr
             35                  40                  45

Gly Ile Met Lys Asp Phe Asp Glu Pro Gly His Leu Ala Pro Thr Gly
 50                  55                  60

Met Phe Val Ala Gly Ala Lys Tyr Met Val Ile Gln Gly Glu Pro Gly
 65                  70                  75                  80

Arg Val Ile Arg Gly Lys Lys Gly Ala Gly Ile Thr Ile Lys Lys
                 85                  90                  95

Thr Gly Gln Ala Leu Val Val Gly Ile Tyr Asp Glu Pro Met Thr Pro
                100                 105                 110

Gly Gln Cys Asn Met Val Val Glu Arg Leu Gly Asp Tyr Leu Val Glu
             115                 120                 125

Gln Gly Met
        130
```

<210> SEQ ID NO 135
<211> LENGTH: 227
<212> TYPE: PRT
<213> ORGANISM: Vespula vulgaris

<400> SEQUENCE: 135

```
Met Glu Ile Ser Gly Leu Val Tyr Leu Ile Ile Val Thr Ile Ile
 1               5                  10                  15

Asp Leu Pro Tyr Gly Lys Ala Asn Asn Tyr Cys Lys Ile Lys Cys Leu
                20                  25                  30

Lys Gly Gly Val His Thr Ala Cys Lys Tyr Gly Ser Leu Lys Pro Asn
             35                  40                  45

Cys Gly Asn Lys Val Val Val Ser Tyr Gly Leu Thr Lys Gln Glu Lys
 50                  55                  60

Gln Asp Ile Leu Lys Glu His Asn Asp Phe Arg Gln Lys Ile Ala Arg
 65                  70                  75                  80

Gly Leu Glu Thr Arg Gly Asn Pro Gly Pro Gln Pro Pro Ala Lys Asn
                 85                  90                  95

Met Lys Asn Leu Val Trp Asn Asp Glu Leu Ala Tyr Val Ala Gln Val
                100                 105                 110

Trp Ala Asn Gln Cys Gln Tyr Gly His Asp Thr Cys Arg Asp Val Ala
             115                 120                 125

Lys Tyr Gln Val Gly Gln Asn Val Ala Leu Thr Gly Ser Thr Ala Ala
             130                 135                 140

Lys Tyr Asp Asp Pro Val Lys Leu Val Lys Met Trp Glu Asp Glu Val
 145                 150                 155                 160
```

```
Lys Asp Tyr Asn Pro Lys Lys Phe Ser Gly Asn Asp Phe Leu Lys
                165                 170                 175

Thr Gly His Tyr Thr Gln Met Val Trp Ala Asn Thr Lys Glu Val Gly
            180                 185                 190

Cys Gly Ser Ile Lys Tyr Ile Gln Glu Lys Trp His Lys His Tyr Leu
            195                 200                 205

Val Cys Asn Tyr Gly Pro Ser Gly Asn Phe Met Asn Glu Glu Leu Tyr
210                 215                 220

Gln Thr Lys
225

<210> SEQ ID NO 136
<211> LENGTH: 300
<212> TYPE: PRT
<213> ORGANISM: Vespula maculifrons

<400> SEQUENCE: 136

Gly Pro Lys Cys Pro Phe Asn Ser Asp Thr Val Ser Ile Ile Ile Glu
1               5                   10                  15

Thr Arg Glu Asn Arg Asn Arg Asp Leu Tyr Thr Leu Gln Thr Leu Gln
            20                  25                  30

Asn His Pro Glu Phe Lys Lys Lys Thr Ile Thr Arg Pro Val Val Phe
        35                  40                  45

Ile Thr His Gly Phe Thr Ser Ser Ala Ser Glu Lys Asn Phe Ile Asn
50                  55                  60

Leu Ala Lys Ala Leu Val Asp Lys Asp Asn Tyr Met Val Ile Ser Ile
65                  70                  75                  80

Asp Trp Gln Thr Ala Ala Cys Thr Asn Glu Tyr Pro Gly Leu Lys Tyr
                85                  90                  95

Ala Tyr Tyr Pro Thr Ala Ala Ser Asn Thr Arg Leu Val Gly Gln Tyr
            100                 105                 110

Ile Ala Thr Ile Thr Gln Lys Leu Val Lys Asp Tyr Lys Ile Ser Met
        115                 120                 125

Ala Asn Ile Arg Leu Ile Gly His Ser Leu Gly Ala His Val Ser Gly
130                 135                 140

Phe Ala Gly Lys Arg Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
                165                 170                 175

Ser Glu Arg Leu Cys Glu Thr Asp Ala Glu Tyr Val Gln Ile Ile His
            180                 185                 190

Thr Ser Asn Tyr Leu Gly Thr Glu Lys Ile Leu Gly Thr Val Asp Phe
        195                 200                 205

Tyr Met Asn Asn Gly Lys Asn Asn Pro Gly Cys Gly Arg Phe Phe Ser
210                 215                 220

Glu Val Cys Ser His Thr Arg Ala Val Ile Tyr Met Ala Glu Cys Ile
225                 230                 235                 240

Lys His Glu Cys Cys Leu Ile Gly Ile Pro Arg Ser Lys Ser Ser Gln
                245                 250                 255

Pro Ile Ser Arg Cys Thr Lys Gln Glu Cys Val Cys Val Gly Leu Asn
            260                 265                 270

Ala Lys Lys Tyr Pro Ser Arg Gly Ser Phe Tyr Val Pro Val Glu Ser
        275                 280                 285

Thr Ala Pro Phe Cys Asn Asn Lys Gly Lys Ile Ile
        290                 295                 300
```

<210> SEQ ID NO 137
<211> LENGTH: 336
<212> TYPE: PRT
<213> ORGANISM: Vespula vulgaris

<400> SEQUENCE: 137

```
Met Glu Glu Asn Met Asn Leu Lys Tyr Leu Leu Phe Val Tyr Phe
1               5                   10                  15

Val Gln Val Leu Asn Cys Cys Tyr Gly His Gly Asp Pro Leu Ser Tyr
            20                  25                  30

Glu Leu Asp Arg Gly Pro Lys Cys Pro Phe Asn Ser Asp Thr Val Ser
        35                  40                  45

Ile Ile Ile Glu Thr Arg Glu Asn Arg Asn Asp Leu Tyr Thr Leu
    50                  55                  60

Gln Thr Leu Gln Asn His Pro Glu Phe Lys Lys Thr Ile Thr Arg
65              70                  75                  80

Pro Val Val Phe Ile Thr His Gly Phe Thr Ser Ser Ala Ser Glu Thr
                85                  90                  95

Asn Phe Ile Asn Leu Ala Lys Ala Leu Val Asp Lys Asp Asn Tyr Met
        100                 105                 110

Val Ile Ser Ile Asp Trp Gln Thr Ala Ala Cys Thr Asn Glu Ala Ala
    115                 120                 125

Gly Leu Lys Tyr Leu Tyr Tyr Pro Thr Ala Ala Arg Asn Thr Arg Leu
130                 135                 140

Val Gly Gln Tyr Ile Ala Thr Ile Thr Gln Lys Leu Val Lys His Tyr
145                 150                 155                 160

Lys Ile Ser Met Ala Asn Ile Arg Leu Ile Gly His Ser Leu Gly Ala
                165                 170                 175

His Ala Ser Gly Phe Ala Gly Lys Lys Val Gln Glu Leu Lys Leu Gly
            180                 185                 190

Lys Tyr Ser Glu Ile Ile Gly Leu Asp Pro Ala Arg Pro Ser Phe Asp
        195                 200                 205

Ser Asn His Cys Ser Glu Arg Leu Cys Glu Thr Asp Ala Glu Tyr Val
    210                 215                 220

Gln Ile Ile His Thr Ser Asn Tyr Leu Gly Thr Glu Lys Thr Leu Gly
225                 230                 235                 240

Thr Val Asp Phe Tyr Met Asn Asn Gly Lys Asn Gln Pro Gly Cys Gly
                245                 250                 255

Arg Phe Phe Ser Glu Val Cys Ser His Ser Arg Ala Val Ile Tyr Met
            260                 265                 270

Ala Glu Cys Ile Lys His Glu Cys Cys Leu Ile Gly Ile Pro Lys Ser
        275                 280                 285

Lys Ser Ser Gln Pro Ile Ser Ser Cys Thr Lys Gln Glu Cys Val Cys
    290                 295                 300

Val Gly Leu Asn Ala Lys Lys Tyr Pro Ser Arg Gly Ser Phe Tyr Val
305                 310                 315                 320

Pro Val Glu Ser Thr Ala Pro Phe Cys Asn Asn Lys Gly Lys Ile Ile
                325                 330                 335
```

<210> SEQ ID NO 138
<211> LENGTH: 331
<212> TYPE: PRT
<213> ORGANISM: Vespula vulgaris

<400> SEQUENCE: 138

Ser Glu Arg Pro Lys Arg Val Phe Asn Ile Tyr Trp Asn Val Pro Thr

```
                1               5                   10                  15
            Phe Met Cys His Gln Tyr Asp Leu Tyr Phe Asp Glu Val Thr Asn Phe
                            20                  25                  30

Asn Ile Lys Arg Asn Ser Lys Asp Asp Phe Gln Gly Asp Lys Ile Ala
                            35                  40                  45

Ile Phe Tyr Asp Pro Gly Glu Phe Pro Ala Leu Leu Ser Leu Lys Asp
                            50                  55                  60

Gly Lys Tyr Lys Lys Arg Asn Gly Gly Val Pro Gln Glu Gly Asn Ile
            65                      70                  75                  80

Thr Ile His Leu Gln Lys Phe Ile Glu Asn Leu Asp Lys Ile Tyr Pro
                            85                  90                  95

Asn Arg Asn Phe Ser Gly Ile Gly Val Ile Asp Phe Glu Arg Trp Arg
                            100                 105                 110

Pro Ile Phe Arg Gln Asn Trp Gly Asn Met Lys Ile His Lys Asn Phe
                            115                 120                 125

Ser Ile Asp Leu Val Arg Asn Glu His Pro Thr Trp Asn Lys Lys Met
                            130                 135                 140

Ile Glu Leu Glu Ala Ser Lys Arg Phe Glu Lys Tyr Ala Arg Phe Phe
            145                 150                 155                 160

Met Glu Glu Thr Leu Lys Leu Ala Lys Lys Thr Arg Lys Gln Ala Asp
                            165                 170                 175

Trp Gly Tyr Tyr Gly Tyr Pro Tyr Cys Phe Asn Met Ser Pro Asn Asn
                            180                 185                 190

Leu Val Pro Glu Cys Asp Val Thr Ala Met His Glu Asn Asp Lys Met
                            195                 200                 205

Ser Trp Leu Phe Asn Asn Gln Asn Val Leu Leu Pro Ser Val Tyr Val
                            210                 215                 220

Arg Gln Glu Leu Thr Pro Asp Gln Arg Ile Gly Leu Val Gln Gly Arg
            225                 230                 235                 240

Val Lys Glu Ala Val Arg Ile Ser Asn Asn Leu Lys His Ser Pro Lys
                            245                 250                 255

Val Leu Ser Tyr Trp Trp Tyr Val Tyr Gln Asp Glu Thr Asn Thr Phe
                            260                 265                 270

Leu Thr Glu Thr Asp Val Lys Lys Thr Phe Gln Glu Ile Val Ile Asn
                            275                 280                 285

Gly Gly Asp Gly Ile Ile Ile Trp Gly Ser Ser Ser Asp Val Asn Ser
                            290                 295                 300

Leu Ser Lys Cys Lys Arg Leu Gln Asp Tyr Leu Leu Thr Val Leu Gly
            305                 310                 315                 320

Pro Ile Ala Ile Asn Val Thr Glu Ala Val Asn
                            325                 330

<210> SEQ ID NO 139
<211> LENGTH: 206
<212> TYPE: PRT
<213> ORGANISM: Vespula vidua

<400> SEQUENCE: 139

Lys Val Asn Tyr Cys Lys Ile Lys Cys Leu Lys Gly Gly Val His Thr
            1               5                   10                  15

Ala Cys Lys Tyr Gly Thr Ser Thr Lys Pro Asn Cys Gly Lys Met Val
                            20                  25                  30

Val Lys Ala Tyr Gly Leu Thr Glu Ala Glu Lys Gln Glu Ile Leu Lys
                            35                  40                  45

Val His Asn Asp Phe Arg Gln Lys Val Ala Lys Gly Leu Glu Thr Arg
```

```
                  50                  55                  60
Gly Asn Pro Gly Pro Gln Pro Ala Lys Asn Met Asn Asn Leu Val
 65                  70                  75                  80

Trp Asn Asp Glu Leu Ala Asn Ile Ala Gln Val Trp Ala Ser Gln Cys
                 85                  90                  95

Asn Tyr Gly His Asp Thr Cys Lys Asp Thr Glu Lys Tyr Pro Val Gly
                100                 105                 110

Gln Asn Ile Ala Lys Arg Ser Thr Thr Ala Ala Leu Phe Asp Ser Pro
                115                 120                 125

Gly Lys Leu Val Lys Met Trp Glu Asn Glu Val Lys Asp Phe Asn Pro
130                 135                 140

Asn Ile Glu Trp Ser Lys Asn Leu Lys Lys Thr Gly His Tyr Thr
145                 150                 155                 160

Gln Met Val Trp Ala Lys Thr Lys Glu Ile Gly Cys Gly Ser Val Lys
                165                 170                 175

Tyr Val Lys Asp Glu Trp Tyr Thr His Tyr Leu Val Cys Asn Tyr Gly
                180                 185                 190

Pro Ser Gly Asn Phe Arg Asn Glu Lys Leu Tyr Glu Lys Lys
                195                 200                 205

<210> SEQ ID NO 140
<211> LENGTH: 160
<212> TYPE: PRT
<213> ORGANISM: Betula pendula

<400> SEQUENCE: 140

Met Gly Val Phe Asn Tyr Glu Thr Glu Thr Thr Ser Val Ile Pro Ala
  1               5                  10                  15

Ala Arg Leu Phe Lys Ala Phe Ile Leu Asp Gly Asp Asn Leu Phe Pro
                 20                  25                  30

Lys Val Ala Pro Gln Ala Ile Ser Ser Val Glu Asn Ile Glu Gly Asn
                 35                  40                  45

Gly Gly Pro Gly Thr Ile Lys Lys Ile Ser Phe Pro Glu Gly Phe Pro
 50                  55                  60

Phe Lys Tyr Val Lys Asp Arg Val Asp Glu Val Asp His Thr Asn Phe
 65                  70                  75                  80

Lys Tyr Asn Tyr Ser Val Ile Glu Gly Gly Pro Ile Gly Asp Thr Leu
                 85                  90                  95

Glu Lys Ile Ser Asn Glu Ile Lys Ile Val Ala Thr Pro Asp Gly Gly
                100                 105                 110

Ser Ile Leu Lys Ile Ser Asn Lys Tyr His Thr Lys Gly Asp His Glu
                115                 120                 125

Val Lys Ala Glu Gln Val Lys Ala Ser Lys Glu Met Gly Glu Thr Leu
                130                 135                 140

Leu Arg Ala Val Glu Ser Tyr Leu Leu Ala His Ser Asp Ala Tyr Asn
145                 150                 155                 160

<210> SEQ ID NO 141
<211> LENGTH: 133
<212> TYPE: PRT
<213> ORGANISM: Betula pendula

<400> SEQUENCE: 141

Met Ser Trp Gln Thr Tyr Val Asp Glu His Leu Met Cys Asp Ile Asp
  1               5                  10                  15

Gly Gln Ala Ser Asn Ser Leu Ala Ser Ala Ile Val Gly His Asp Gly
                 20                  25                  30
```

Ser Val Trp Ala Gln Ser Ser Phe Pro Gln Phe Lys Pro Gln Glu
                35                  40                  45

Ile Thr Gly Ile Met Lys Asp Phe Glu Glu Pro Gly His Leu Ala Pro
 50                  55                  60

Thr Gly Leu His Leu Gly Gly Ile Lys Tyr Met Val Ile Gln Gly Glu
 65                  70                  75                  80

Ala Gly Ala Val Ile Arg Gly Lys Gly Ser Gly Gly Ile Thr Ile
                85                  90                  95

Lys Lys Thr Gly Gln Ala Leu Val Phe Gly Ile Tyr Glu Glu Pro Val
                100                 105                 110

Thr Pro Gly Gln Cys Asn Met Val Val Glu Arg Leu Gly Asp Tyr Leu
                115                 120                 125

Ile Asp Gln Gly Leu
    130

<210> SEQ ID NO 142
<211> LENGTH: 205
<212> TYPE: PRT
<213> ORGANISM: Betula pendula

<400> SEQUENCE: 142

Met Pro Cys Ser Thr Glu Ala Met Glu Lys Ala Gly His Gly His Ala
1               5                   10                  15

Ser Thr Pro Arg Lys Arg Ser Leu Ser Asn Ser Ser Phe Arg Leu Arg
                20                  25                  30

Ser Glu Ser Leu Asn Thr Leu Arg Leu Arg Arg Ile Phe Asp Leu Phe
                35                  40                  45

Asp Lys Asn Ser Asp Gly Ile Ile Thr Val Asp Glu Leu Ser Arg Ala
 50                  55                  60

Leu Asn Leu Leu Gly Leu Glu Thr Asp Leu Ser Glu Leu Glu Ser Thr
 65                  70                  75                  80

Val Lys Ser Phe Thr Arg Glu Gly Asn Ile Gly Leu Gln Phe Glu Asp
                85                  90                  95

Phe Ile Ser Leu His Gln Ser Leu Asn Asp Ser Tyr Phe Ala Tyr Gly
                100                 105                 110

Gly Glu Asp Glu Asp Asp Asn Glu Glu Asp Met Arg Lys Ser Ile Leu
                115                 120                 125

Ser Gln Glu Glu Ala Asp Ser Phe Gly Gly Phe Lys Val Phe Asp Glu
130                 135                 140

Asp Gly Asp Gly Tyr Ile Ser Ala Arg Glu Leu Gln Met Val Leu Gly
145                 150                 155                 160

Lys Leu Gly Phe Ser Glu Gly Ser Glu Ile Asp Arg Val Glu Lys Met
                165                 170                 175

Ile Val Ser Val Asp Ser Asn Arg Asp Gly Arg Val Asp Phe Phe Glu
                180                 185                 190

Phe Lys Asp Met Met Arg Ser Val Leu Val Arg Ser Ser
                195                 200                 205

<210> SEQ ID NO 143
<211> LENGTH: 85
<212> TYPE: PRT
<213> ORGANISM: Betula pendula

<400> SEQUENCE: 143

Met Ala Asp Asp His Pro Gln Asp Lys Ala Glu Arg Glu Arg Ile Phe
1 5 10 15

Lys Arg Phe Asp Ala Asn Gly Asp Gly Lys Ile Ser Ala Ala Glu Leu
            20                  25                  30

Gly Glu Ala Leu Lys Thr Leu Gly Ser Ile Thr Pro Asp Glu Val Lys
        35                  40                  45

His Met Met Ala Glu Ile Asp Thr Asp Gly Asp Gly Phe Ile Ser Phe
50                  55                  60

Gln Glu Phe Thr Asp Phe Gly Arg Ala Asn Arg Gly Leu Leu Lys Asp
65                  70                  75                  80

Val Ala Lys Ile Phe
                85

<210> SEQ ID NO 144
<211> LENGTH: 24
<212> TYPE: PRT
<213> ORGANISM: Quercus alba
<220> FEATURE:
<221> NAME/KEY: UNSURE
<222> LOCATION: (5)..(5)
<223> OTHER INFORMATION: Xaa = unknown
<220> FEATURE:
<221> NAME/KEY: UNSURE
<222> LOCATION: (17)..(17)
<223> OTHER INFORMATION: Xaa = unknown

<400> SEQUENCE: 144

Gly Val Phe Thr Xaa Glu Ser Gln Glu Thr Ser Val Ile Ala Pro Ala
1               5                   10                  15

Xaa Leu Phe Lys Ala Leu Phe Leu
            20

<210> SEQ ID NO 145
<211> LENGTH: 40
<212> TYPE: PRT
<213> ORGANISM: Carpinus betulus
<220> FEATURE:
<221> NAME/KEY: UNSURE
<222> LOCATION: (39)..(39)
<223> OTHER INFORMATION: Xaa = unknown

<400> SEQUENCE: 145

Gly Val Phe Asn Tyr Glu Ala Glu Thr Pro Ser Val Ile Pro Ala Ala
1               5                   10                  15

Arg Leu Phe Lys Ser Tyr Val Leu Asp Gly Asp Lys Leu Ile Pro Lys
            20                  25                  30

Val Ala Pro Gln Ala Ile Xaa Lys
        35                  40

<210> SEQ ID NO 146
<211> LENGTH: 44
<212> TYPE: PRT
<213> ORGANISM: Alnus glutinosa

<400> SEQUENCE: 146

Gly Val Phe Asn Tyr Glu Ala Glu Thr Pro Ser Val Ile Pro Ala Ala
1               5                   10                  15

Arg Leu Phe Lys Ala Phe Ile Leu Asp Gly Asp Lys Leu Leu Pro Lys
            20                  25                  30

Val Ala Pro Glu Ala Val Ser Ser Val Glu Asn Ile
        35                  40

<210> SEQ ID NO 147
<211> LENGTH: 110
<212> TYPE: PRT
<213> ORGANISM: Betula pendula -continued

<400> SEQUENCE: 147

Val Gln Cys Met Gln Val Trp Pro Pro Leu Gly Leu Lys Lys Phe Glu
1               5                   10                  15

Thr Leu Ser Tyr Leu Pro Pro Leu Ser Ser Glu Gln Leu Ala Lys Glu
            20                  25                  30

Val Asp Tyr Leu Leu Arg Lys Asn Leu Ile Pro Cys Leu Glu Phe Glu
        35                  40                  45

Leu Glu His Gly Phe Val Tyr Arg Glu His Asn Arg Ser Pro Gly Tyr
    50                  55                  60

Tyr Asp Gly Arg Tyr Trp Thr Met Trp Lys Leu Pro Met Phe Gly Cys
65                  70                  75                  80

Asn Asp Ser Ser Gln Val Leu Lys Glu Leu Glu Glu Cys Lys Lys Ala
                85                  90                  95

Tyr Pro Ser Ala Phe Ile Arg Ile Ile Gly Phe Asp Asp Lys
            100                 105                 110

<210> SEQ ID NO 148
<211> LENGTH: 626
<212> TYPE: PRT
<213> ORGANISM: Arachis hypogaea

<400> SEQUENCE: 148

Met Arg Gly Arg Val Ser Pro Leu Met Leu Leu Gly Ile Leu Val
1               5                   10                  15

Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
        35                  40                  45

Glu Pro Asp Asp Leu Lys Gln Lys Ala Cys Glu Ser Arg Cys Thr Lys
    50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
    130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Gln Glu Glu Arg Gly Gln Arg Arg
            340                 345                 350

Trp Ser Thr Arg Ser Ser Glu Asn Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
        435                 440                 445

Asn Ser Lys Ala Met Val Ile Val Val Asn Lys Gly Thr Gly Asn
    450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Gly Ser Asn Arg Glu
                485                 490                 495

Val Arg Arg Tyr Thr Ala Arg Leu Lys Glu Gly Asp Val Phe Ile Met
            500                 505                 510

Pro Ala Ala His Pro Val Ala Ile Asn Ala Ser Ser Glu Leu His Leu
        515                 520                 525

Leu Gly Phe Gly Ile Asn Ala Glu Asn Asn His Arg Ile Phe Leu Ala
    530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Lys Glu Asp Gln Glu
        595                 600                 605

Glu Glu Asn Gln Gly Gly Lys Gly Pro Leu Leu Ser Ile Leu Lys Ala
    610                 615                 620

Phe Asn
625

<210> SEQ ID NO 149
<211> LENGTH: 392
<212> TYPE: PRT
<213> ORGANISM: Ambrosia artemisiifolia

<400> SEQUENCE: 149

```
Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Gln Ile
            20                  25                  30

Leu Pro Ser Ala Asn Glu Thr Arg Ser Leu Thr Thr Cys Gly Thr Tyr
            35                  40                  45

Asn Ile Ile Asp Gly Cys Trp Arg Gly Lys Ala Asp Trp Ala Glu Asn
        50                  55                  60

Arg Lys Ala Leu Ala Asp Cys Ala Gln Gly Phe Ala Lys Gly Thr Ile
65                  70                  75                  80

Gly Gly Lys Asp Gly Asp Ile Tyr Thr Val Thr Ser Glu Leu Asp Asp
                85                  90                  95

Asp Val Ala Asn Pro Lys Glu Gly Thr Leu Arg Phe Gly Ala Ala Gln
                100                 105                 110

Asn Arg Pro Leu Trp Ile Ile Phe Ala Arg Asp Met Val Ile Arg Leu
            115                 120                 125

Asp Arg Glu Leu Ala Ile Asn Asn Asp Lys Thr Ile Asp Gly Arg Gly
        130                 135                 140

Ala Lys Val Glu Ile Ile Asn Ala Gly Phe Ala Ile Tyr Asn Val Lys
145                 150                 155                 160

Asn Ile Ile Ile His Asn Ile Ile Met His Asp Ile Val Val Asn Pro
                165                 170                 175

Gly Gly Leu Ile Lys Ser His Asp Gly Pro Pro Val Pro Arg Lys Gly
            180                 185                 190

Ser Asp Gly Asp Ala Ile Gly Ile Ser Gly Ser Gln Ile Trp Ile
            195                 200                 205

Asp His Cys Ser Leu Ser Lys Ala Val Asp Gly Leu Ile Asp Ala Lys
        210                 215                 220

His Gly Ser Thr His Phe Thr Val Ser Asn Cys Leu Phe Thr Gln His
225                 230                 235                 240

Gln Tyr Leu Leu Phe Trp Asp Phe Asp Glu Arg Gly Met Leu Cys
                245                 250                 255

Thr Val Ala Phe Asn Lys Phe Thr Asp Asn Val Asp Gln Arg Met Pro
                260                 265                 270

Asn Leu Arg His Gly Phe Val Gln Val Val Asn Asn Tyr Glu Arg
            275                 280                 285

Trp Gly Ser Tyr Ala Leu Gly Gly Ser Ala Gly Pro Thr Ile Leu Ser
        290                 295                 300

Gln Gly Asn Arg Phe Leu Ala Ser Asp Ile Lys Lys Glu Val Val Gly
305                 310                 315                 320

Arg Tyr Gly Glu Ser Ala Met Ser Glu Ser Ile Asn Trp Asn Trp Arg
                325                 330                 335

Ser Tyr Met Asp Val Phe Glu Asn Gly Ala Ile Phe Val Pro Ser Gly
            340                 345                 350

Val Asp Pro Val Leu Thr Pro Glu Gln Asn Ala Gly Met Ile Pro Ala
        355                 360                 365

Glu Pro Gly Glu Ala Val Leu Arg Leu Thr Ser Ser Ala Gly Val Leu
            370                 375                 380

Ser Cys Gln Pro Gly Ala Pro Cys
385                 390

<210> SEQ ID NO 150
<211> LENGTH: 397
<212> TYPE: PRT
<213> ORGANISM: Ambrosia artemisiifolia
```

<400> SEQUENCE: 150

```
Met Gly Ile Lys His Cys Cys Tyr Ile Leu Tyr Phe Thr Leu Ala Leu
1               5                   10                  15

Val Thr Leu Val Gln Ala Gly Arg Leu Gly Glu Glu Val Asp Ile Leu
            20                  25                  30

Pro Ser Pro Asn Asp Thr Arg Arg Ser Leu Gln Gly Cys Glu Ala His
        35                  40                  45

Asn Ile Ile Asp Lys Cys Trp Arg Cys Lys Pro Asp Trp Ala Glu Asn
    50                  55                  60

Arg Gln Ala Leu Gly Asn Cys Ala Gln Gly Phe Gly Lys Ala Thr His
65                  70                  75                  80

Gly Gly Lys Trp Gly Asp Ile Tyr Met Val Thr Ser Asp Gln Asp Asp
                85                  90                  95

Asp Val Val Asn Pro Lys Glu Gly Thr Leu Arg Phe Gly Ala Thr Gln
            100                 105                 110

Asp Arg Pro Leu Trp Ile Ile Phe Gln Arg Asp Met Ile Ile Tyr Leu
        115                 120                 125

Gln Gln Glu Met Val Val Thr Ser Asp Lys Thr Ile Asp Gly Arg Gly
130                 135                 140

Ala Lys Val Glu Leu Val Tyr Gly Gly Ile Thr Leu Met Asn Val Lys
145                 150                 155                 160

Asn Val Ile Ile His Asn Ile Asp Ile His Asp Val Arg Val Leu Pro
                165                 170                 175

Gly Gly Arg Ile Lys Ser Asn Gly Gly Pro Ala Ile Pro Arg His Gln
            180                 185                 190

Ser Asp Gly Asp Ala Ile His Val Thr Gly Ser Ser Asp Ile Trp Ile
        195                 200                 205

Asp His Cys Thr Leu Ser Lys Ser Phe Asp Gly Leu Val Asp Val Asn
    210                 215                 220

Trp Gly Ser Thr Gly Val Thr Ile Ser Asn Cys Lys Phe Thr His His
225                 230                 235                 240

Glu Lys Ala Val Leu Leu Gly Ala Ser Asp Thr His Phe Gln Asp Leu
                245                 250                 255

Lys Met His Val Thr Leu Ala Tyr Asn Ile Phe Thr Asn Thr Val His
            260                 265                 270

Glu Arg Met Pro Arg Cys Arg Phe Gly Phe Phe Gln Ile Val Asn Asn
        275                 280                 285

Phe Tyr Asp Arg Trp Asp Lys Tyr Ala Ile Gly Gly Ser Ser Asn Pro
    290                 295                 300

Thr Ile Leu Ser Gln Gly Asn Lys Phe Val Ala Pro Asp Phe Ile Tyr
305                 310                 315                 320

Lys Lys Asn Val Cys Leu Arg Thr Gly Ala Gln Glu Pro Glu Trp Met
                325                 330                 335

Thr Trp Asn Trp Arg Thr Gln Asn Asp Val Leu Glu Asn Gly Ala Ile
            340                 345                 350

Phe Val Ala Ser Gly Ser Asp Pro Val Leu Thr Ala Glu Gln Asn Ala
        355                 360                 365

Gly Met Met Gln Ala Glu Pro Gly Asp Met Val Pro Gln Leu Thr Met
    370                 375                 380

Asn Ala Gly Val Leu Thr Cys Ser Pro Gly Ala Pro Cys
385                 390                 395
```

<210> SEQ ID NO 151

```
<211> LENGTH: 397
<212> TYPE: PRT
<213> ORGANISM: Ambrosia artemisiifolia

<400> SEQUENCE: 151

Met Gly Ile Lys Gln Cys Cys Tyr Ile Leu Tyr Phe Thr Leu Ala Leu
1               5                   10                  15

Val Ala Leu Leu Gln Pro Val Arg Ser Ala Glu Gly Val Gly Glu Ile
            20                  25                  30

Leu Pro Ser Val Asn Glu Thr Arg Ser Leu Gln Ala Cys Glu Ala Leu
        35                  40                  45

Asn Ile Ile Asp Lys Cys Trp Arg Gly Lys Ala Asp Trp Glu Asn Asn
    50                  55                  60

Arg Gln Ala Leu Ala Asp Cys Ala Gln Gly Phe Ala Lys Gly Thr Tyr
65                  70                  75                  80

Gly Gly Lys Trp Gly Asp Val Tyr Thr Val Thr Ser Asn Leu Asp Asp
                85                  90                  95

Asp Val Ala Asn Pro Lys Glu Gly Thr Leu Arg Phe Ala Ala Ala Gln
            100                 105                 110

Asn Arg Pro Leu Trp Ile Ile Phe Lys Asn Asp Met Val Ile Asn Leu
        115                 120                 125

Asn Gln Glu Leu Val Val Asn Ser Asp Lys Thr Ile Asp Gly Arg Gly
    130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
                165                 170                 175

Gly Gly Met Ile Lys Ser Asn Asp Gly Pro Pro Ile Leu Arg Gln Ala
            180                 185                 190

Ser Asp Gly Asp Thr Ile Asn Val Ala Gly Ser Ser Gln Ile Trp Ile
        195                 200                 205

Asp His Cys Ser Leu Ser Lys Ser Phe Asp Gly Leu Val Asp Val Thr
    210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
                245                 250                 255

Gly Met Leu Ala Thr Val Ala Phe Asn Met Phe Thr Asp Asn Val Asp
            260                 265                 270

Gln Arg Met Pro Arg Cys Arg Phe Gly Phe Gln Val Val Asn Asn
        275                 280                 285

Asn Tyr Asp Arg Trp Gly Thr Tyr Ala Ile Gly Gly Ser Ser Ala Pro
    290                 295                 300

Thr Ile Leu Cys Gln Gly Asn Arg Phe Leu Ala Pro Asp Asp Gln Ile
305                 310                 315                 320

Lys Lys Asn Val Leu Ala Arg Thr Gly Thr Gly Ala Ala Glu Ser Met
                325                 330                 335

Ala Trp Asn Trp Arg Ser Asp Lys Asp Leu Leu Glu Asn Gly Ala Ile
            340                 345                 350

Phe Val Thr Ser Gly Ser Asp Pro Val Leu Thr Pro Val Gln Ser Ala
        355                 360                 365

Gly Met Ile Pro Ala Glu Pro Gly Glu Ala Ile Lys Leu Thr Ser
    370                 375                 380

Ser Ala Gly Val Phe Ser Cys His Pro Gly Ala Pro Cys
385                 390                 395
```

<210> SEQ ID NO 152
<211> LENGTH: 398
<212> TYPE: PRT
<213> ORGANISM: Ambrosia artemisiifolia

<400> SEQUENCE: 152

```
Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Val Glu Glu Phe
            20                  25                  30

Leu Pro Ser Ala Asn Glu Thr Arg Arg Ser Leu Lys Ala Cys Glu Ala
        35                  40                  45

His Asn Ile Ile Asp Lys Cys Trp Arg Cys Lys Ala Asp Trp Ala Asn
    50                  55                  60

Asn Arg Gln Ala Leu Ala Asp Cys Ala Gln Gly Phe Ala Lys Gly Thr
65                  70                  75                  80

Tyr Gly Gly Lys His Gly Asp Val Tyr Thr Val Thr Ser Asp Lys Asp
                85                  90                  95

Asp Asp Val Ala Asn Pro Lys Glu Gly Thr Leu Arg Phe Ala Ala Ala
            100                 105                 110

Gln Asn Arg Pro Leu Trp Ile Ile Phe Lys Arg Asn Met Val Ile His
        115                 120                 125

Leu Asn Gln Glu Leu Val Val Asn Ser Asp Lys Thr Ile Asp Gly Arg
    130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
            180                 185                 190

Gln Ser Asp Gly Asp Ala Ile Asn Val Ala Gly Ser Ser Gln Ile Trp
        195                 200                 205

Ile Asp His Cys Ser Leu Ser Lys Ala Ser Asp Gly Leu Leu Asp Ile
    210                 215                 220

Thr Leu Gly Ser Ser His Val Thr Val Ser Asn Cys Lys Phe Thr Gln
225                 230                 235                 240

His Gln Phe Val Leu Leu Gly Ala Asp Asp Thr His Tyr Gln Asp
                245                 250                 255

Lys Gly Met Leu Ala Thr Val Ala Phe Asn Met Phe Thr Asp His Val
            260                 265                 270

Asp Gln Arg Met Pro Arg Cys Arg Phe Gly Phe Phe Gln Val Val Asn
        275                 280                 285

Asn Asn Tyr Asp Arg Trp Gly Thr Tyr Ala Ile Gly Gly Ser Ser Ala
    290                 295                 300

Pro Thr Ile Leu Ser Gln Gly Asn Arg Phe Phe Ala Pro Asp Asp Ile
305                 310                 315                 320

Ile Lys Lys Asn Val Leu Ala Arg Thr Gly Thr Gly Asn Ala Glu Ser
                325                 330                 335

Met Ser Trp Asn Trp Arg Thr Asp Arg Asp Leu Leu Glu Asn Gly Ala
            340                 345                 350

Ile Phe Leu Pro Ser Gly Ser Asp Pro Val Leu Thr Pro Glu Gln Lys
        355                 360                 365

Ala Gly Met Ile Pro Ala Glu Pro Gly Glu Ala Val Leu Arg Leu Thr
    370                 375                 380
```

```
Ser Ser Ala Gly Val Leu Ser Cys His Gln Gly Ala Pro Cys
385                 390                 395

<210> SEQ ID NO 153
<211> LENGTH: 396
<212> TYPE: PRT
<213> ORGANISM: Ambrosia artemisiifolia

<400> SEQUENCE: 153

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
                20                  25                  30

Leu Pro Val Asn Glu Thr Arg Arg Leu Thr Thr Ser Gly Ala Tyr Asn
            35                  40                  45

Ile Ile Asp Gly Cys Trp Arg Gly Lys Ala Asp Trp Ala Glu Asn Arg
        50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp Asp
                85                  90                  95

Val Ala Asn Pro Lys Glu Gly Thr Leu Arg Phe Gly Ala Ala Gln Asn
                100                 105                 110

Arg Pro Leu Trp Ile Ile Phe Glu Arg Asp Met Val Ile Arg Leu Asp
            115                 120                 125

Lys Glu Met Val Val Asn Ser Asp Lys Thr Ile Asp Gly Arg Gly Ala
        130                 135                 140

Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
                180                 185                 190

Asp Gly Asp Ala Ile Ser Ile Ser Gly Ser Ser Gln Ile Trp Ile Asp
            195                 200                 205

His Cys Ser Leu Ser Lys Ser Val Asp Gly Leu Val Asp Ala Lys Leu
        210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255

Met Leu Ala Thr Val Ala Phe Asn Thr Phe Thr Asp Asn Val Asp Gln
                260                 265                 270

Arg Met Pro Arg Cys Arg His Gly Phe Phe Gln Val Val Asn Asn Asn
            275                 280                 285

Tyr Asp Lys Trp Gly Ser Tyr Ala Ile Gly Gly Ser Ala Ser Pro Thr
        290                 295                 300

Ile Leu Ser Gln Gly Asn Arg Phe Cys Ala Pro Asp Glu Arg Ser Lys
305                 310                 315                 320

Lys Asn Val Leu Gly Arg His Gly Glu Ala Ala Ala Glu Ser Met Lys
                325                 330                 335

Trp Asn Trp Arg Thr Asn Lys Asp Val Leu Glu Asn Gly Ala Ile Phe
                340                 345                 350

Val Ala Ser Gly Val Asp Pro Val Leu Thr Pro Glu Gln Ser Ala Gly
            355                 360                 365
```

```
Met Ile Pro Ala Glu Pro Gly Glu Ser Ala Leu Ser Leu Thr Ser Ser
    370                 375                 380

Ala Gly Val Leu Ser Cys Gln Pro Gly Ala Pro Cys
385                 390                 395

<210> SEQ ID NO 154
<211> LENGTH: 373
<212> TYPE: PRT
<213> ORGANISM: Cryptomeria japonica

<400> SEQUENCE: 154

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Pro Val Asn Pro Gly Thr Leu Arg Tyr
65                  70                  75                  80

Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
            100                 105                 110

Asp Gly Arg Gly Ala Gln Val Tyr Ile Gly Asn Gly Pro Cys Val
        115                 120                 125

Phe Ile Lys Arg Val Ser Asn Val Ile His Gly Leu Tyr Leu Tyr
    130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Thr Ser Thr Gly Val Thr Ile Ser
        195                 200                 205

Asn Asn Leu Phe Phe Asn His His Lys Val Met Ser Leu Gly His Asp
    210                 215                 220

Asp Ala Tyr Ser Asp Asp Lys Ser Met Lys Val Thr Val Ala Phe Asn
225                 230                 235                 240

Gln Phe Gly Pro Asn Cys Gly Gln Arg Met Pro Arg Ala Arg Tyr Gly
                245                 250                 255

Leu Val His Val Ala Asn Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
        275                 280                 285

Thr Ala Pro Asn Glu Ser Tyr Lys Lys Gln Val Thr Ile Arg Ile Gly
    290                 295                 300

Cys Lys Thr Ser Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
                325                 330                 335

Gly Gly Asn Ile Tyr Thr Lys Lys Glu Ala Phe Asn Val Glu Asn Gly
            340                 345                 350
```

Asn Ala Thr Pro His Leu Thr Gln Asn Ala Gly Val Leu Thr Cys Ser
            355                 360                 365

Leu Ser Lys Arg Cys
    370

<210> SEQ ID NO 155
<211> LENGTH: 374
<212> TYPE: PRT
<213> ORGANISM: Cryptomeria japonica

<400> SEQUENCE: 155

Met Asp Ser Pro Cys Leu Val Ala Leu Val Leu Ser Phe Val Ile
1               5                   10                  15

Gly Ser Cys Phe Ser Asp Asn Pro Ile Asp Ser Cys Trp Arg Gly Asp
                20                  25                  30

Ser Asn Trp Ala Gln Asn Arg Met Lys Leu Ala Asp Cys Ala Val Gly
            35                  40                  45

Phe Gly Ser Ser Thr Met Gly Lys Gly Gly Asp Leu Tyr Thr Val
    50                  55                  60

Thr Asn Ser Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
                100                 105                 110

Phe Asp Gly Arg Gly Ala Gln Val Tyr Ile Gly Asn Gly Gly Pro Cys
            115                 120                 125

Val Phe Ile Lys Arg Val Ser Asn Val Ile Ile His Gly Leu His Leu
130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Ser Ser Thr Gly Val Thr Ile
        195                 200                 205

Ser Asn Asn Leu Phe Phe Asn His His Lys Val Met Leu Leu Gly His
210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Tyr Asp Pro Trp Thr Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
    290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350

```
Gly Asn Ala Thr Pro Gln Leu Thr Lys Asn Ala Gly Val Leu Thr Cys
            355                 360                 365

Ser Leu Ser Lys Arg Cys
            370

<210> SEQ ID NO 156
<211> LENGTH: 514
<212> TYPE: PRT
<213> ORGANISM: Cryptomeria japonica

<400> SEQUENCE: 156

Met Ala Met Lys Leu Ile Ala Pro Met Ala Phe Leu Ala Met Gln Leu
1               5                   10                  15

Ile Ile Met Ala Ala Ala Glu Asp Gln Ser Ala Gln Ile Met Leu Asp
            20                  25                  30

Ser Val Val Glu Lys Tyr Leu Arg Ser Asn Arg Ser Leu Arg Lys Val
            35                  40                  45

Glu His Ser Arg His Asp Ala Ile Asn Ile Phe Asn Val Glu Lys Tyr
        50                  55                  60

Gly Ala Val Gly Asp Gly Lys His Asp Cys Thr Glu Ala Phe Ser Thr
65                  70                  75                  80

Ala Trp Gln Ala Ala Cys Lys Asn Pro Ser Ala Met Leu Leu Val Pro
                85                  90                  95

Gly Ser Lys Lys Phe Val Val Asn Asn Leu Phe Phe Asn Gly Pro Cys
            100                 105                 110

Gln Pro His Phe Thr Phe Lys Val Asp Gly Ile Ile Ala Ala Tyr Gln
            115                 120                 125

Asn Pro Ala Ser Trp Lys Asn Asn Arg Ile Trp Leu Gln Phe Ala Lys
        130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
            195                 200                 205

Leu Val Phe Gly Asn Cys Glu Gly Val Lys Ile Ile Gly Ile Ser Ile
        210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
            275                 280                 285

Asn Ser Arg Ala Glu Val Ser Tyr Val His Val Asn Gly Ala Lys Phe
        290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350
```

```
Cys Gln Asn Gln Arg Ser Ala Val Gln Ile Gln Asp Val Thr Tyr Lys
            355                 360                 365

Asn Ile Arg Gly Thr Ser Ala Thr Ala Ala Ile Gln Leu Lys Cys
370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
            405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
            435                 440                 445

Met Val Glu Asn Met Arg Ala Tyr Asp Lys Gly Asn Arg Thr Arg Ile
            450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
            485                 490                 495

Glu Tyr Tyr Pro Gln Arg Trp Ile Cys Ser Cys His Gly Lys Ile Tyr
            500                 505                 510

His Pro

<210> SEQ ID NO 157
<211> LENGTH: 514
<212> TYPE: PRT
<213> ORGANISM: Cryptomeria japonica

<400> SEQUENCE: 157

Met Ala Met Lys Phe Ile Ala Pro Met Ala Phe Val Ala Met Gln Leu
1               5                   10                  15

Ile Ile Met Ala Ala Ala Glu Asp Gln Ser Ala Gln Ile Met Leu Asp
            20                  25                  30

Ser Asp Ile Glu Gln Tyr Leu Arg Ser Asn Arg Ser Leu Arg Lys Val
            35                  40                  45

Glu His Ser Arg His Asp Ala Ile Asn Ile Phe Asn Val Glu Lys Tyr
            50                  55                  60

Gly Ala Val Gly Asp Gly Lys His Asp Cys Thr Glu Ala Phe Ser Thr
65                  70                  75                  80

Ala Trp Gln Ala Ala Cys Lys Lys Pro Ser Ala Met Leu Leu Val Pro
            85                  90                  95

Gly Asn Lys Lys Phe Val Val Asn Asn Leu Phe Phe Asn Gly Pro Cys
            100                 105                 110

Gln Pro His Phe Thr Phe Lys Val Asp Gly Ile Ile Ala Ala Tyr Gln
            115                 120                 125

Asn Pro Ala Ser Trp Lys Asn Asn Arg Ile Trp Leu Gln Phe Ala Lys
            130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
            165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
            195                 200                 205
```

```
Leu Val Phe Gly Asn Cys Glu Gly Val Lys Ile Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
                260                 265                 270

Ile Cys Gly Pro Gly His Gly Ile Ser Ile Gly Ser Leu Gly Arg Glu
                275                 280                 285

Asn Ser Arg Ala Glu Val Ser Tyr Val His Val Asn Gly Ala Lys Phe
290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
                340                 345                 350

Cys Gln Asn Gln Arg Ser Ala Val Gln Ile Gln Asp Val Thr Tyr Lys
                355                 360                 365

Asn Ile Arg Gly Thr Ser Ala Thr Ala Ala Ile Gln Leu Lys Cys
370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
                420                 425                 430

Ser Ala Lys Arg Lys Glu Ser Lys Ser His Lys His Pro Lys Thr Val
                435                 440                 445

Met Val Lys Asn Met Gly Ala Tyr Asp Lys Gly Asn Arg Thr Arg Ile
450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Met Cys Ser Arg His Gly Lys Ile Tyr
                500                 505                 510

His Pro

<210> SEQ ID NO 158
<211> LENGTH: 373
<212> TYPE: PRT
<213> ORGANISM: Cryptomeria japonica

<400> SEQUENCE: 158

Met Asp Ser Pro Cys Leu Val Ala Leu Leu Val Leu Ser Phe Val Ile
1               5                   10                  15

Gly Ser Cys Phe Ser Asp Asn Pro Ile Asp Ser Cys Trp Arg Gly Asp
                20                  25                  30

Ser Asn Trp Ala Gln Asn Arg Met Lys Leu Ala Asp Cys Ala Val Gly
                35                  40                  45

Phe Gly Ser Ser Thr Met Gly Gly Lys Gly Asp Leu Tyr Thr Val
    50                  55                  60

Thr Asn Ser Asp Asp Asp Pro Val Asn Pro Pro Gly Thr Leu Arg Tyr
```

```
                65                  70                  75                  80
Gly Ala Thr Arg Asp Arg Pro Leu Trp Ile Ile Phe Ser Gly Asn Met
                    85                  90                  95
Asn Ile Lys Leu Lys Met Pro Met Tyr Ile Ala Gly Tyr Lys Thr Phe
                    100                 105                 110
Asp Gly Arg Gly Ala Gln Val Tyr Ile Gly Asn Gly Gly Pro Cys Val
                    115                 120                 125
Phe Ile Lys Arg Val Ser Asn Val Ile His Gly Leu His Leu Tyr
    130                 135                 140
Gly Cys Ser Thr Ser Val Leu Gly Asn Val Leu Ile Asn Glu Ser Phe
145                 150                 155                 160
Gly Val Glu Pro Val His Pro Gln Asp Gly Asp Ala Leu Thr Leu Arg
                    165                 170                 175
Thr Ala Thr Asn Ile Trp Ile Asp His Asn Ser Phe Ser Asn Ser Ser
                    180                 185                 190
Asp Gly Leu Val Asp Val Thr Leu Ser Ser Thr Gly Val Thr Ile Ser
                    195                 200                 205
Asn Asn Leu Phe Phe Asn His His Lys Val Met Leu Leu Gly His Asp
    210                 215                 220
Asp Ala Tyr Ser Asp Asp Lys Ser Met Lys Val Thr Val Ala Phe Asn
225                 230                 235                 240
Gln Phe Gly Pro Asn Cys Gly Gln Arg Met Pro Arg Ala Arg Tyr Gly
                    245                 250                 255
Leu Val His Val Ala Asn Asn Tyr Asp Pro Trp Thr Ile Tyr Ala
                    260                 265                 270
Ile Gly Gly Ser Ser Asn Pro Thr Ile Leu Ser Glu Gly Asn Ser Phe
                    275                 280                 285
Thr Ala Pro Asn Glu Ser Tyr Lys Lys Gln Val Thr Ile Arg Ile Gly
                    290                 295                 300
Cys Lys Thr Ser Ser Ser Cys Ser Asn Trp Val Trp Gln Ser Thr Gln
305                 310                 315                 320
Asp Val Phe Tyr Asn Gly Ala Tyr Phe Val Ser Ser Gly Lys Tyr Glu
                    325                 330                 335
Gly Gly Asn Ile Tyr Thr Lys Lys Glu Ala Phe Asn Val Glu Asn Gly
                    340                 345                 350
Asn Ala Thr Pro Gln Leu Thr Lys Asn Ala Gly Val Leu Thr Cys Ser
                    355                 360                 365
Leu Ser Lys Arg Cys
    370

<210> SEQ ID NO 159
<211> LENGTH: 374
<212> TYPE: PRT
<213> ORGANISM: Cryptomeria japonica

<400> SEQUENCE: 159

Met Asp Ser Pro Cys Leu Val Ala Leu Leu Val Phe Ser Phe Val Ile
1               5                   10                  15
Gly Ser Cys Phe Ser Asp Asn Pro Ile Asp Ser Cys Trp Arg Gly Asp
                    20                  25                  30
Ser Asn Trp Ala Gln Asn Arg Met Lys Leu Ala Asp Cys Ala Val Gly
                    35                  40                  45
Phe Gly Ser Ser Thr Met Gly Gly Lys Gly Asp Leu Tyr Thr Val
    50                  55                  60
Thr Asn Ser Asp Asp Pro Val Asn Pro Ala Pro Gly Thr Leu Arg
```

```
                65                  70                  75                  80
Tyr Gly Ala Thr Arg Asp Arg Pro Leu Trp Ile Ile Phe Ser Gly Asn
                    85                  90                  95

Met Asn Ile Lys Leu Lys Met Pro Met Tyr Ile Ala Gly Tyr Lys Thr
                    100                 105                 110

Phe Asp Gly Arg Gly Ala Gln Val Tyr Ile Gly Asn Gly Gly Pro Cys
                    115                 120                 125

Val Phe Ile Lys Arg Val Ser Asn Val Ile Ile His Gly Leu Tyr Leu
                    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                    165                 170                 175

Arg Thr Ala Thr Asn Ile Trp Ile Asp His Asn Ser Phe Ser Asn Ser
                    180                 185                 190

Ser Asp Gly Leu Val Asp Val Thr Leu Thr Ser Thr Gly Val Thr Ile
                    195                 200                 205

Ser Asn Asn Leu Phe Phe Asn His His Lys Val Met Ser Leu Gly His
                    210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                    245                 250                 255

Gly Leu Val His Val Ala Asn Asn Asn Tyr Asp Pro Trp Thr Ile Tyr
                    260                 265                 270

Ala Ile Gly Gly Ser Ser Asn Pro Thr Ile Leu Ser Glu Gly Asn Ser
                    275                 280                 285

Phe Thr Ala Pro Asn Glu Ser Tyr Lys Lys Gln Val Thr Ile Arg Ile
                    290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                    325                 330                 335

Glu Gly Gly Asn Ile Tyr Thr Lys Lys Glu Ala Phe Asn Val Glu Asn
                    340                 345                 350

Gly Asn Ala Thr Pro His Leu Thr Gln Asn Ala Gly Val Leu Thr Cys
                    355                 360                 365

Ser Leu Ser Lys Arg Cys
                    370

<210> SEQ ID NO 160
<211> LENGTH: 174
<212> TYPE: PRT
<213> ORGANISM: Canis familiaris

<400> SEQUENCE: 160

Met Lys Thr Leu Leu Leu Thr Ile Gly Phe Ser Leu Ile Ala Ile Leu
1               5                   10                  15

Gln Ala Gln Asp Thr Pro Ala Leu Gly Lys Asp Thr Val Ala Val Ser
                    20                  25                  30

Gly Lys Trp Tyr Leu Lys Ala Met Thr Ala Asp Gln Glu Val Pro Glu
                    35                  40                  45

Lys Pro Asp Ser Val Thr Pro Met Ile Leu Lys Ala Gln Lys Gly Gly
                    50                  55                  60

Asn Leu Glu Ala Lys Ile Thr Met Leu Thr Asn Gly Gln Cys Gln Asn
```

```
                65                  70                  75                  80
Ile Thr Val Val Leu His Lys Thr Ser Glu Pro Gly Lys Tyr Thr Ala
                    85                  90                  95

Tyr Glu Gly Gln Arg Val Val Phe Ile Gln Pro Ser Pro Val Arg Asp
                100                 105                 110

His Tyr Ile Leu Tyr Cys Gly Glu Leu His Gly Arg Gln Ile Arg
            115                 120                 125

Met Ala Lys Leu Leu Gly Arg Asp Pro Glu Gln Ser Gln Glu Ala Leu
        130                 135                 140

Glu Asp Phe Arg Glu Phe Ser Arg Ala Lys Gly Leu Asn Gln Glu Ile
145                 150                 155                 160

Leu Glu Leu Ala Gln Ser Glu Thr Cys Ser Pro Gly Gly Gln
                165                 170

<210> SEQ ID NO 161
<211> LENGTH: 24
<212> TYPE: PRT
<213> ORGANISM: Canis familiaris

<400> SEQUENCE: 161

Glu Ala Tyr Lys Ser Glu Ile Ala His Arg Tyr Asn Asp Leu Gly Glu
1               5                   10                  15

Glu His Phe Arg Gly Leu Val Leu
            20

<210> SEQ ID NO 162
<211> LENGTH: 265
<212> TYPE: PRT
<213> ORGANISM: Canis familiaris

<400> SEQUENCE: 162

Leu Ser Ser Ala Lys Glu Arg Phe Lys Cys Ala Ser Leu Gln Lys Phe
1               5                   10                  15

Gly Asp Arg Ala Phe Lys Ala Trp Ser Val Ala Arg Leu Ser Gln Arg
                20                  25                  30

Phe Pro Lys Ala Asp Phe Ala Glu Ile Ser Lys Val Val Thr Asp Leu
            35                  40                  45

Thr Lys Val His Lys Glu Cys Cys His Gly Asp Leu Leu Glu Cys Ala
        50                  55                  60

Asp Asp Arg Ala Asp Leu Ala Lys Tyr Met Cys Glu Asn Gln Asp Ser
65                  70                  75                  80

Ile Ser Thr Lys Leu Lys Glu Cys Cys Asp Lys Pro Val Leu Glu Lys
                85                  90                  95

Ser Gln Cys Leu Ala Glu Val Glu Arg Asp Glu Leu Pro Gly Asp Leu
                100                 105                 110

Pro Ser Leu Ala Ala Asp Phe Val Glu Asp Lys Glu Val Cys Lys Asn
            115                 120                 125

Tyr Gln Glu Ala Lys Asp Val Phe Leu Gly Thr Phe Leu Tyr Glu Tyr
        130                 135                 140

Ser Arg Arg His Pro Glu Tyr Ser Val Ser Leu Leu Leu Arg Leu Ala
145                 150                 155                 160

Lys Glu Tyr Glu Ala Thr Leu Glu Lys Cys Cys Ala Thr Asp Asp Pro
                165                 170                 175

Pro Thr Cys Tyr Ala Lys Val Leu Asp Glu Phe Lys Pro Leu Val Asp
            180                 185                 190

Glu Pro Gln Asn Leu Val Lys Thr Asn Cys Glu Leu Phe Glu Lys Leu
        195                 200                 205
```

```
Gly Glu Tyr Gly Phe Gln Asn Ala Leu Leu Val Arg Tyr Thr Lys Lys
        210                 215                 220

Ala Pro Gln Val Ser Thr Pro Thr Leu Val Val Glu Val Ser Arg Lys
225                 230                 235                 240

Leu Gly Lys Val Gly Thr Lys Cys Cys Lys Lys Pro Glu Ser Glu Arg
                245                 250                 255

Met Ser Cys Ala Asp Asp Phe Leu Ser
        260                 265

<210> SEQ ID NO 163
<211> LENGTH: 180
<212> TYPE: PRT
<213> ORGANISM: Canis familiaris

<400> SEQUENCE: 163

Met Gln Leu Leu Leu Leu Thr Val Gly Leu Ala Leu Ile Cys Gly Leu
1               5                   10                  15

Gln Ala Gln Glu Gly Asn His Glu Glu Pro Gln Gly Gly Leu Glu Glu
            20                  25                  30

Leu Ser Gly Arg Trp His Ser Val Ala Leu Ala Ser Asn Lys Ser Asp
        35                  40                  45

Leu Ile Lys Pro Trp Gly His Phe Arg Val Phe Ile His Ser Met Ser
50                  55                  60

Ala Lys Asp Gly Asn Leu His Gly Asp Ile Leu Ile Pro Gln Asp Gly
65                  70                  75                  80

Gln Cys Glu Lys Val Ser Leu Thr Ala Phe Lys Thr Ala Thr Ser Asn
                85                  90                  95

Lys Phe Asp Leu Glu Tyr Trp Gly His Asn Asp Leu Tyr Leu Ala Glu
            100                 105                 110

Val Asp Pro Lys Ser Tyr Leu Ile Leu Tyr Met Ile Asn Gln Tyr Asn
        115                 120                 125

Asp Asp Thr Ser Leu Val Ala His Leu Met Val Arg Asp Leu Ser Arg
130                 135                 140

Gln Gln Asp Phe Leu Pro Ala Phe Glu Ser Val Cys Glu Asp Ile Gly
145                 150                 155                 160

Leu His Lys Asp Gln Ile Val Val Leu Ser Asp Asp Arg Cys Gln
                165                 170                 175

Gly Ser Arg Asp
            180

<210> SEQ ID NO 164
<211> LENGTH: 187
<212> TYPE: PRT
<213> ORGANISM: Equus caballus

<400> SEQUENCE: 164

Met Lys Leu Leu Leu Leu Cys Leu Gly Leu Ile Leu Val Cys Ala Gln
1               5                   10                  15

Gln Glu Glu Asn Ser Asp Val Ala Ile Arg Asn Phe Asp Ile Ser Lys
            20                  25                  30

Ile Ser Gly Glu Trp Tyr Ser Ile Phe Leu Ala Ser Asp Val Lys Glu
        35                  40                  45

Lys Ile Glu Glu Asn Gly Ser Met Arg Val Phe Val Asp Val Ile Arg
50                  55                  60

Ala Leu Asp Asn Ser Ser Leu Tyr Ala Glu Tyr Gln Thr Lys Val Asn
65                  70                  75                  80
```

```
Gly Glu Cys Thr Glu Phe Pro Met Val Phe Asp Lys Thr Glu Glu Asp
                85                  90                  95

Gly Val Tyr Ser Leu Asn Tyr Asp Gly Tyr Asn Val Phe Arg Ile Ser
            100                 105                 110

Glu Phe Glu Asn Asp Glu His Ile Ile Leu Tyr Leu Val Asn Phe Asp
        115                 120                 125

Lys Asp Arg Pro Phe Gln Leu Phe Glu Phe Tyr Ala Arg Glu Pro Asp
    130                 135                 140

Val Ser Pro Glu Ile Lys Glu Glu Phe Val Lys Ile Val Gln Lys Arg
145                 150                 155                 160

Gly Ile Val Lys Glu Asn Ile Ile Asp Leu Thr Lys Ile Asp Arg Cys
                165                 170                 175

Phe Gln Leu Arg Gly Asn Gly Val Ala Gln Ala
            180                 185

<210> SEQ ID NO 165
<211> LENGTH: 29
<212> TYPE: PRT
<213> ORGANISM: Equus caballus
<220> FEATURE:
<221> NAME/KEY: UNSURE
<222> LOCATION: (3)..(3)
<223> OTHER INFORMATION: Xaa = unknown
<220> FEATURE:
<221> NAME/KEY: UNSURE
<222> LOCATION: (28)..(28)
<223> OTHER INFORMATION: Xaa = unknown

<400> SEQUENCE: 165

Ser Gln Xaa Pro Gln Ser Glu Thr Asp Tyr Ser Gln Leu Ser Gly Glu
1               5                   10                  15

Trp Asn Thr Ile Tyr Gly Ala Ala Ser Asn Ile Xaa Lys
            20                  25

<210> SEQ ID NO 166
<211> LENGTH: 211
<212> TYPE: PRT
<213> ORGANISM: Euroglyphus maynei

<400> SEQUENCE: 166

Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140

Ile Lys Asp Leu Asn Ala Phe Arg His Tyr Asp Gly Arg Thr Ile Met
145                 150                 155                 160
```

Gln His Asp Asn Gly Tyr Gln Pro Asn Tyr His Ala Val Asn Ile Val
            165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
            195                 200                 205

Ile Asn Leu
    210

<210> SEQ ID NO 167
<211> LENGTH: 211
<212> TYPE: PRT
<213> ORGANISM: Euroglyphus maynei

<400> SEQUENCE: 167

Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
        195                 200                 205

Ile Asn Leu
    210

<210> SEQ ID NO 168
<211> LENGTH: 211
<212> TYPE: PRT
<213> ORGANISM: Euroglyphus maynei

<400> SEQUENCE: 168

Glu Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

```
Leu Ala Tyr Arg Asn Gln Ser Leu Asp Leu Ala Glu Gln Glu Leu Val
     50                  55                  60

Asp Cys Ala Ser Gln His Gly Cys His Gly Asp Thr Ile Pro Arg Gly
 65                  70                  75                  80

Ile Glu Tyr Ile Gln His Asn Gly Val Val Gln Glu Ser Tyr Tyr Arg
                 85                  90                  95

Tyr Val Ala Arg Glu Gln Ser Cys Arg Arg Pro Asn Ala Gln Arg Phe
            100                 105                 110

Gly Ile Ser Asn Tyr Cys Gln Ile Tyr Pro Pro Asn Ala Asn Lys Ile
            115                 120                 125

Arg Glu Ala Leu Ala Gln Thr His Ser Ala Ile Ala Val Ile Ile Gly
       130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175

Gly Tyr Ser Asn Ala Gln Gly Val Asp Tyr Trp Ile Val Arg Asn Ser
            180                 185                 190

Trp Asp Thr Asn Trp Gly Asp Asn Gly Tyr Gly Tyr Phe Ala Ala Asn
       195                 200                 205

Ile Asp Leu
   210

<210> SEQ ID NO 169
<211> LENGTH: 212
<212> TYPE: PRT
<213> ORGANISM: Euroglyphus maynei

<400> SEQUENCE: 169

Glu Thr Ser Ala Cys Arg Ile Asn Ser Val Asn Val Pro Ser Glu Leu
 1               5                  10                  15

Asp Leu Arg Ser Leu Arg Thr Val Thr Pro Ile Arg Met Gln Gly Gly
             20                  25                  30

Cys Gly Ser Cys Trp Ala Phe Ser Gly Val Ala Ala Thr Glu Ser Ala
         35                  40                  45

Tyr Leu Ala Tyr Arg Asn Thr Ser Leu Asp Leu Ser Glu Gln Glu Leu
     50                  55                  60

Val Asp Cys Ala Ser Gln His Gly Cys His Gly Asp Thr Ile Pro Arg
 65                  70                  75                  80

Gly Ile Glu Tyr Ile Gln Gln Asn Gly Val Val Glu Glu Arg Ser Tyr
                 85                  90                  95

Pro Tyr Val Ala Arg Glu Gln Gln Cys Arg Arg Pro Asn Ser Gln His
            100                 105                 110

Tyr Gly Ile Ser Asn Tyr Cys Gln Ile Tyr Pro Pro Asp Val Lys Gln
            115                 120                 125

Ile Arg Glu Ala Leu Thr Gln Thr His Thr Ala Ile Ala Val Ile Ile
       130                 135                 140

Gly Ile Lys Asp Leu Arg Ala Phe Gln His Tyr Asp Gly Arg Thr Ile
145                 150                 155                 160

Ile Gln His Asp Asn Gly Tyr Gln Pro Asn Tyr His Ala Val Asn Ile
                165                 170                 175

Val Gly Tyr Gly Ser Thr Gln Gly Val Asp Tyr Trp Ile Val Arg Asn
            180                 185                 190

Ser Trp Asp Thr Thr Trp Gly Asp Ser Gly Tyr Gly Tyr Phe Gln Ala
       195                 200                 205
```

Gly Asn Asn Leu
                210

<210> SEQ ID NO 170
<211> LENGTH: 307
<212> TYPE: PRT
<213> ORGANISM: Poa pratensis

<400> SEQUENCE: 170

Met Ala Val Gln Lys Tyr Thr Val Ala Leu Phe Leu Val Ala Leu Val
1               5                   10                  15

Val Gly Pro Ala Ala Ser Tyr Ala Ala Asp Leu Ser Tyr Gly Ala Pro
            20                  25                  30

Ala Thr Pro Ala Ala Pro Ala Ala Gly Tyr Thr Pro Ala Ala Pro Ala
        35                  40                  45

Gly Ala Ala Pro Lys Ala Thr Thr Asp Glu Gln Lys Met Ile Glu Lys
    50                  55                  60

Ile Asn Val Gly Phe Lys Ala Val Ala Ala Gly Gly Val Pro
65                  70                  75                  80

Ala Ala Asn Lys Tyr Lys Thr Phe Val Ala Thr Phe Gly Ala Ala Ser
                85                  90                  95

Asn Lys Ala Phe Ala Glu Ala Leu Ser Thr Glu Pro Lys Gly Ala Ala
            100                 105                 110

Val Asp Ser Ser Lys Ala Ala Leu Thr Ser Lys Leu Asp Ala Ala Tyr
        115                 120                 125

Lys Leu Ala Tyr Lys Ser Ala Glu Gly Ala Thr Pro Glu Ala Lys Tyr
    130                 135                 140

Asp Asp Tyr Val Ala Thr Leu Ser Glu Ala Leu Arg Ile Ile Ala Gly
145                 150                 155                 160

Thr Leu Glu Val His Gly Val Lys Pro Ala Ala Glu Glu Val Lys Ala
                165                 170                 175

Thr Pro Ala Gly Glu Leu Gln Val Ile Asp Lys Val Asp Ala Ala Phe
            180                 185                 190

Lys Val Ala Ala Thr Ala Ala Asn Ala Ala Pro Ala Asn Asp Lys Phe
        195                 200                 205

Thr Val Phe Glu Ala Ala Phe Asn Asp Ala Ile Lys Ala Ser Thr Gly
    210                 215                 220

Gly Ala Tyr Gln Ser Tyr Lys Phe Ile Pro Ala Leu Glu Ala Ala Val
225                 230                 235                 240

Lys Gln Ser Tyr Ala Ala Thr Val Ala Thr Ala Pro Ala Val Lys Tyr
                245                 250                 255

Thr Val Phe Glu Thr Ala Leu Lys Lys Ala Ile Thr Ala Met Ser Gln
            260                 265                 270

Ala Gln Lys Ala Ala Lys Pro Ala Ala Ala Thr Gly Thr Ala Thr
        275                 280                 285

Ala Ala Val Gly Ala Ala Thr Gly Ala Ala Thr Ala Ala Gly Gly
    290                 295                 300

Tyr Lys Val
305

<210> SEQ ID NO 171
<211> LENGTH: 333
<212> TYPE: PRT
<213> ORGANISM: Poa pratensis

<400> SEQUENCE: 171

Met Ala Val His Gln Tyr Thr Val Ala Leu Phe Leu Ala Val Ala Leu

```
            1               5                  10                 15
      Val Ala Gly Pro Ala Ala Ser Tyr Ala Ala Asp Val Gly Tyr Gly Ala
                      20                  25                 30

Pro Ala Thr Leu Ala Thr Pro Ala Thr Pro Ala Ala Pro Ala Ala Gly
                      35                  40                  45

Tyr Thr Pro Ala Ala Pro Ala Gly Ala Ala Pro Lys Ala Thr Thr Asp
                      50                  55                  60

Gln Gln Lys Leu Ile Glu Lys Ile Asn Ala Gly Phe Lys Ala Ala Val
       65                  70                  75                  80

Ala Ala Ala Ala Gly Val Pro Val Asp Lys Tyr Lys Thr Phe Val
                          85                  90                  95

Ala Thr Phe Gly Thr Ala Ser Asn Lys Ala Phe Ala Glu Ala Leu Ser
                         100                 105                 110

Thr Glu Pro Lys Gly Ala Ala Ala Ser Ser Asn Ala Val Leu Thr
                         115                 120                 125

Ser Lys Leu Asp Ala Ala Tyr Lys Leu Ala Tyr Lys Ser Ala Glu Gly
                         130                 135                 140

Ala Thr Pro Glu Ala Lys Tyr Asp Ala Tyr Val Ala Thr Leu Ser Glu
      145                 150                 155                 160

Ala Leu Arg Ile Ile Ala Gly Thr Leu Glu Val His Ala Val Lys Pro
                         165                 170                 175

Ala Gly Glu Glu Val Lys Ala Ile Pro Ala Gly Glu Leu Gln Val Ile
                         180                 185                 190

Asp Lys Val Asp Ala Ala Phe Lys Val Ala Thr Ala Ala Asn Ala
                         195                 200                 205

Ala Pro Ala Asn Asp Lys Phe Thr Val Phe Glu Ala Ala Phe Asn Asp
                         210                 215                 220

Ala Ile Lys Ala Ser Thr Gly Gly Ala Tyr Gln Ser Tyr Lys Phe Ile
      225                 230                 235                 240

Pro Ala Leu Glu Ala Ala Val Lys Gln Ser Tyr Ala Ala Thr Val Ala
                         245                 250                 255

Thr Ala Pro Ala Val Lys Tyr Thr Val Phe Glu Thr Ala Leu Lys Lys
                         260                 265                 270

Ala Ile Thr Ala Met Ser Gln Ala Gln Lys Ala Ala Lys Pro Ala Ala
                         275                 280                 285

Ala Val Thr Ala Thr Ala Thr Gly Ala Val Gly Ala Ala Thr Gly Ala
                         290                 295                 300

Val Gly Ala Ala Thr Gly Ala Thr Ala Ala Gly Gly Tyr Lys
      305                 310                 315                 320

Thr Gly Ala Ala Thr Pro Thr Ala Gly Gly Tyr Lys Val
                         325                 330

<210> SEQ ID NO 172
<211> LENGTH: 373
<212> TYPE: PRT
<213> ORGANISM: Poa pratensis

<400> SEQUENCE: 172

Met Asp Lys Ala Asn Gly Ala Tyr Lys Thr Ala Leu Lys Ala Ser
 1               5                  10                  15

Ala Val Ala Pro Ala Glu Lys Phe Pro Val Phe Gln Ala Thr Phe Asp
                 20                  25                  30

Lys Asn Leu Lys Glu Gly Leu Ser Gly Pro Asp Ala Val Gly Phe Ala
                 35                  40                  45

Lys Lys Leu Asp Ala Phe Ile Gln Thr Ser Tyr Leu Ser Thr Lys Ala
```

```
            50                  55                  60
Ala Glu Pro Lys Glu Lys Phe Asp Leu Phe Val Leu Ser Leu Thr Glu
 65                  70                  75                  80

Val Leu Arg Phe Met Ala Gly Ala Val Lys Ala Pro Ala Ser Lys
                 85                  90                  95

Phe Pro Ala Lys Pro Ala Pro Lys Val Ala Ala Tyr Thr Pro Ala Ala
                100                 105                 110

Pro Ala Gly Ala Ala Pro Lys Ala Thr Thr Asp Glu Gln Lys Leu Ile
                115                 120                 125

Glu Lys Ile Asn Val Gly Phe Lys Ala Ala Val Ala Ala Ala Gly
            130                 135                 140

Val Pro Ala Ala Ser Lys Tyr Lys Thr Phe Val Ala Thr Phe Gly Ala
145                 150                 155                 160

Ala Ser Asn Lys Ala Phe Ala Glu Ala Leu Ser Thr Glu Pro Lys Gly
                165                 170                 175

Ala Ala Val Ala Ser Ser Lys Ala Val Leu Thr Ser Lys Leu Asp Ala
                180                 185                 190

Ala Tyr Lys Leu Ala Tyr Lys Ser Ala Glu Gly Ala Thr Pro Glu Ala
                195                 200                 205

Lys Tyr Asp Ala Tyr Val Ala Thr Leu Ser Glu Ala Leu Arg Ile Ile
210                 215                 220

Ala Gly Thr Leu Glu Val His Gly Val Lys Pro Ala Glu Glu Val
225                 230                 235                 240

Lys Ala Ile Pro Ala Gly Glu Leu Gln Val Ile Asp Lys Val Asp Ala
                245                 250                 255

Ala Phe Lys Val Ala Ala Thr Ala Ala Asn Ala Ala Pro Ala Asn Asp
                260                 265                 270

Lys Phe Thr Val Phe Glu Ala Ala Phe Asn Asp Ala Ile Lys Ala Ser
                275                 280                 285

Thr Gly Gly Ala Tyr Gln Ser Tyr Lys Phe Ile Pro Ala Leu Glu Ala
                290                 295                 300

Ala Val Lys Gln Ser Tyr Ala Ala Thr Val Ala Thr Ala Pro Ala Val
305                 310                 315                 320

Lys Tyr Thr Val Phe Glu Thr Ala Leu Lys Lys Ala Ile Thr Ala Met
                325                 330                 335

Ser Gln Ala Gln Lys Ala Lys Pro Ala Ala Val Thr Gly Thr
                340                 345                 350

Ala Thr Ser Ala Val Gly Ala Ala Thr Gly Ala Ala Thr Ala Ala Ala
                355                 360                 365

Gly Gly Tyr Lys Val
        370

<210> SEQ ID NO 173
<211> LENGTH: 685
<212> TYPE: PRT
<213> ORGANISM: Periplaneta americana

<400> SEQUENCE: 173

Met Lys Thr Ala Leu Val Phe Ala Ala Val Ala Phe Val Ala Ala
 1               5                  10                  15

Arg Phe Pro Asp His Lys Asp Tyr Lys Gln Leu Ala Asp Lys Gln Phe
                 20                  25                  30

Leu Ala Lys Gln Arg Asp Val Leu Arg Leu Phe His Arg Val His Gln
             35                  40                  45

His Asn Ile Leu Asn Asp Gln Val Glu Val Gly Ile Pro Met Thr Ser
```

```
            50                  55                  60
Lys Gln Thr Ser Ala Thr Thr Val Pro Pro Ser Gly Glu Ala Val His
 65                  70                  75                  80

Gly Val Leu Gln Glu Gly His Ala Arg Pro Arg Gly Glu Pro Phe Ser
                     85                  90                  95

Val Asn Tyr Glu Lys His Arg Glu Gln Ala Ile Met Leu Tyr Asp Leu
                    100                 105                 110

Leu Tyr Phe Ala Asn Asp Tyr Asp Thr Phe Tyr Lys Thr Ala Cys Trp
                115                 120                 125

Ala Arg Asp Arg Val Asn Glu Gly Met Phe Met Tyr Ser Phe Ser Ile
130                 135                 140

Ala Val Phe His Arg Asp Asp Met Gln Gly Val Met Leu Pro Pro Pro
145                 150                 155                 160

Tyr Glu Val Tyr Pro Tyr Leu Phe Val Asp His Asp Val Ile His Met
                165                 170                 175

Ala Gln Lys Tyr Trp Met Lys Asn Ala Gly Ser Gly Glu His His Ser
                180                 185                 190

His Val Ile Pro Val Asn Phe Thr Leu Arg Thr Gln Asp His Leu Leu
                195                 200                 205

Ala Tyr Phe Thr Ser Asp Val Asn Leu Asn Ala Phe Asn Thr Tyr Tyr
                210                 215                 220

Arg Tyr Tyr Tyr Pro Ser Trp Tyr Asn Thr Thr Leu Tyr Gly His Asn
225                 230                 235                 240

Ile Asp Arg Arg Gly Glu Gln Phe Tyr Tyr Thr Tyr Lys Gln Ile Tyr
                245                 250                 255

Ala Arg Tyr Phe Leu Glu Arg Leu Ser Asn Asp Leu Pro Asp Val Tyr
                260                 265                 270

Pro Phe Tyr Tyr Ser Lys Pro Val Lys Ser Ala Tyr Asn Pro Asn Leu
                275                 280                 285

Arg Tyr His Asn Gly Glu Glu Met Pro Val Arg Pro Ser Asn Met Tyr
                290                 295                 300

Val Thr Asn Phe Asp Leu Tyr Tyr Ile Ala Asp Ile Lys Asn Tyr Glu
305                 310                 315                 320

Lys Arg Val Glu Asp Ala Ile Asp Phe Gly Tyr Ala Phe Asp Glu His
                325                 330                 335

Met Lys Pro His Ser Leu Tyr His Asp Val His Gly Met Glu Tyr Leu
                340                 345                 350

Ala Asp Met Ile Glu Gly Asn Met Asp Ser Pro Asn Phe Tyr Phe Tyr
                355                 360                 365

Gly Ser Ile Tyr His Met Tyr His Ser Met Ile Gly His Ile Val Asp
370                 375                 380

Pro Tyr His Lys Met Gly Leu Ala Pro Ser Leu Glu His Pro Glu Thr
385                 390                 395                 400

Val Leu Arg Asp Pro Val Phe Tyr Gln Leu Trp Lys Arg Val Asp His
                405                 410                 415

Leu Phe Gln Lys Tyr Lys Asn Arg Leu Pro Arg Tyr Thr His Asp Glu
                420                 425                 430

Leu Ala Phe Glu Gly Val Lys Val Glu Asn Val Asp Val Gly Lys Leu
                435                 440                 445

Tyr Thr Tyr Phe Glu Gln Tyr Asp Met Ser Leu Asp Met Ala Val Tyr
                450                 455                 460

Val Asn Asn Val Asp Gln Ile Ser Asn Val Asp Val Gln Leu Ala Val
465                 470                 475                 480
```

```
Arg Leu Asn His Lys Pro Phe Thr Tyr Asn Ile Glu Val Ser Ser Asp
                485                 490                 495

Lys Ala Gln Asp Val Tyr Val Ala Val Phe Leu Gly Pro Lys Tyr Asp
            500                 505                 510

Tyr Leu Gly Arg Glu Tyr Asp Leu Asn Asp Arg Arg His Tyr Phe Val
            515                 520                 525

Glu Met Asp Arg Phe Pro Tyr His Val Gly Ala Gly Lys Thr Val Ile
            530                 535                 540

Glu Arg Asn Ser His Asp Ser Asn Ile Ile Ala Pro Glu Arg Asp Ser
545                 550                 555                 560

Tyr Arg Thr Phe Tyr Lys Lys Val Gln Glu Ala Tyr Glu Gly Lys Ser
                565                 570                 575

Gln Tyr Tyr Val Asp Lys Gly His Asn Tyr Cys Gly Tyr Pro Glu Asn
            580                 585                 590

Leu Leu Ile Pro Lys Gly Lys Gly Gly Gln Ala Tyr Thr Phe Tyr
                595                 600                 605

Val Ile Val Thr Pro Tyr Val Lys Gln Asp Glu His Asp Phe Glu Pro
            610                 615                 620

Tyr Asn Tyr Lys Ala Phe Ser Tyr Cys Gly Val Gly Ser Glu Arg Lys
625                 630                 635                 640

Tyr Pro Asp Asn Lys Pro Leu Gly Tyr Pro Phe Asp Arg Lys Ile Tyr
                645                 650                 655

Ser Asn Asp Phe Tyr Thr Pro Asn Met Tyr Phe Lys Asp Val Ile Ile
            660                 665                 670

Phe His Lys Lys Tyr Asp Glu Val Gly Val Gln Gly His
                675                 680                 685

<210> SEQ ID NO 174
<211> LENGTH: 446
<212> TYPE: PRT
<213> ORGANISM: Periplaneta americana

<400> SEQUENCE: 174

Ile Asn Glu Ile His Ser Ile Ile Gly Leu Pro Pro Phe Val Pro Pro
1               5                   10                  15

Ser Arg Arg His Ala Arg Arg Gly Val Gly Ile Asn Gly Leu Ile Asp
                20                  25                  30

Asp Val Ile Ala Ile Leu Pro Val Asp Glu Leu Lys Ala Leu Phe Gln
            35                  40                  45

Glu Lys Leu Glu Thr Ser Pro Asp Phe Lys Ala Leu Tyr Asp Ala Ile
50                  55                  60

Arg Ser Pro Glu Phe Gln Ser Ile Ile Ser Thr Leu Asn Ala Met Gln
65                  70                  75                  80

Arg Ser Glu His His Gln Asn Leu Arg Asp Lys Gly Val Asp Val Asp
                85                  90                  95

His Phe Ile Gln Leu Ile Arg Ala Leu Phe Gly Leu Ser Arg Ala Ala
            100                 105                 110

Arg Asn Leu Gln Asp Asp Leu Asn Asp Phe Leu His Ser Leu Glu Pro
            115                 120                 125

Ile Ser Pro Arg His Arg His Gly Leu Pro Arg Gln Arg Arg Ser
            130                 135                 140

Ala Arg Val Ser Ala Tyr Leu His Ala Asp Asp Phe His Lys Ile Ile
145                 150                 155                 160

Thr Thr Ile Glu Ala Leu Pro Glu Phe Ala Asn Phe Tyr Asn Phe Leu
                165                 170                 175
```

```
Lys Glu His Gly Leu Asp Val Val Asp Tyr Ile Asn Glu Ile His Ser
            180                 185                 190

Ile Ile Gly Leu Pro Pro Phe Val Pro Pro Ser Arg His Ala Arg
        195                 200                 205

Arg Gly Val Gly Ile Asn Gly Leu Ile Asp Asp Val Ile Ala Ile Leu
    210                 215                 220

Pro Val Asp Glu Leu Lys Ala Leu Phe Gln Glu Lys Leu Glu Thr Ser
225                 230                 235                 240

Pro Asp Phe Lys Ala Leu Tyr Asp Ala Ile Arg Ser Pro Glu Phe Gln
                245                 250                 255

Ser Ile Ile Ser Thr Leu Asn Ala Met Pro Glu Tyr Gln Glu Leu Leu
                260                 265                 270

Gln Asn Leu Arg Asp Lys Gly Val Asp Val Asp His Phe Ile Arg Val
            275                 280                 285

Asp Gln Gly Thr Leu Arg Thr Leu Ser Ser Gly Gln Arg Asn Leu Gln
        290                 295                 300

Asp Asp Leu Asn Asp Phe Leu Ala Leu Ile Pro Thr Asp Gln Ile Leu
305                 310                 315                 320

Ala Ile Ala Met Asp Tyr Leu Ala Asn Asp Ala Glu Val Gln Glu Leu
                325                 330                 335

Val Ala Tyr Leu Gln Ser Asp Asp Phe His Lys Ile Ile Thr Thr Ile
                340                 345                 350

Glu Ala Leu Pro Glu Phe Ala Asn Phe Tyr Asn Phe Leu Lys Glu His
            355                 360                 365

Gly Leu Asp Val Val Asp Tyr Ile Asn Glu Ile His Ser Ile Ile Gly
        370                 375                 380

Leu Pro Pro Phe Val Pro Pro Ser Gln Arg His Ala Arg Arg Gly Val
385                 390                 395                 400

Gly Ile Asn Gly Leu Ile Asp Asp Val Ile Ala Ile Leu Pro Val Asp
                405                 410                 415

Glu Leu Lys Ala Leu Phe Gln Glu Lys Leu Glu Thr Ser Pro Asp Phe
                420                 425                 430

Lys Ala Leu Tyr Asp Ala Ile Asp Leu Arg Ser Ser Arg Ala
            435                 440                 445

<210> SEQ ID NO 175
<211> LENGTH: 352
<212> TYPE: PRT
<213> ORGANISM: Blattella germanica

<400> SEQUENCE: 175

Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
                20                  25                  30

Val Phe Ile Asn Thr Gln Tyr Ala Gly Ile Thr Lys Ile Gly Asn Gln
            35                  40                  45

Asn Phe Leu Thr Val Phe Asp Ser Thr Ser Cys Asn Val Val Val Ala
        50                  55                  60

Ser Gln Glu Cys Val Gly Gly Ala Cys Val Cys Pro Asn Leu Gln Lys
65                  70                  75                  80

Tyr Glu Lys Leu Lys Pro Lys Tyr Ile Ser Asp Gly Asn Val Gln Val
                85                  90                  95

Lys Phe Asp Thr Gly Ser Ala Val Gly Arg Gly Ile Glu Asp Ser
                100                 105                 110
```

Leu Thr Ile Ser Asn Leu Thr Thr Ser Gln Gln Asp Ile Val Leu Ala
            115                 120                 125

Asp Glu Leu Ser Gln Glu Val Cys Ile Leu Ser Ala Asp Val Val Val
        130                 135                 140

Gly Ile Ala Ala Pro Gly Cys Pro Asn Ala Leu Lys Gly Lys Thr Val
145                 150                 155                 160

Leu Glu Asn Phe Val Glu Glu Asn Leu Ile Ala Pro Val Phe Ser Ile
                165                 170                 175

His His Ala Arg Phe Gln Asp Gly Glu His Phe Gly Glu Ile Ile Phe
            180                 185                 190

Gly Gly Ser Asp Trp Lys Tyr Val Asp Gly Phe Thr Tyr Val Pro
            195                 200                 205

Leu Val Gly Asp Ser Trp Lys Phe Arg Leu Asp Gly Val Lys Ile
210                 215                 220

Gly Asp Thr Thr Val Ala Pro Ala Gly Thr Gln Ala Ile Ile Asp Thr
225                 230                 235                 240

Ser Lys Ala Ile Ile Val Gly Pro Lys Ala Tyr Val Asn Pro Ile Asn
                245                 250                 255

Glu Ala Ile Gly Cys Val Val Glu Lys Thr Thr Thr Arg Arg Ile Cys
            260                 265                 270

Lys Leu Asp Cys Ser Lys Ile Pro Ser Leu Pro Asp Val Thr Phe Val
275                 280                 285

Ile Asn Gly Arg Asn Phe Asn Ile Ser Ser Gln Tyr Ile Gln Gln
290                 295                 300

Asn Gly Asn Leu Cys Tyr Ser Gly Phe Gln Pro Cys Gly His Ser Asp
305                 310                 315                 320

His Phe Phe Ile Gly Asp Phe Phe Val Asp His Tyr Tyr Ser Glu Phe
                325                 330                 335

Asn Trp Glu Asn Lys Thr Met Gly Phe Gly Arg Ser Val Glu Ser Val
            340                 345                 350

<210> SEQ ID NO 176
<211> LENGTH: 182
<212> TYPE: PRT
<213> ORGANISM: Blattella germanica

<400> SEQUENCE: 176

Ala Val Leu Ala Leu Cys Ala Thr Asp Thr Leu Ala Asn Glu Asp Cys
1               5                   10                  15

Phe Arg His Glu Ser Leu Val Pro Asn Leu Asp Tyr Glu Arg Phe Arg
            20                  25                  30

Gly Ser Trp Ile Ile Ala Ala Gly Thr Ser Glu Ala Leu Thr Gln Tyr
        35                  40                  45

Lys Cys Trp Ile Asp Arg Phe Ser Tyr Asp Ala Leu Val Ser Lys
    50                  55                  60

Tyr Thr Asp Ser Gln Gly Lys Asn Arg Thr Thr Ile Arg Gly Arg Thr
65                  70                  75                  80

Lys Phe Glu Gly Asn Lys Phe Thr Ile Asp Tyr Asn Asp Lys Gly Lys
                85                  90                  95

Ala Phe Ser Ala Pro Tyr Ser Val Leu Ala Thr Asp Tyr Glu Asn Tyr
            100                 105                 110

Ala Ile Val Glu Gly Cys Pro Ala Ala Ala Asn Gly His Val Ile Tyr
        115                 120                 125

Val Gln Ile Arg Phe Ser Val Arg Arg Phe His Pro Lys Leu Gly Asp
    130                 135                 140

-continued

```
Lys Glu Met Ile Gln His Tyr Thr Leu Asp Gln Val Asn Gln His Lys
145                 150                 155                 160

Lys Ala Ile Glu Glu Asp Leu Lys His Phe Asn Leu Lys Tyr Glu Asp
                165                 170                 175

Leu His Ser Thr Cys His
            180

<210> SEQ ID NO 177
<211> LENGTH: 200
<212> TYPE: PRT
<213> ORGANISM: Blattella germanica

<400> SEQUENCE: 177

Tyr Lys Leu Thr Tyr Cys Pro Val Lys Ala Leu Gly Glu Pro Ile Arg
1               5                   10                  15

Phe Leu Leu Ser Tyr Gly Glu Lys Asp Phe Glu Asp Tyr Arg Phe Gln
                20                  25                  30

Glu Gly Asp Trp Pro Asn Leu Lys Pro Ser Met Pro Phe Gly Lys Thr
            35                  40                  45

Pro Val Leu Glu Ile Asp Gly Lys Gln Thr His Gln Ser Val Ala Ile
        50                  55                  60

Ser Arg Tyr Leu Gly Lys Gln Phe Gly Leu Ser Gly Lys Asp Asp Trp
65                  70                  75                  80

Glu Asn Leu Glu Ile Asp Met Ile Val Asp Thr Ile Ser Asp Phe Arg
                85                  90                  95

Ala Ala Ile Ala Asn Tyr His Tyr Asp Ala Asp Glu Asn Ser Lys Gln
                100                 105                 110

Lys Lys Trp Asp Pro Leu Lys Lys Glu Thr Ile Pro Tyr Tyr Thr Lys
            115                 120                 125

Lys Phe Asp Glu Val Val Lys Ala Asn Gly Gly Tyr Leu Ala Ala Gly
        130                 135                 140

Lys Leu Thr Trp Ala Asp Phe Tyr Phe Val Ala Ile Leu Asp Tyr Leu
145                 150                 155                 160

Asn His Met Ala Lys Glu Asp Leu Val Ala Asn Gln Pro Asn Leu Lys
                165                 170                 175

Ala Leu Arg Glu Lys Val Leu Gly Leu Pro Ala Ile Lys Ala Trp Val
                180                 185                 190

Ala Lys Arg Pro Pro Thr Asp Leu
            195                 200
```